US011035855B2

(12) United States Patent
Pamula et al.

(10) Patent No.: US 11,035,855 B2
(45) Date of Patent: Jun. 15, 2021

(54) POINT-OF-BIRTH SYSTEM AND INSTRUMENT, BIOCHEMICAL CARTRIDGE, AND METHODS FOR NEWBORN SCREENING

(71) Applicant: Baebies, Inc., Durham, NC (US)

(72) Inventors: Vamsee Pamula, Durham, NC (US); Vijay Srinivasan, Durham, NC (US); Donovan Bort, Durham, NC (US)

(73) Assignee: Baebies, Inc., Durham, NC (US)

( * ) Notice: Subject to any disclaimer, the term of this patent is extended or adjusted under 35 U.S.C. 154(b) by 95 days.

(21) Appl. No.: 16/096,701

(22) PCT Filed: May 1, 2017

(86) PCT No.: PCT/US2017/030425
§ 371 (c)(1),
(2) Date: Oct. 26, 2018

(87) PCT Pub. No.: WO2017/190139
PCT Pub. Date: Nov. 2, 2017

(65) Prior Publication Data

US 2019/0154678 A1 May 23, 2019

Related U.S. Application Data

(60) Provisional application No. 62/329,591, filed on Apr. 29, 2016.

(51) Int. Cl.

| | |
|---|---|
| *G01N 33/543* | (2006.01) |
| *B01L 3/00* | (2006.01) |
| *G01N 35/00* | (2006.01) |
| *G01N 33/53* | (2006.01) |
| *G01N 21/64* | (2006.01) |
| *G01N 21/78* | (2006.01) |

(52) U.S. Cl.
CPC .. *G01N 33/54366* (2013.01); *B01L 3/502738* (2013.01); *G01N 33/53* (2013.01);
(Continued)

(58) Field of Classification Search
CPC ............ G01N 33/54366; G01N 33/53; G01N 35/00069; G01N 21/645; G01N 21/78;
(Continued)

(56) References Cited

U.S. PATENT DOCUMENTS 6,194,160 B1 2/2001 Levin
7,964,147 B2 6/2011 Schulat et al.
(Continued)

FOREIGN PATENT DOCUMENTS

WO 2015048173 A2 4/2015

*Primary Examiner* — Melanie Brown
(74) *Attorney, Agent, or Firm* — E. Eric Mills; Nexsen Pruet, PLLC

(57) ABSTRACT

A point-of-birth system and instrument, biochemical cartridge, and methods for newborn screening is disclosed. Namely, a point-of-birth system is provided that includes a point-of-birth instrument for receiving and processing a biochemical cartridge for performing newborn screening. Further, a portable smart device, such as a smartphone or tablet, is in communication with point-of-birth instrument, wherein the smart device may include a newborn screening (NBS) mobile app. In one example, the point-of-birth system and point-of-birth instrument support newborn biological screening only. However, in another example, the point-of-birth system and point-of-birth instrument support both newborn biological screening and newborn physiological screening.

12 Claims, 66 Drawing Sheets

(52) U.S. Cl.
CPC .. *G01N 35/00069* (2013.01); *A61B 2503/045* (2013.01); *B01L 2200/027* (2013.01); *B01L 2200/0689* (2013.01); *B01L 2300/044* (2013.01); *B01L 2300/0809* (2013.01); *G01N 21/645* (2013.01); *G01N 21/78* (2013.01); *G01N 2035/0091* (2013.01); *G01N 2201/0221* (2013.01)

(58) Field of Classification Search
CPC ....... G01N 33/48771; G01N 33/48778; G01N 33/48785; G01N 33/48792; G01N 33/50; B01L 3/502738; B01L 3/5027; A61B 2503/045
See application file for complete search history.

(56) References Cited

U.S. PATENT DOCUMENTS

| | | | | |
|---|---|---|---|---|
| 2002/0085958 | A1* | 7/2002 | Nemcek | B01L 3/502715 422/400 |
| 2006/0260939 | A1 | 11/2006 | Anderson et al. | |
| 2010/0282609 | A1* | 11/2010 | Pollack | B01L 3/502792 204/450 |
| 2011/0306859 | A1 | 12/2011 | Saldivar et al. | |
| 2013/0162981 | A1* | 6/2013 | Emeric | G01N 21/78 356/72 |
| 2014/0323347 | A1 | 10/2014 | Ghatak | |
| 2015/0017078 | A1* | 1/2015 | Fattinger | B01L 3/5082 422/549 |
| 2015/0323555 | A1 | 11/2015 | Kayyem et al. | |
| 2016/0025760 | A1 | 1/2016 | Holmes | |

* cited by examiner

| | POINT-OF-BIRTH | | 12:20 PM | |
|---|---|---|---|---|
| 🔍 | | | | + ⋮ |
| | OPEN ORDERS | | COMPLETED ORDERS | |
| | NAME (LAST, FIRST) | ORDERED ASSAY | DATE ORDERED | |
| 👣 | Adder, Eric<br>801231776 | ☐ BILI – G6PD – GALT | Today, 7:52a | ▶ |
| 👣 | Amos, Charles<br>801231776 | ☐ BILI – G6PD – GALT | Today, 7:16a | ▶ |
| 👣 | Bassler, Anna<br>801231776 | ☐ BILI – G6PD – GALT | Jun 13, 2016 | ▶ |
| 👣 | Bassler, Anna<br>801231776 | ▨ BILI – G6PD – GALT | Jun 13, 2016 | ▶ |
| 👣 | Codddington, Brandon<br>801231776 | ☐ BILI – G6PD – GALT | Jun 13, 2016 | ▶ |
| 👣 | Crawford Anthony<br>801231776 | ▨ BILI – G6PD – GALT | Today, 4:34a | ▶ |

FIG. 42
700
POINT-OF-BIRTH
12:20 PM
710
OPEN ORDERS
710
Insert Cartridge
Please insert cartridge into slot
to begin
Initializing Cartridge
:23
REMAINING
DO NOT add sample until initialization is complete.
Adder. Eric
801231776

FIG. 46
700
POINT-OF-BIRTH
12:20 PM
710
OPEN ORDERS
Add Blood Sample
Add patient's sample into the cartride
port. Be s
running te
Verifying sample quantity .....
DO NOT remove cartridge.
710
Run Test
Adder. Eric
801231776

700

710 { POINT-OF-BIRTH 12:20 PM

710 { ← COMPLETED ORDERS

710 {
Adder. Eric
801231776

ASSAYS ORDERED
BILI – G6PD - GALT

ORDERED BY
Marylyn Schaeffer MD
June 14, 2016 8:32a

✓ COMPLETED BY
Jane Doe
June 14, 2016 10:07a

RESULTS    ( View Details )    ( Print Results )

Total Bilirubin
6.8 mg/dL     | LOW | NORMAL ▼ | HIGH |

G6PD
24.23 U/GHb   | LOW | NORMAL | HIGH ▼ |

GALT
20.26 U/GHb   | LOW | NORMAL ▼ | HIGH |

700

| POINT-OF-BIRTH | | | 12:20 PM |
|---|---|---|---|

OPEN ORDERS     COMPLETED ORDERS

| NAME (LAST, FIRST) | ORDERED ASSAY | DATE ORDERED | |
|---|---|---|---|
| Adder. Eric<br>801231776 | ☐ BILI – G6PD – GALT | Today, 7:52a | ▸ |
| Amos, Charles<br>801231776 | ☐ BILI – G6PD – GALT | Today, 7:16a | ▸ |
| Bassler, Anna<br>801231776 | ☐ BILI – G6PD – GALT | Jun 13, 2016 | ▸ |
| Bassler, Anna<br>801231776 | ▦ BILI – G6PD – GALT | Jun 13, 2016 | ▸ |
| Codddington, Brandon<br>801231776 | ☐ BILI – G6PD – GALT | Jun 13, 2016 | ▸ |
| Crawford Anthony<br>801231776 | ▦ BILI – G6PD – GALT | Today, 4:34a | ▸ |

67% TEST IN PROGRESS     REMAINING 7:23

POINT-OF-BIRTH SYSTEM AND INSTRUMENT, BIOCHEMICAL CARTRIDGE, AND METHODS FOR NEWBORN SCREENING

CROSS REFERENCE TO RELATED APPLICATIONS

This application is a 35 U.S.C. § 371 U.S. national phase entry of International Application No. PCT/US2017/030425 having an international filing date of May 1, 2017, which claims the benefit of U.S. Provisional Application No. 62/329,591 filed Apr. 29, 2016, each of which is incorporated herein by reference in its entirety.

TECHNICAL FIELD

The presently disclosed subject matter relates generally to the processing of biological materials and more particularly to a point-of-birth system and instrument, biochemical cartridge, and methods for newborn screening.

BACKGROUND

Newborn screening (NBS) was introduced in the United States as a public health measure to screen for phenylketonuria, an inherited metabolic disorder that is best treated soon after birth, and has subsequently expanded globally to include many more treatable conditions. The field of NB S has greatly benefited from the introduction of mass spectrometry as a multiplex technology to screen for over 30 conditions from a single dried blood spot (DBS) specimen. However, mass spectrometry and other technologies used in a typical public health laboratory for high-throughput applications require significant liquid handling and specialized technicians. Moreover, the traditional paradigm for newborn screening is through analysis of DBS specimens, which are mailed to a public health or reference laboratory for processing with a few days' turnaround, which results in delays in diagnosing some deadly diseases. Certain conditions demand immediate diagnosis and initiation of treatment within hours of birth before devastating and often irreversible health consequences occur. Some of these disorders include hyperbilirubinemia, galactosemia, medium chain acyl-CoA dehydrogenase (MCAD) deficiency, hyperammonemia, congenital hypothyroidism (CH), and congenital adrenal hyperplasia (CAH).

There is currently not a single point-of-birth newborn testing panel available for biochemical screening, although screening for hearing disorders is performed at point of birth using automated brain stem response and pulse oximetry is performed to screen for congenital heart defects.

SUMMARY

The present invention relates to a point-of-birth testing system, a point-of-birth instrument, and a biological cartridge. The present invention further relates to a method of newborn screening and method for using a point-of-birth newborn screening system.

In one aspect of the present invention, a point-of-birth testing system for newborn screening is disclosed. The point-of-birth testing system may include a point-of-birth instrument for processing sample fluid of a newborn, a smart display communicatively coupled to the point-of-birth instrument to provide user interface and operate the point-of-birth instrument, and a biochemical cartridge for receiving sample fluid to be processed. The biochemical cartridge may insert into the point-of-birth instrument for processing the sample fluid. Further, the smart display may communicate results of the processed sample fluid.

The biochemical cartridge of the point-of-birth testing system of the present invention may be portable. Further, the point-of-birth instrument of the point-of-birth testing system of the present invention may be portable. The smart display of the point-of-birth system of the present invention may be a portable smart device. Alternatively, the smart display of the point-of-birth system may be a laptop computer. In yet a further alternative embodiment, the smart display is a display built into the point-of-birth instrument.

In one embodiment, the point-of-birth testing system of the present invention may only support newborn biological screening. Alternatively, the point-of-birth testing system of the present invention may support both newborn biological screening and newborn physiological screening. In one embodiment of the present invention, the point-of-birth testing system may include a pulse oximetry mechanism. In another embodiment of the present invention, the point-of-birth testing system may include a hearing screening mechanism. In yet a further embodiment of the present invention, the point-of-birth testing system may include both a pulse oximetry mechanism and a hearing screening mechanism.

The point-of-birth testing system of the present invention may support multiplexed testing. Further, the point-of-birth testing system of the present invention may test multiple analytes with a single sample fluid on the biochemical cartridge.

In an embodiment of the present invention, the point-of-birth testing system may perform multiple types of biochemical tests. For example, the point-of-birth testing system of the present invention may perform multiples types of biochemical testing such as enzymatic test(s), colorimetric test(s), immunoassay test(s), and/or a nucleic acid test(s). In one embodiment of the point-of-birth testing system of the present invention, the system may perform screenings for biological markers. For example, the point-of-birth testing system of the present invention may screen for biological markers such as total bilirubin, ammonia, and/or medium-chain acyl-CoA dehydrogenase.

In one embodiment of the present invention, the smart display of the point-of-birth testing system may include a newborn screening mobile application to interface with a user and/or operate the point-of-birth instrument.

In an embodiment of the biochemical cartridge of the point-of-birth testing system of the present invention, the biochemical cartridge may include a horizontal reservoir module for holding liquids. Further, in one embodiment, the horizontal reservoir module may be angled. For example, the horizontal reservoir module may be angled 13 through 17 degrees. In one embodiment of the present invention, the biochemical cartridge includes an optics interface region. The optics interface region of the biochemical cartridge may correspond to an optics detector of the point-of-birth instrument when the biochemical cartridge is inserted into the point-of-birth instrument.

In another aspect of the present invention, a point-of-birth instrument for processing sample fluid is disclosed. The point-of-birth instrument may include a housing, a loading deck for receiving a biochemical cartridge having sample fluid, a smart display that interfaces with a user, an input reader, and a biochemical testing module that includes a processor for testing assays. The smart display of the point-of-birth instrument may provide results from the testing assays, such as to a user.

In an embodiment of the present invention, the housing of the point-of-birth instrument may include a base plate, first and second side rails mounted on the base plate, and a circuit board arranged between the side rails that controls the operations of the point-of-birth instrument. Further, the housing of the point-of-birth instrument may include a cam arranged between the side rails, a cartridge engage stepper motor, a cam belt and pulley assembly, and a motor assembly to actuate dispensing of the sample fluid of the biochemical cartridge. Moreover, the motor assembly may include a stepper motor on a stepper motor support, a spring-loaded adaptor, a motor shaft, and a motor engaging member.

In one embodiment, the housing of the point-of-birth instrument of the present invention may include a power input port. Further, the housing of the point-of-birth instrument may include a power supply assembly arranged on a power supply mounting plate.

In an embodiment of the present invention, the smart display of the point-of-birth instrument may be a smart device or laptop. The point-of-birth instrument of the present invention may include a docking station that electronically connects to a smart device or laptop. In another embodiment, point-of-birth instrument may communicate wirelessly with a smart device or laptop. In yet a further embodiment, the point-of-birth instrument may both electronically connect to a smart device or laptop as well as have the option to communicate wirelessly with the smart device or laptop. The smart display of the point-of-birth instrument may include a software application that interfaces with a user and/or allows a user to communicate the results to concerned persons, provide follow-up information, provide training for use of the instrument, perform clinical calculations, and/or perform epidemiological tracking of diseases.

In one embodiment of the point-of-birth instrument, the input reader is a barcode reader. Further, the input reader, such as a barcode reader, may scan newborn identification information.

In an embodiment of the present invention, the point-of-birth instrument may include a fluorimeter and/or an optical spectrometer. Further, the point-of-birth instrument of the present invention may include an optical detector. The point-of-birth instrument may include a pulse oximetry module and/or a hearing screening module. In one embodiment of the point-of-birth instrument of the present invention, the instrument may be portable.

In an aspect of the present invention, a biochemical cartridge for newborn screening is disclosed. The biochemical cartridge of the present invention may include a bottom substrate, a top substrate spaced from the bottom substrate by a gap, a cover positioned adjacent the top substrate, and a sample input well having a loading port and a well cap assembly for opening and closing the loading port. The sample input well may be for collection of newborn testing fluids. Further, the biochemical cartridge may be inserted into a newborn screening instrument for testing.

In one embodiment of the biochemical cartridge of the present invention, the sample input well may be integrated into the cover. The cover of the biochemical cartridge may include contoured regions. In an embodiment of the biochemical cartridge of the present invention, the gap between the top and bottom substrates may be an assay chamber.

In an embodiment of the biochemical cartridge of the present invention, the sample input well may be a horizontal reservoir module. Further, the biochemical cartridge may further include a cover gasket, a horizontal reservoir module mounting plate, and mounting posts for securing the horizontal reservoir module. In one embodiment of the present invention, the well cap assembly may include a foil strip for sealing fluid inside the horizontal reservoir module. Further, the biochemical cartridge may include a take-up reel for winding the foil strip off of the horizontal reservoir module, a reel engaging feature secured to the top substrate, and/or a reservoir module capture feature.

In an embodiment of the biochemical cartridge of the present invention, the horizontal reservoir module may include a first reservoir for holding a first sample fluid and a second reservoir for holding a second sample fluid. In one embodiment of the biochemical cartridge of the present invention, the reservoir(s) may be angled. For example, the reservoir(s) may be angled 13 through 17 degrees.

In one embodiment of the biochemical cartridge of the present invention, the cartridge supports digital microfluidics. Alternatively, the biochemical cartridge of the present invention does not support digital microfluidics. In an embodiment of the biochemical cartridge of the present invention, the newborn testing fluid may be urine and/or blood. Further, in an embodiment of the biochemical cartridge of the present invention, the bottom substrate may include a printed circuit board. In an embodiment of the biochemical cartridge of the present invention, the gap between the bottom substrate and top substrate may include filler fluid.

In yet another alternative aspect of the present invention, a method for newborn screening is disclosed. In one embodiment, the method for newborn screening includes the step of providing a point-of-birth testing system having (1) a point-of-birth instrument for processing sample fluid, (2) a smart display that interfaces with the point-of-birth instrument, and (3) a biochemical cartridge having a reservoir for receiving sample fluid for processing. Further, the method for newborn screening may include the steps of providing identification information to the testing system, loading sample fluid into the reservoir of the biochemical cartridge, sealing the reservoir of the biochemical cartridge after loading with sample fluid, loading the biochemical cartridge into the point-of-birth instrument, releasing the sample fluid into an assay of the biochemical cartridge for processing, processing of the sample fluid by the point-of-birth instrument, interfacing with the smart display to obtain results of the processed sample fluid, and/or communicating the results.

In an embodiment of the method for newborn screening, the method may further include the steps of providing a foil strip for sealing the reservoir of the biochemical cartridge after loading with sample fluid, providing a foil take-up reel on the biochemical cartridge that secures a portion of the foil strip, providing a stepper motor that is engaged with the foil take-up reel, activating the stepper motor after loading the biochemical cartridge into the point-of-birth instrument, and/or unsealing the foil strip from the reservoir after the stepper motor is activated to allow for releasing of the sample fluid.

In one embodiment of the method for newborn screening, the reservoir of the biochemical cartridge may include a first reservoir and a second reservoir. Further, the method may include the steps of providing a foil strip for sealing the first and second reservoir of the biochemical cartridge after loading both reservoirs with first and second respective sample fluids, providing a foil take-up reel on the biochemical cartridge that secures a portion of the foil strip, providing a stepper motor that is engaged with the foil take-up reel, activating the stepper motor after loading the biochemical cartridge into the point-of-birth instrument, unsealing the foil strip from the first reservoir after the stepper motor is activated to allow for releasing of the first sample fluid in the first reservoir, and/or unsealing the foil strip from the second reservoir after the first reservoir is unsealed to allow for releasing of the second sample fluid in the second reservoir.

In another aspect of the present invention, a method for using a point-of-birth newborn screening system is disclosed. In one embodiment, the method for using a point-of-birth newborn screening system includes the step of providing a smart display having a point-of-birth newborn screening software application, wherein the smart display may be in communication with a point-of-birth testing system having a point-of-birth instrument for processing sample fluid and a biochemical cartridge for receiving sample fluid for processing. Further, the method for using a point-of-birth newborn screening system of the present invention may include the steps of logging into the software application of the smart display, interfacing with the smart display by selecting an open order, scanning a sample fluid identifier on the biochemical cartridge, inserting the biochemical cartridge containing sample fluid into the point-of-birth testing instrument, interfacing with the smart display to initialize processing of the biochemical cartridge, verifying adequate fluid sample for processing of the biochemical cartridge, processing the sample fluid by the point-of-birth testing instrument, monitoring the smart display to determine the status of the processing of the sample fluid, and/or viewing test results of the processed sample fluid.

In an embodiment of the method for using a point-of-birth newborn screening system, the step of logging into the smart display may be done by manually entering a user ID and a password and/or by using a barcode reader to scan credentials. Further, in one embodiment of the method for using a point-of-birth newborn screening system, the sample fluid identifier may be a barcode reader.

In one embodiment of the method for using a point-of-birth newborn screening system, the method may further include the step of entering sample fluid identifying information to create an open order in the software application of the smart display. Further, the method for using a point-of-birth newborn screening system may include the step of collecting sample fluid from a newborn using the biochemical cartridge. In one embodiment of the method of the present invention, the step of collecting sample fluid from a newborn using the biochemical cartridge may occur after the step of scanning a sample fluid identifier on the biochemical cartridge and before the step of inserting the biochemical cartridge containing sample fluid into the point-of-birth testing instrument. Moreover, the step of collecting sample fluid from a newborn of the method of the present invention may include the steps of removing a cover of an input well in the biochemical cartridge, inserting a volume of sample fluid, and sealing the input well.

In an embodiment of the method for using a point-of-birth newborn screening system, the method may further include the step of distributing the test results. Moreover, in one embodiment of the method for using a point-of-birth newborn screening system, the method may include the step of interfacing with the software application of the smart display to review prior run test results.

BRIEF DESCRIPTION OF THE DRAWINGS

Figure 1:
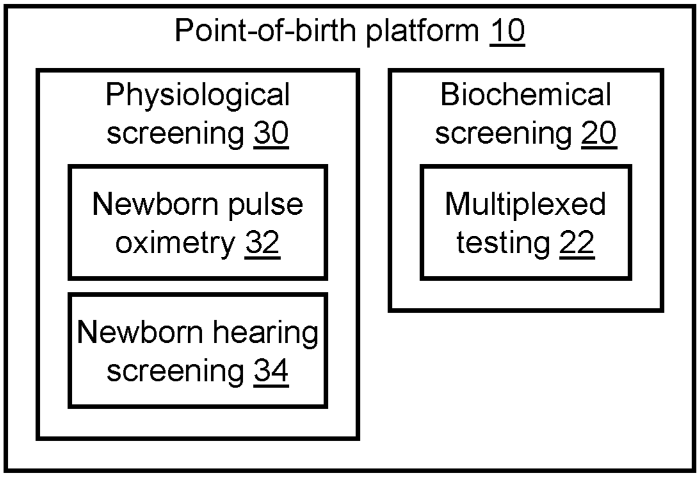
Figure 2A:
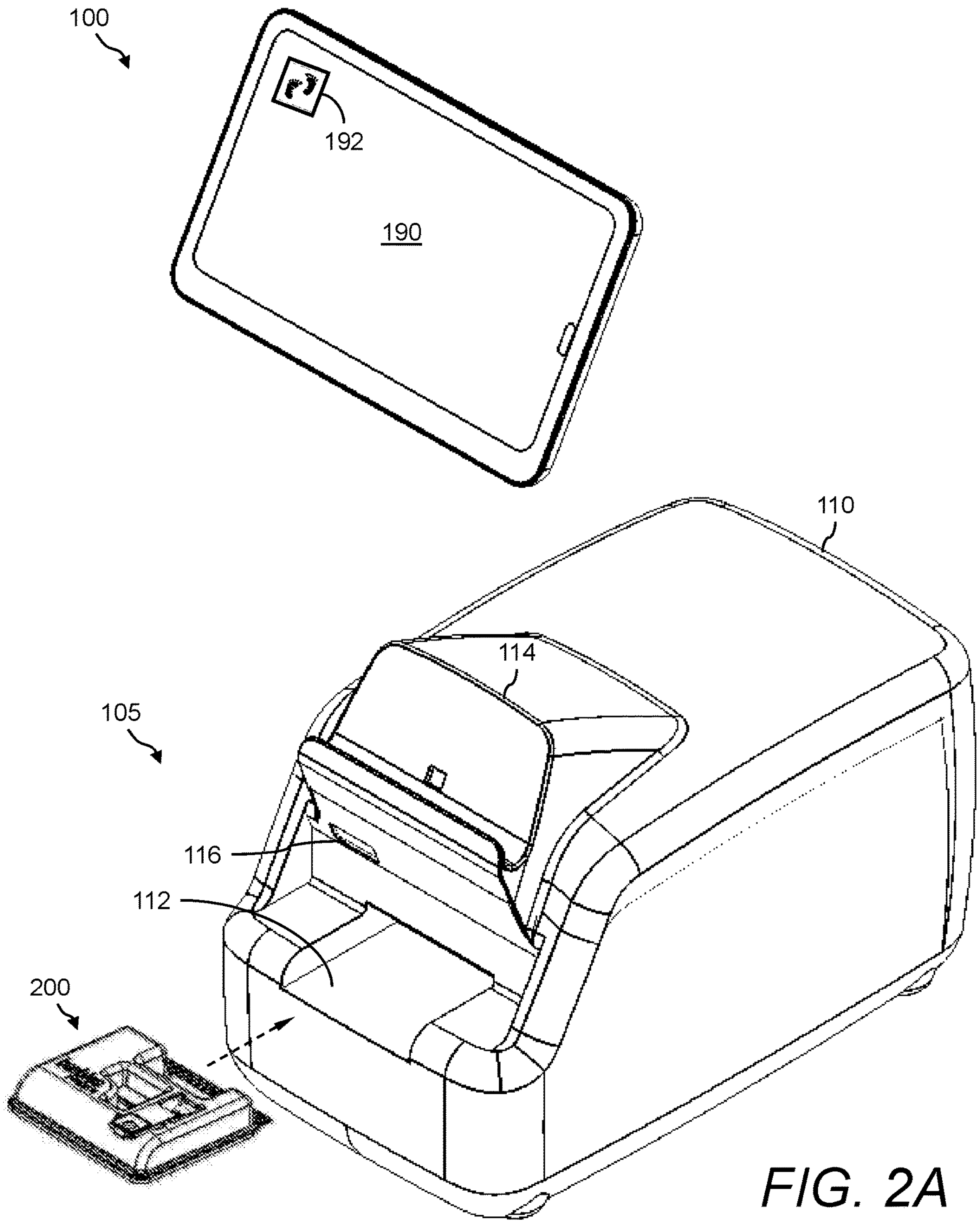
Figure 2B:
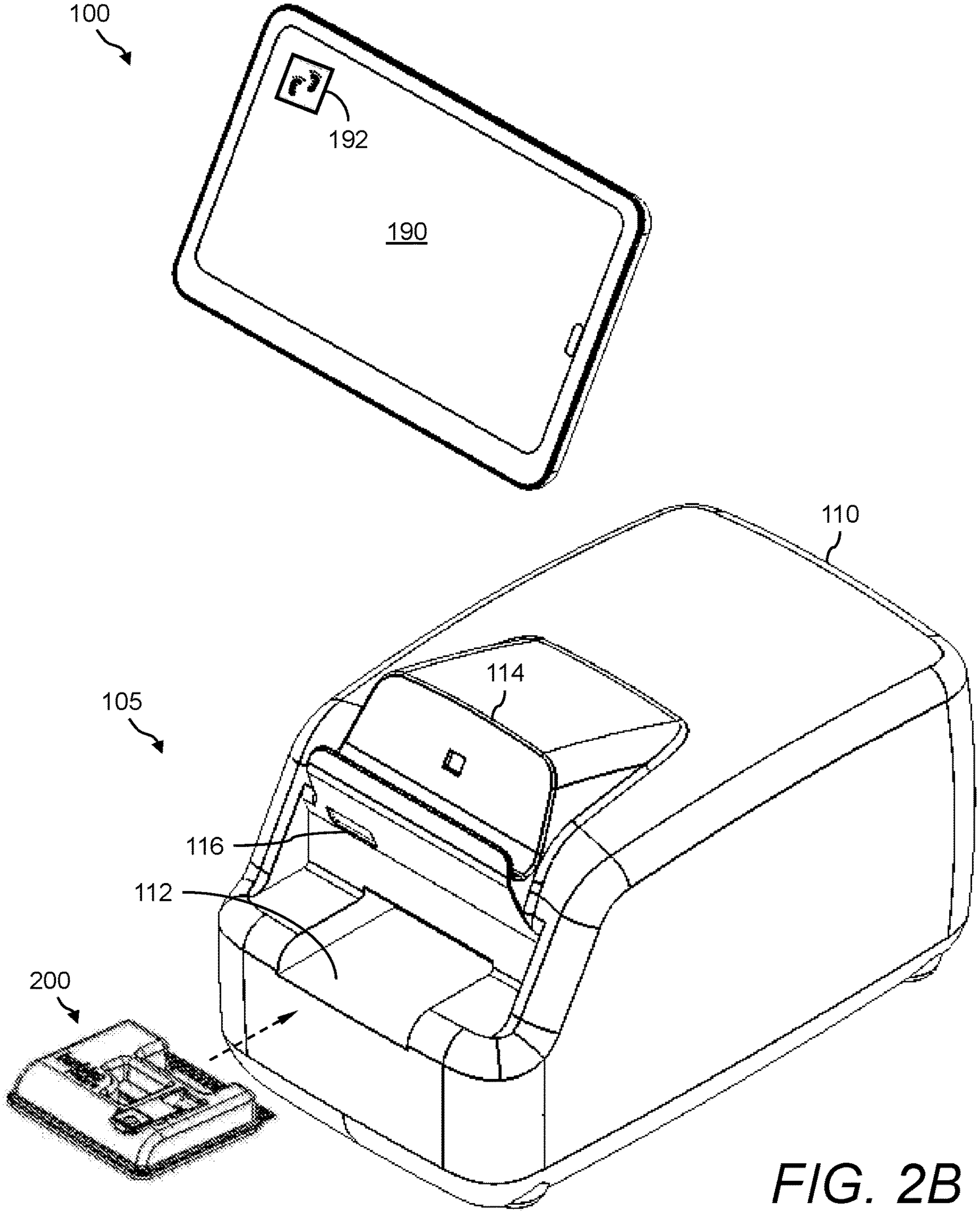
Figure 3A:
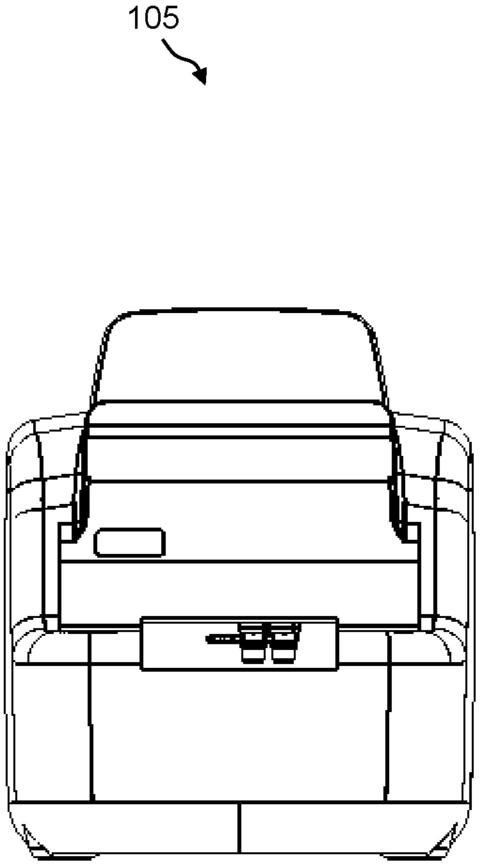
Figure 3B:
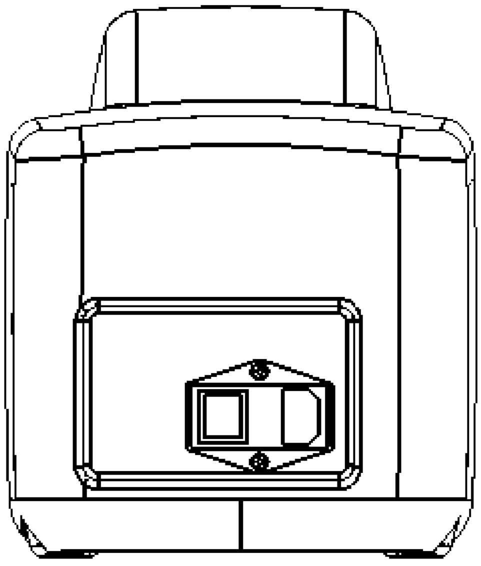
Figure 3C:
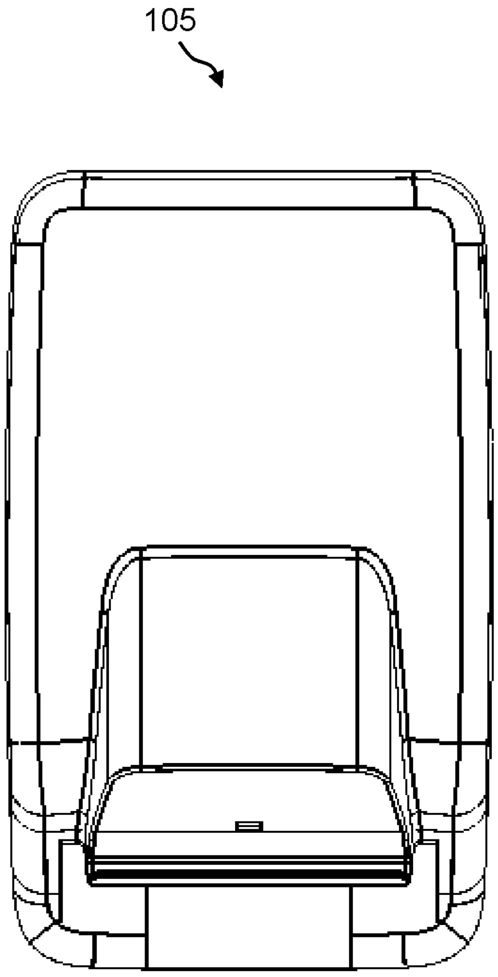
Figure 3D:
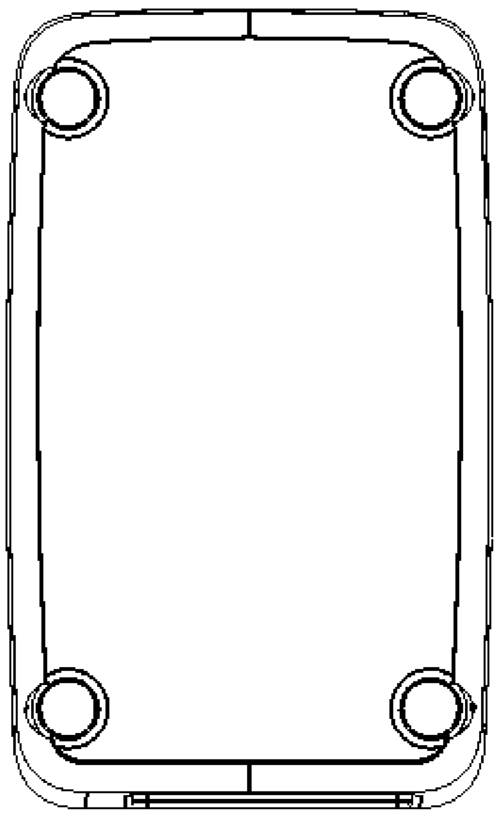
Figure 3E:
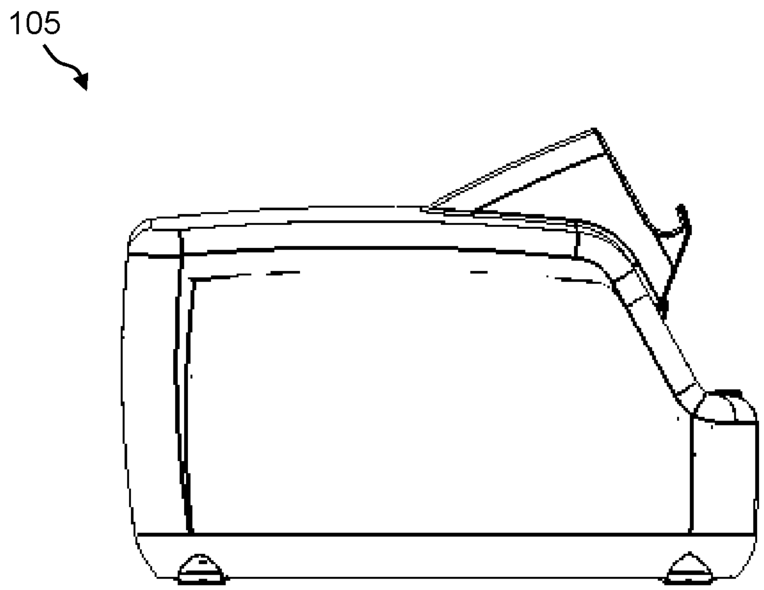
Figure 3F:
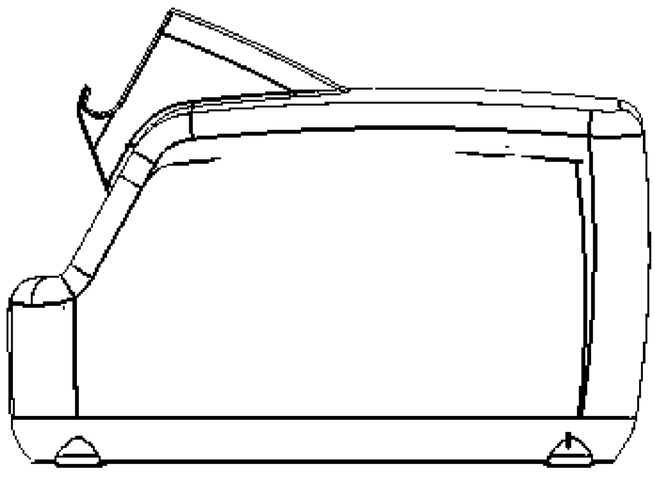
Figure 4:
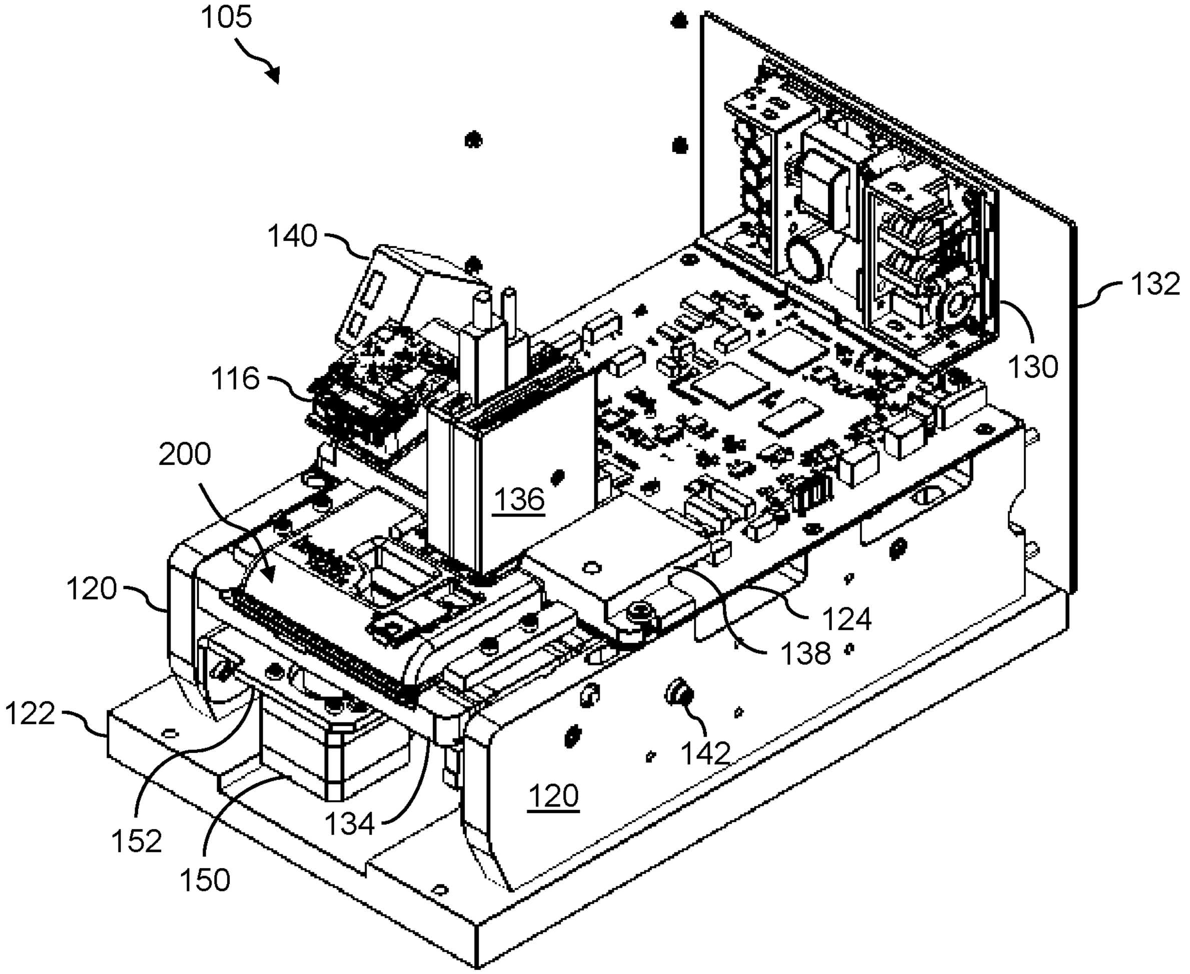
Figure 5:
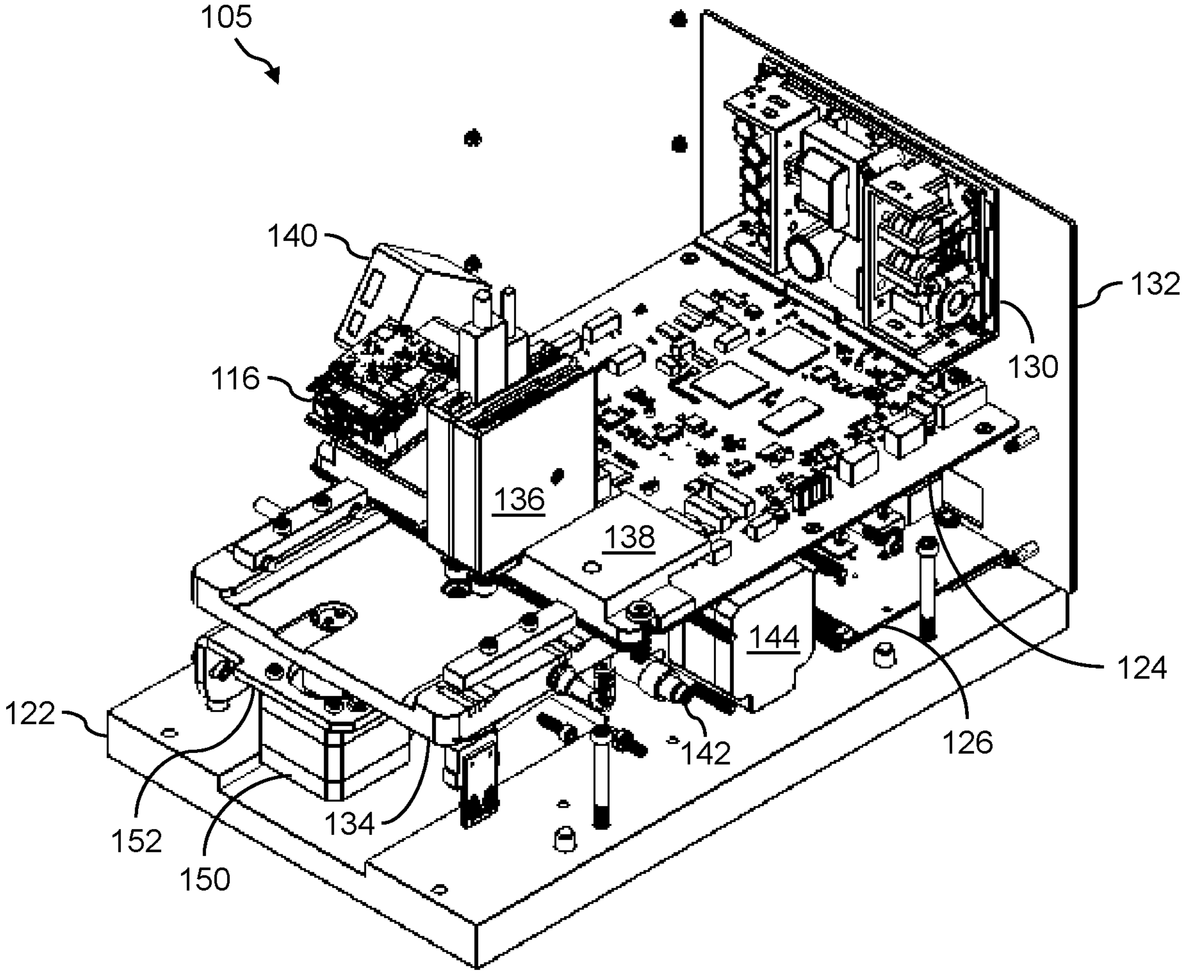
Figure 6:
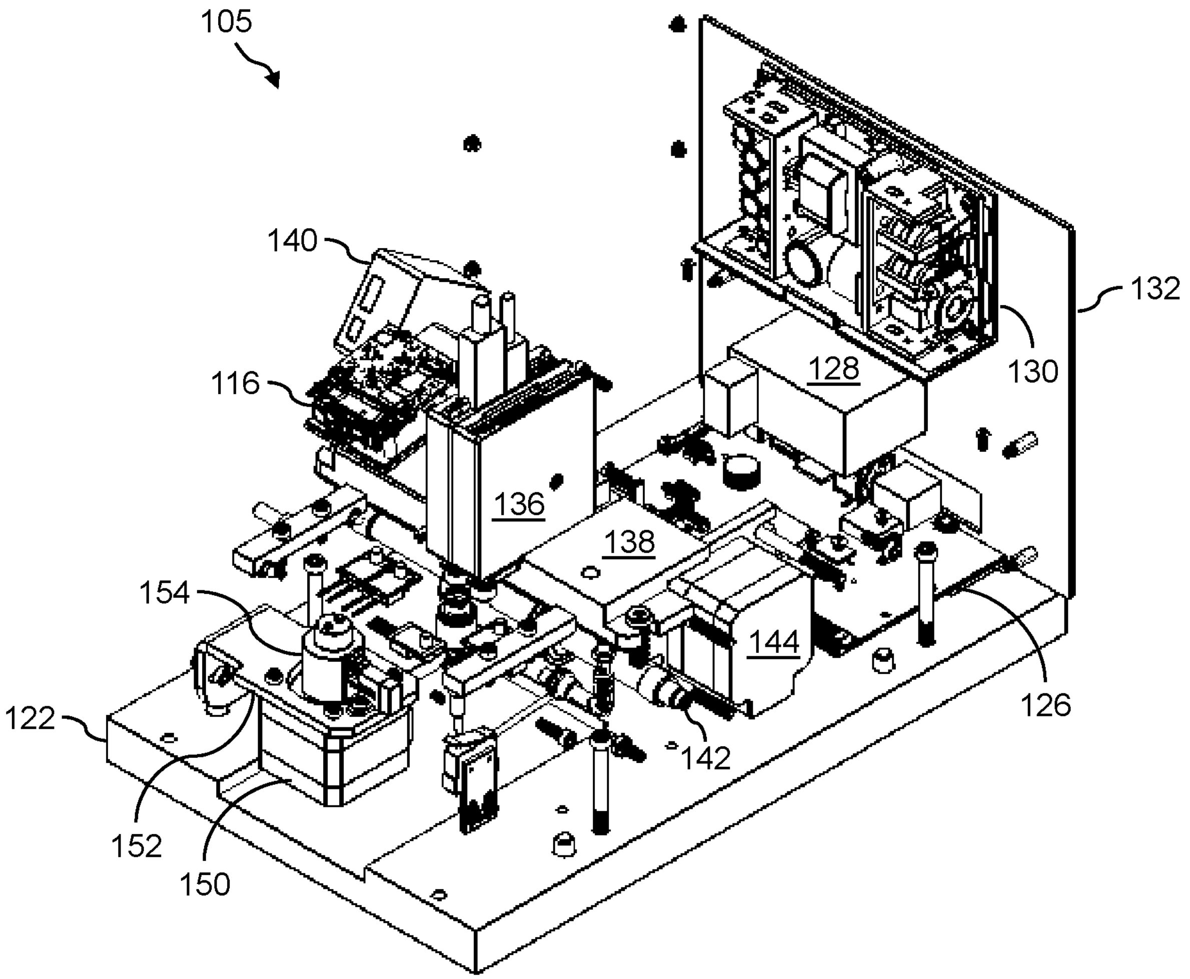
Figure 7:
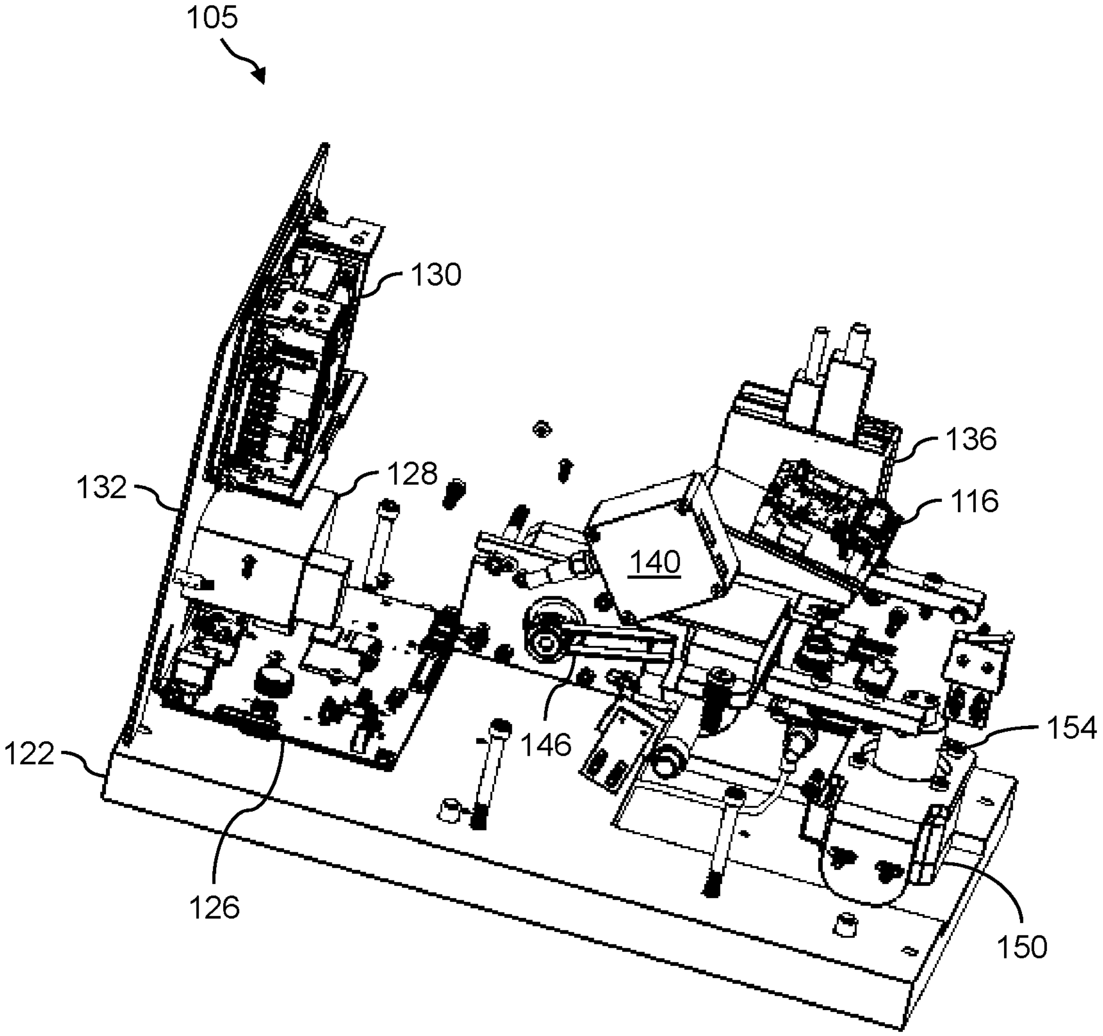
Figure 8A:
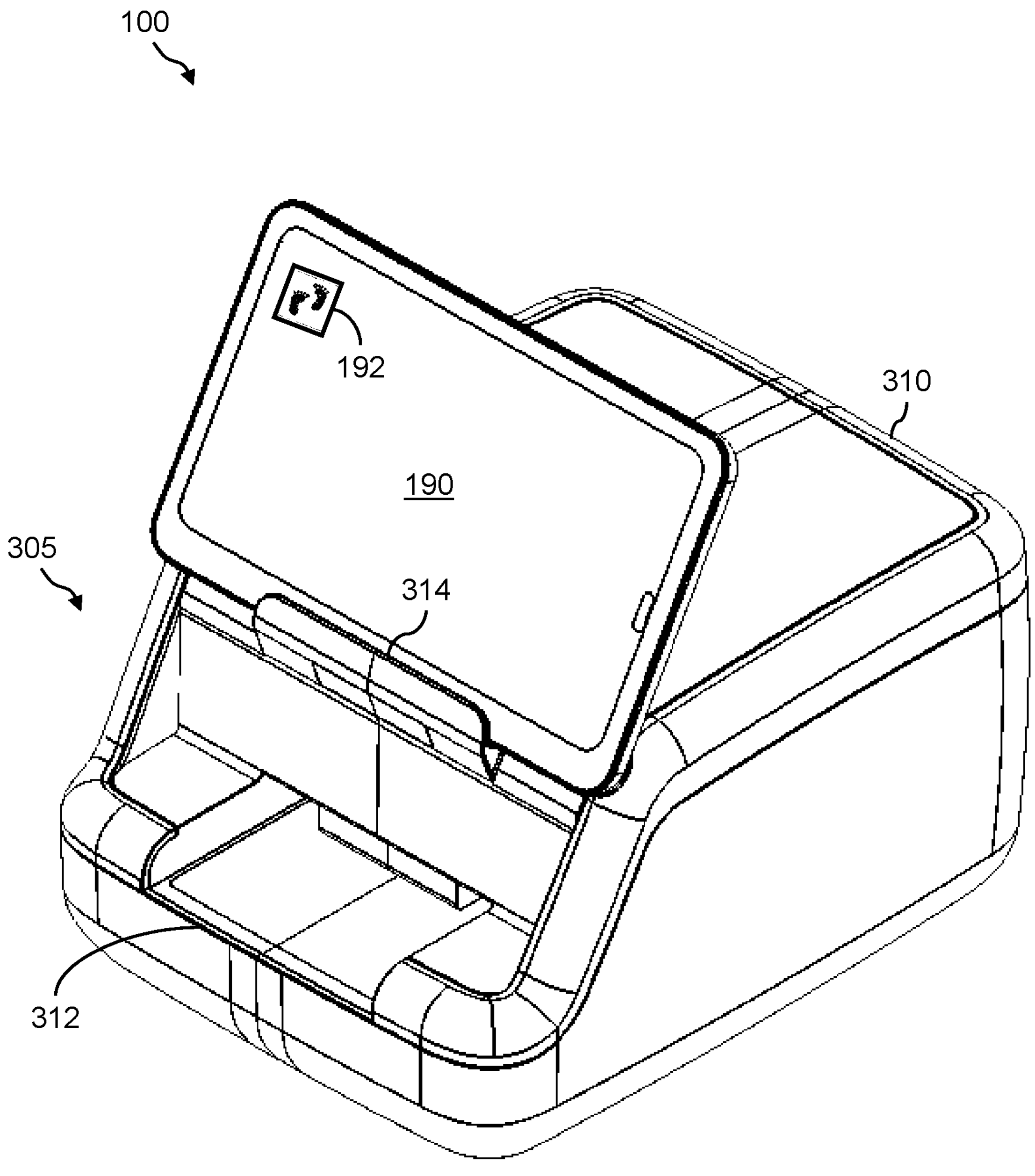
Figure 8B:
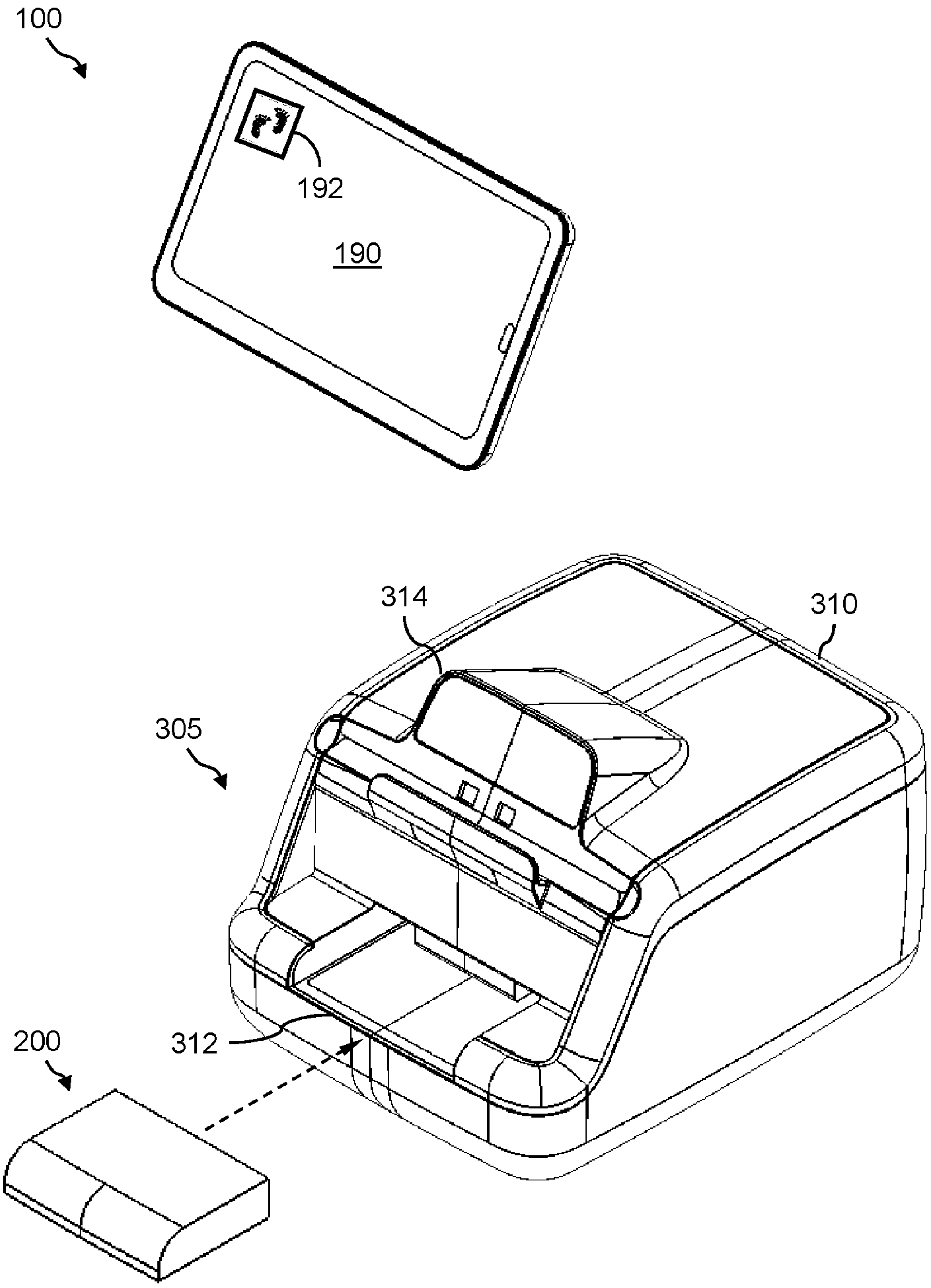
Figure 9A:
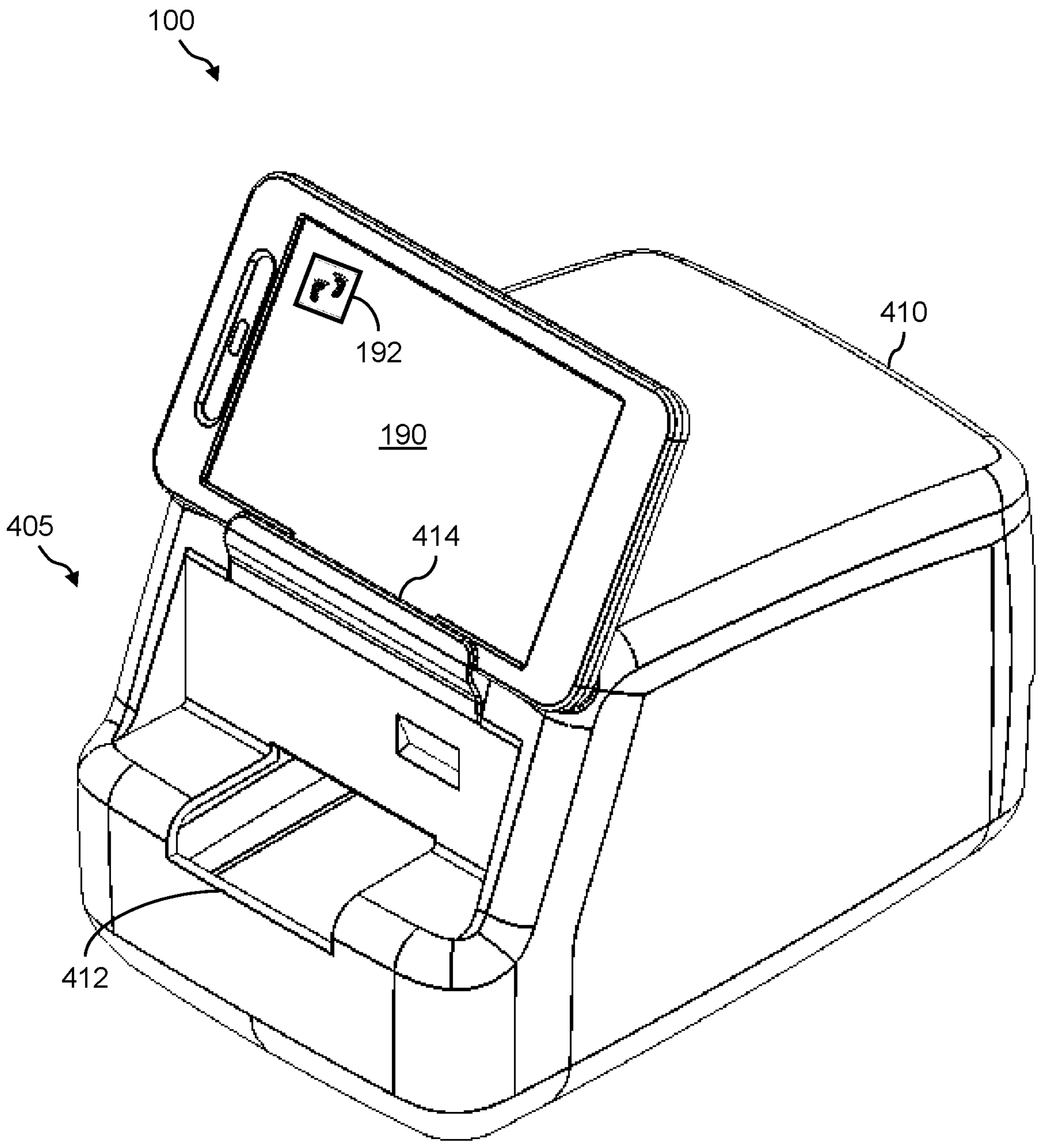
Figure 9B:
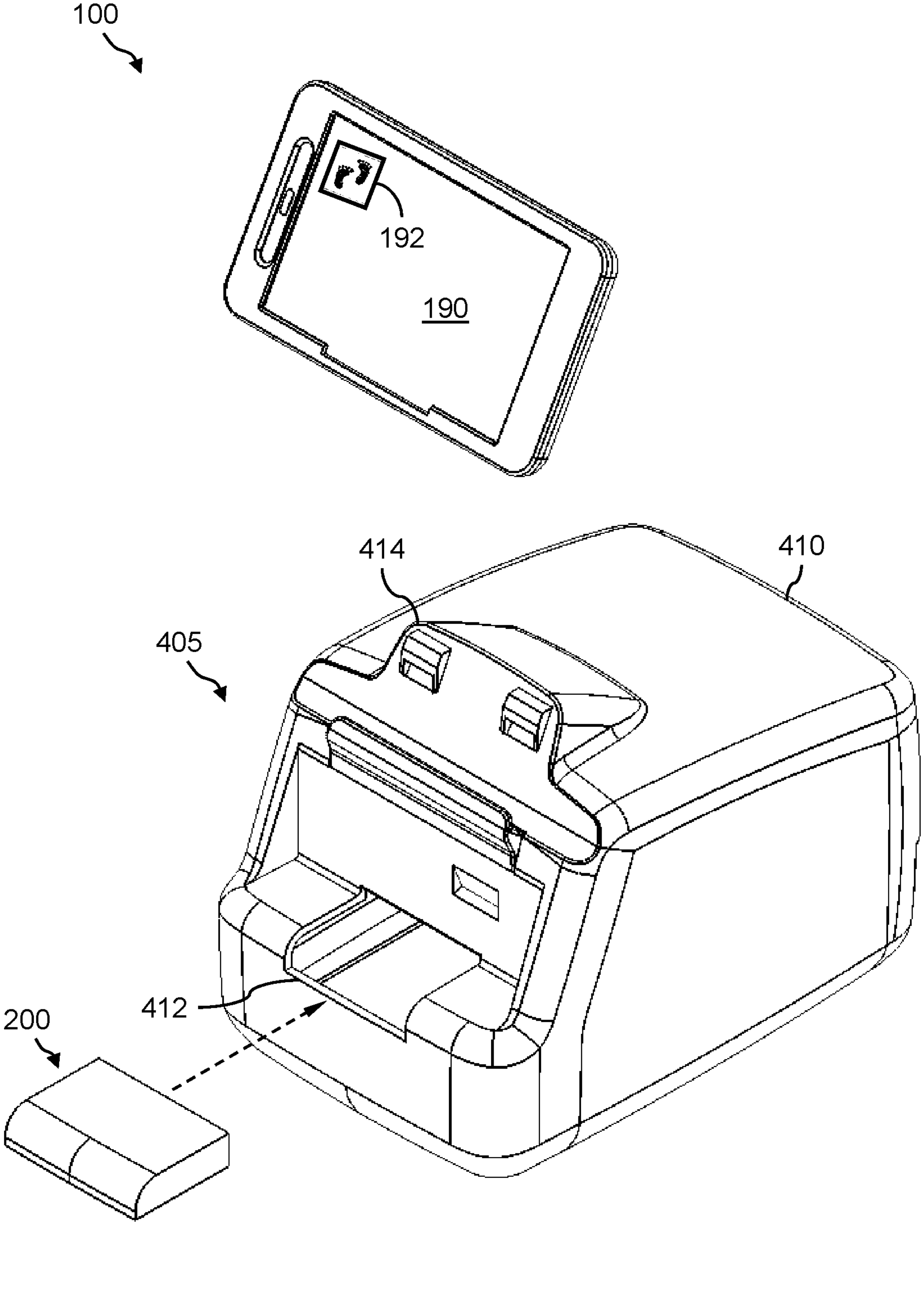
Figure 10A:
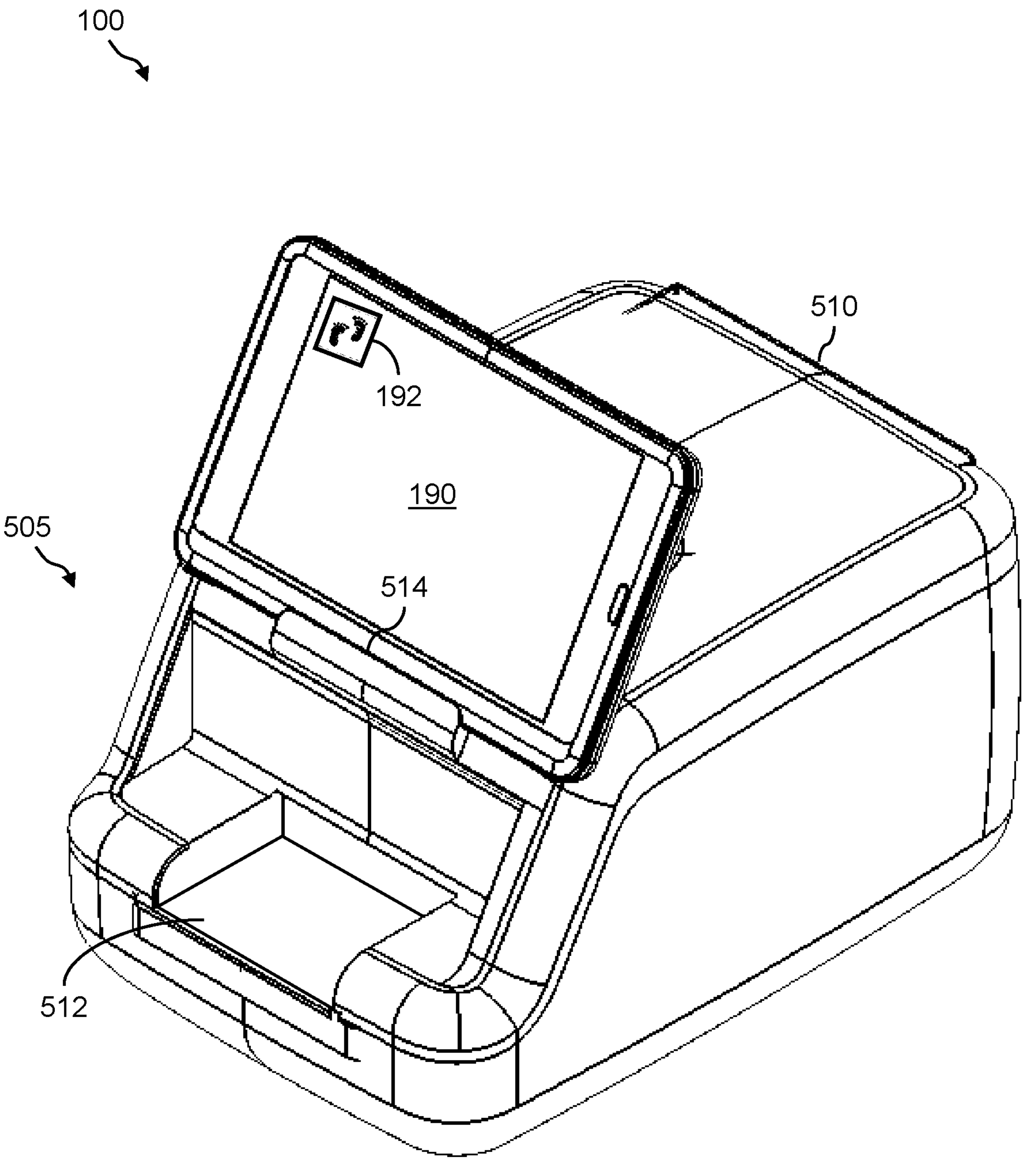
Figure 10B:
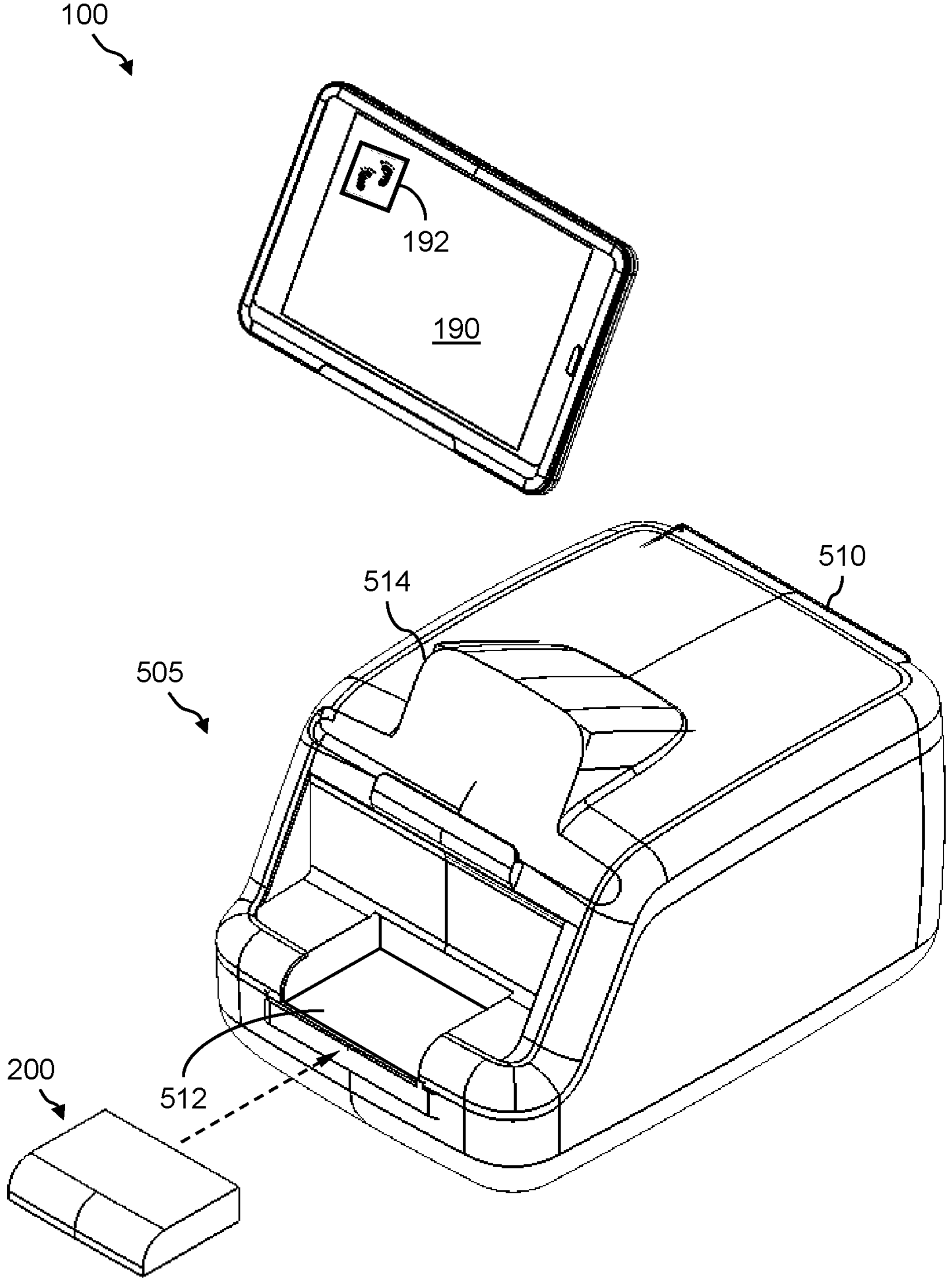
Figure 11:
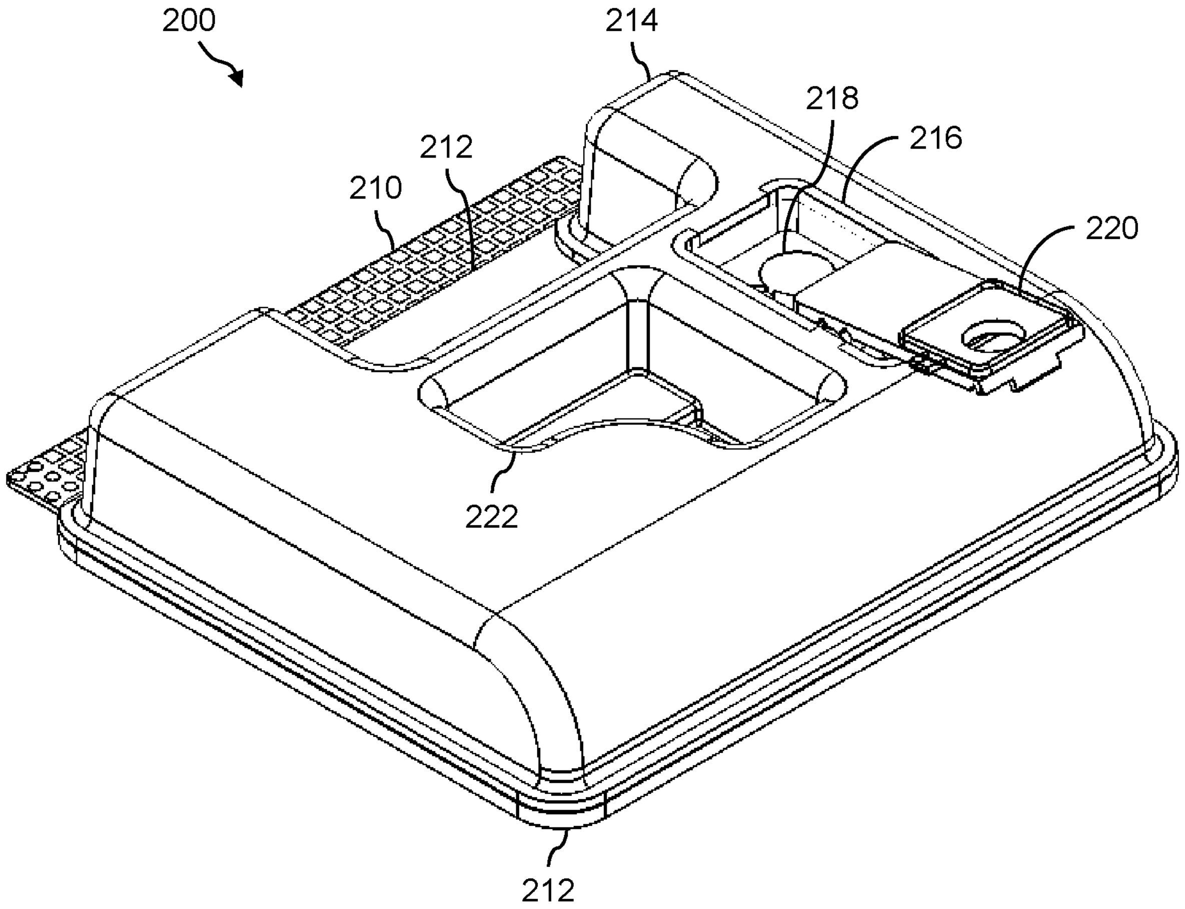
Figure 12:
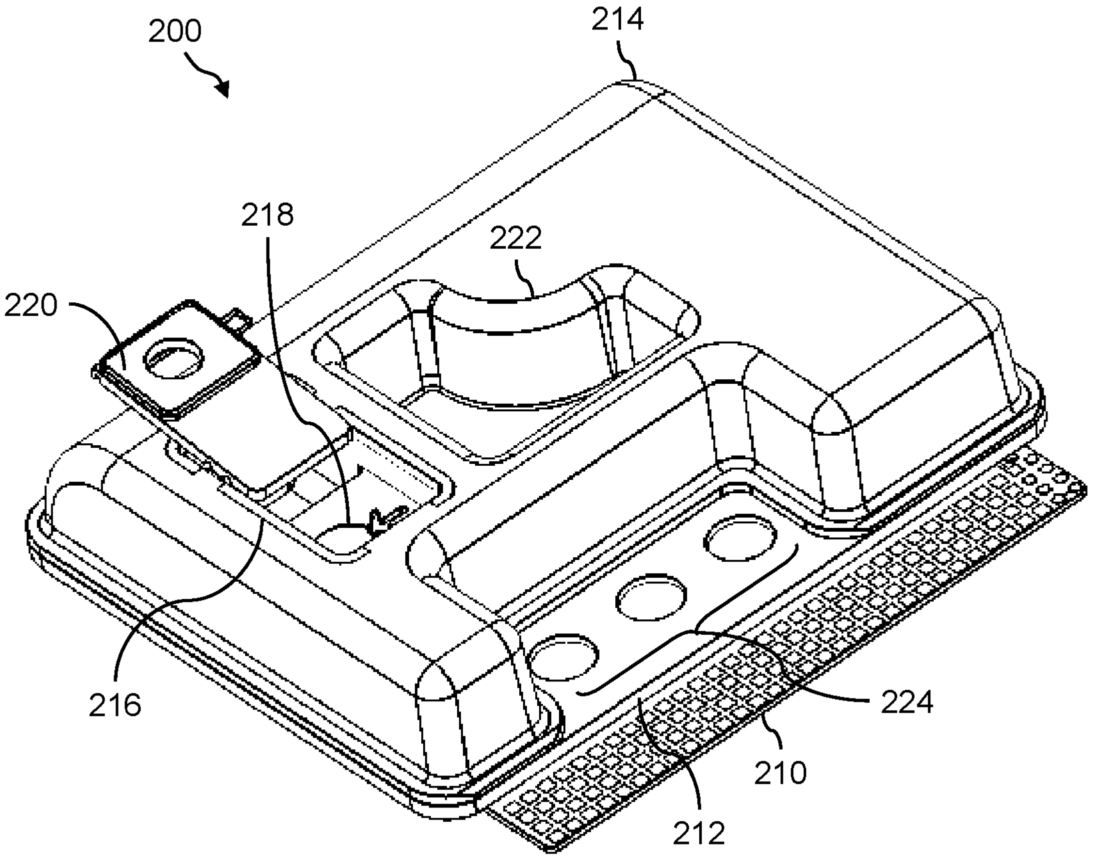
Figure 13:
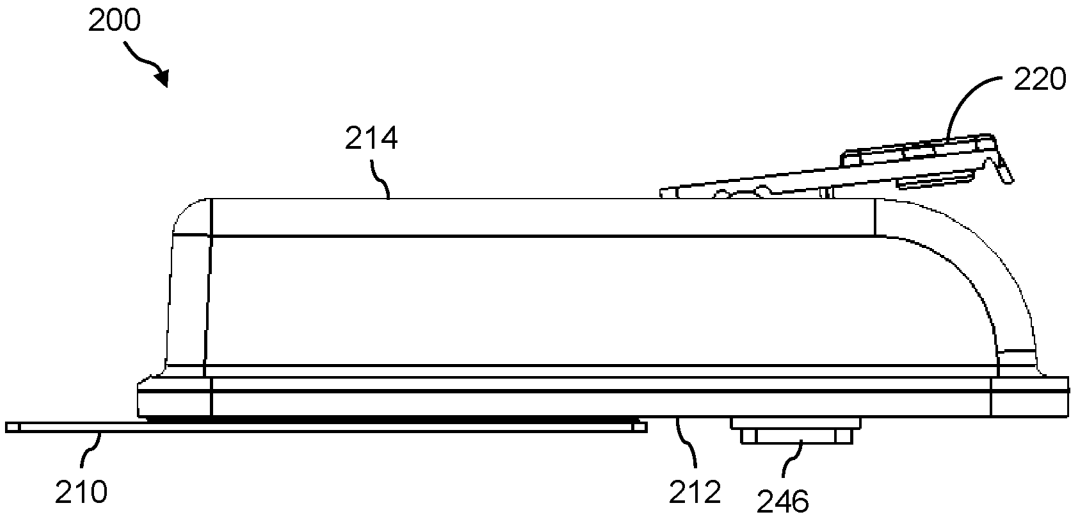
Figure 14:
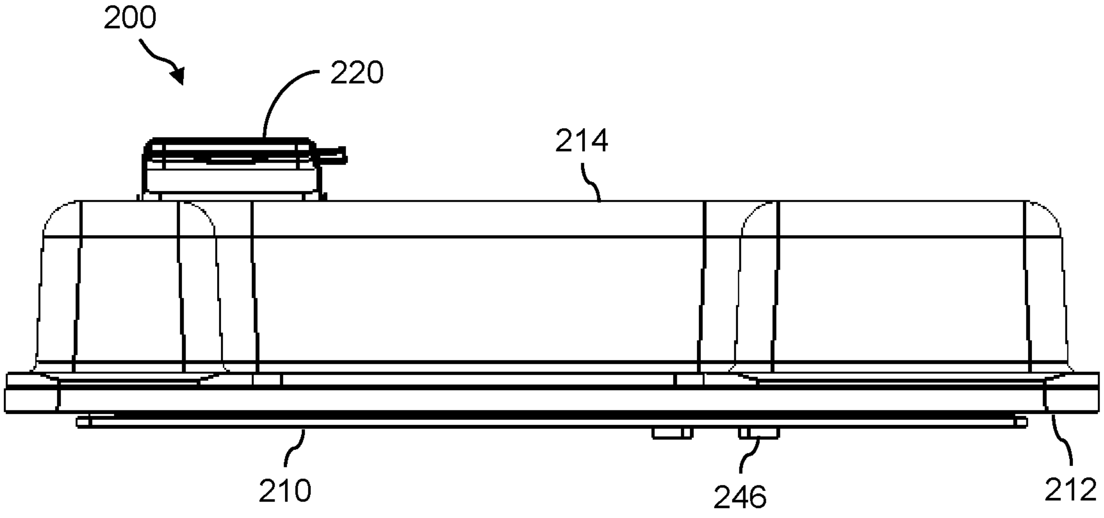
Figure 15:
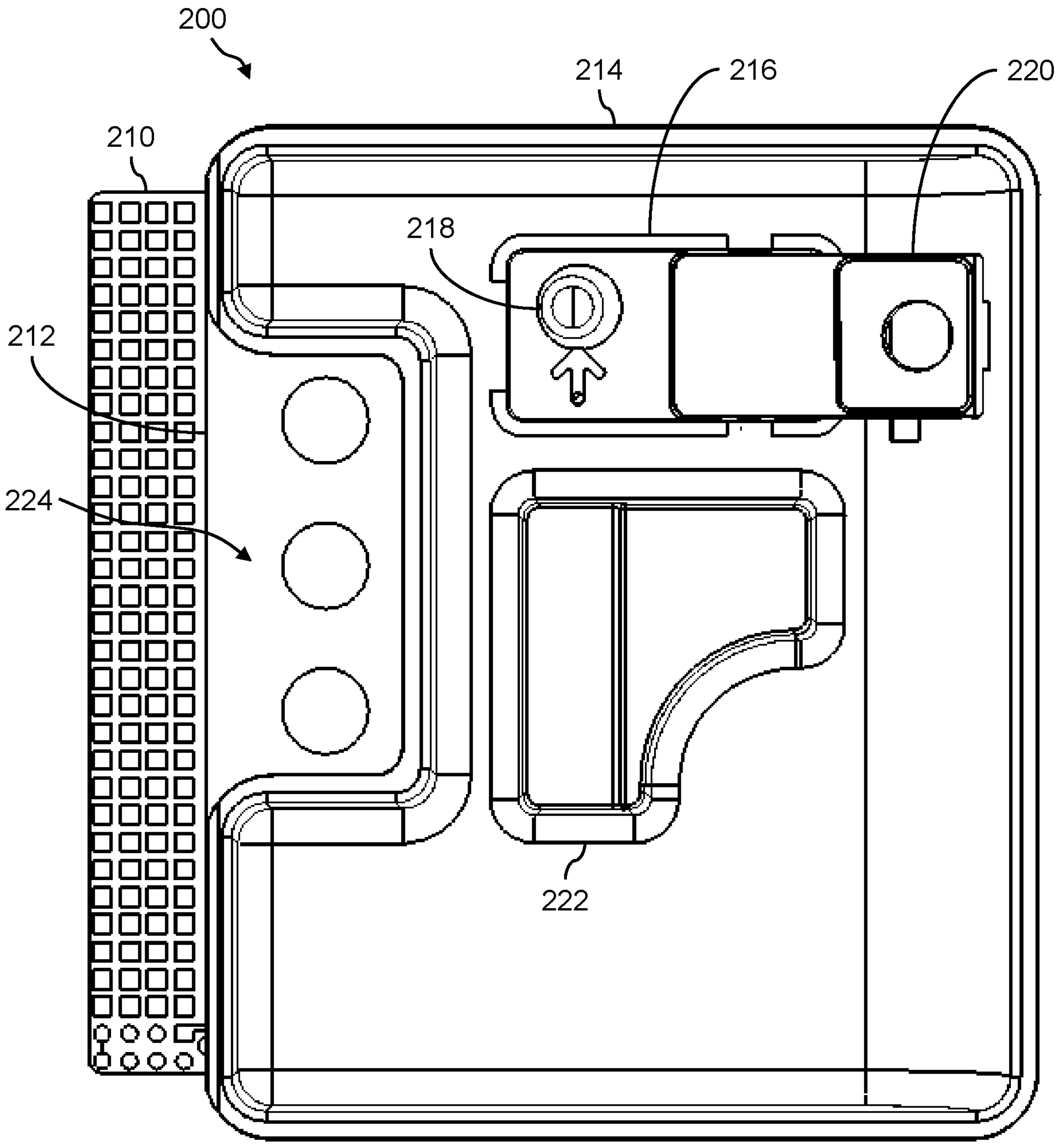
Figure 16:
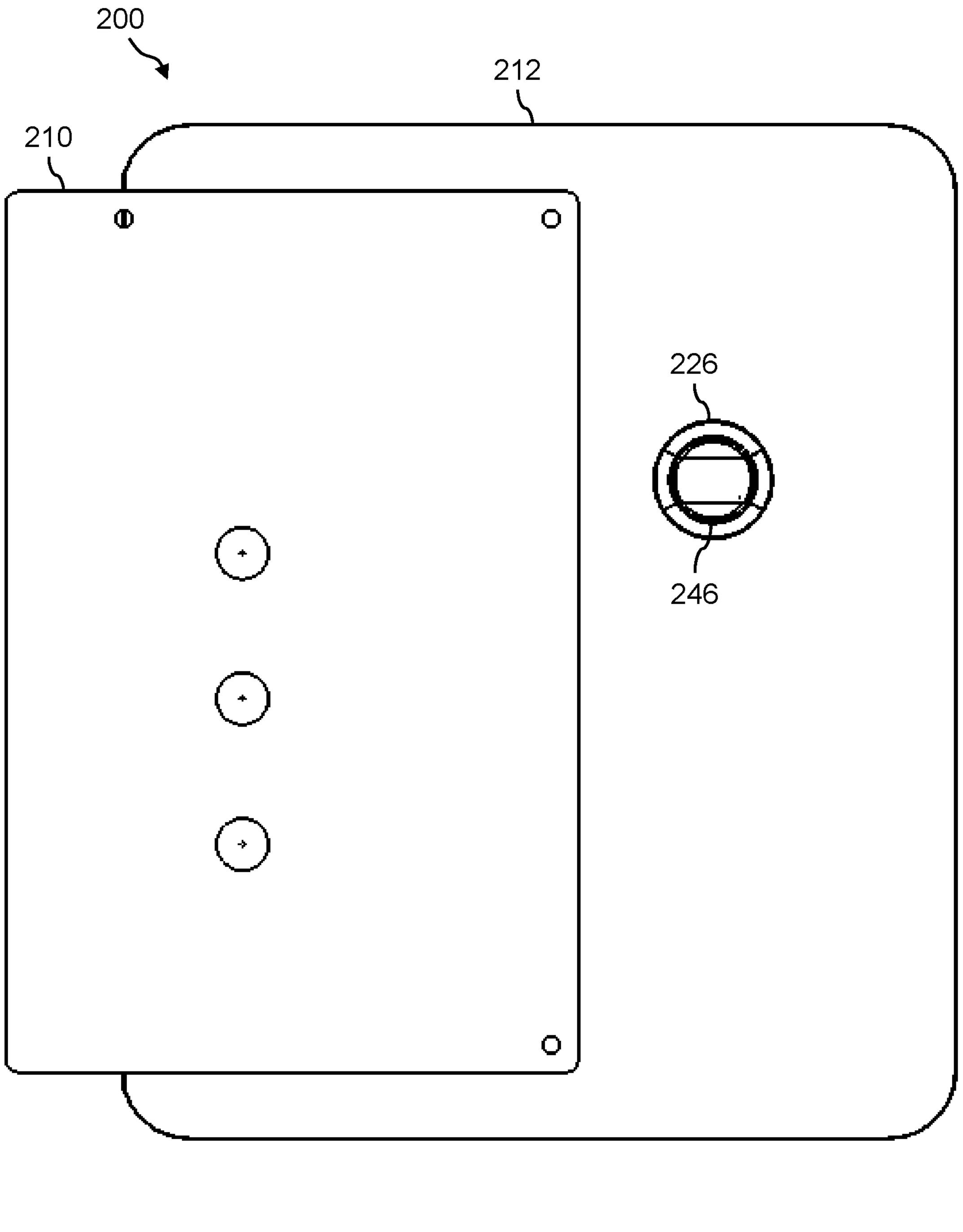
Figure 17:
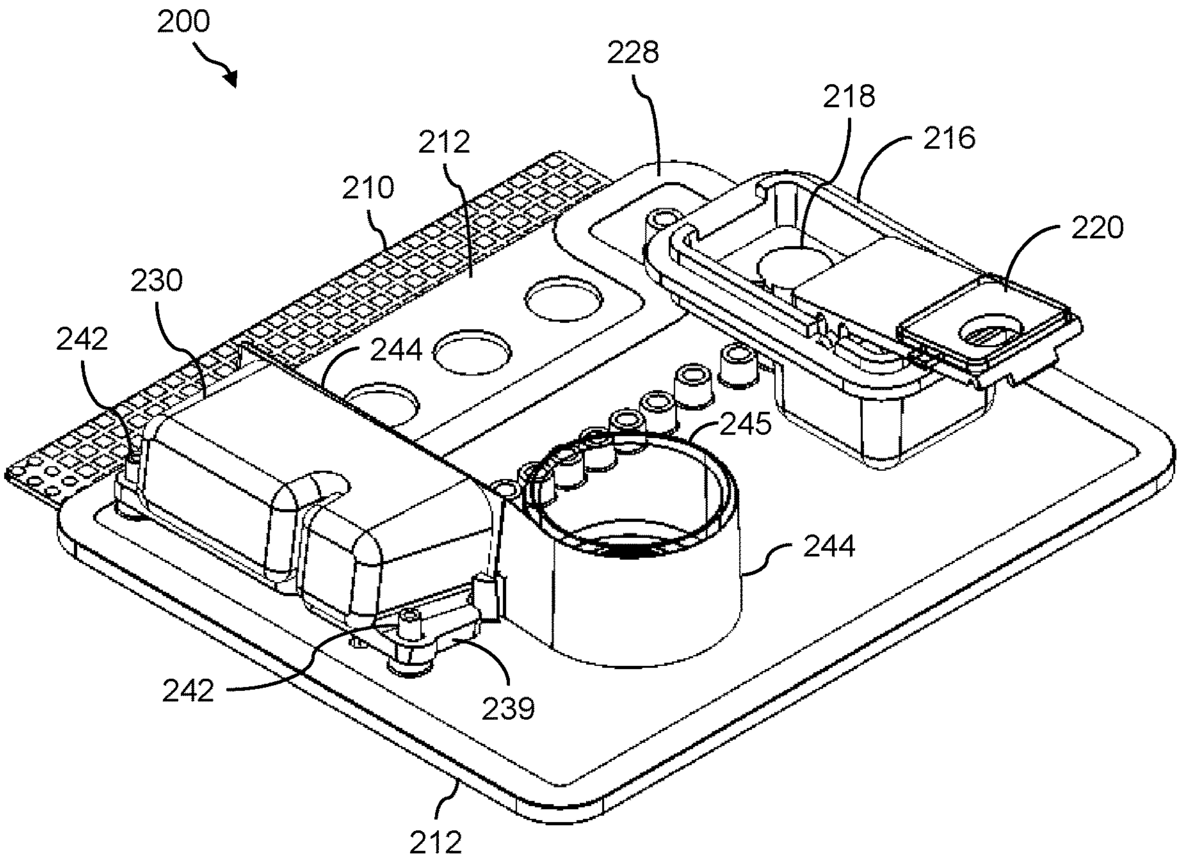
Figure 18:
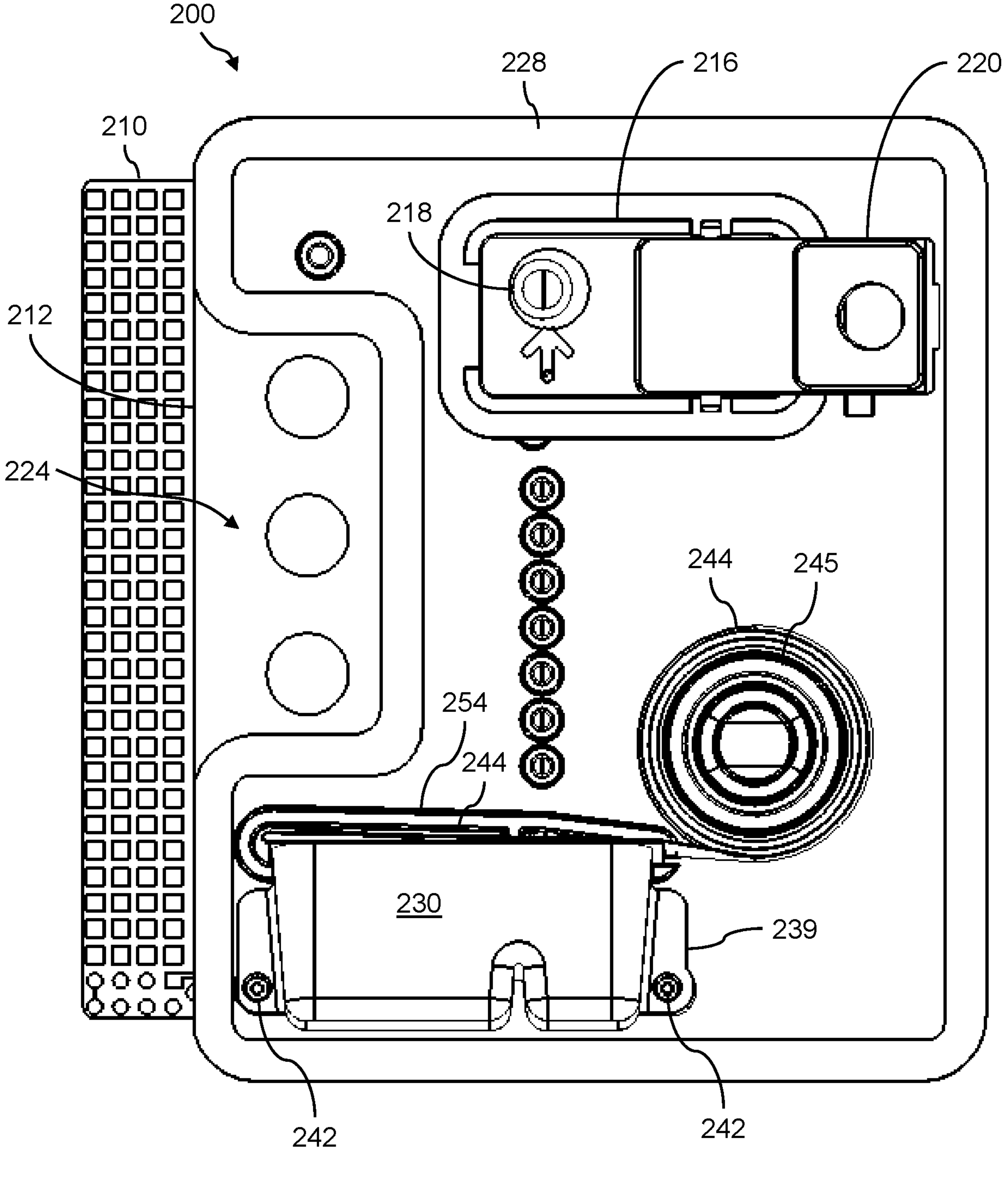
Figure 19:
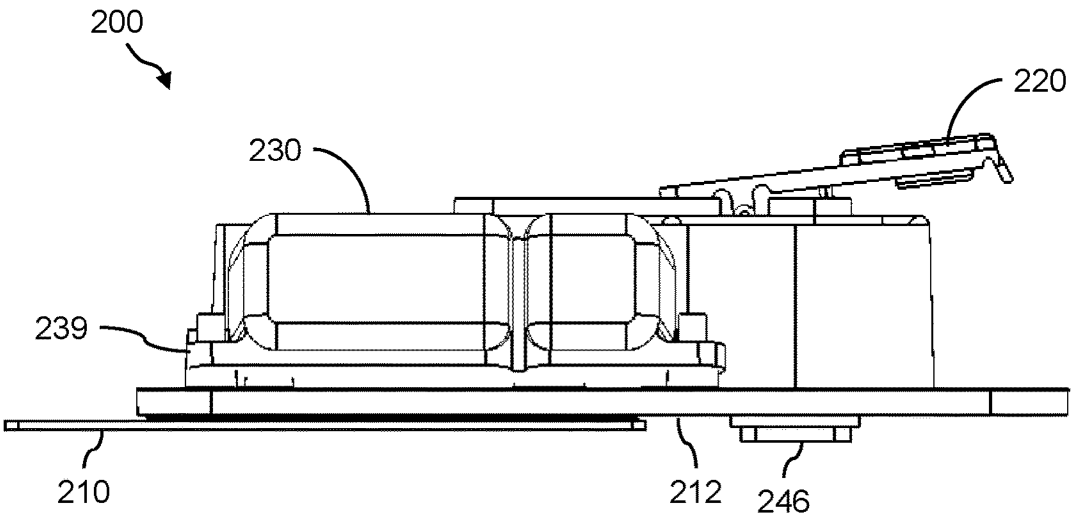
Figure 20:
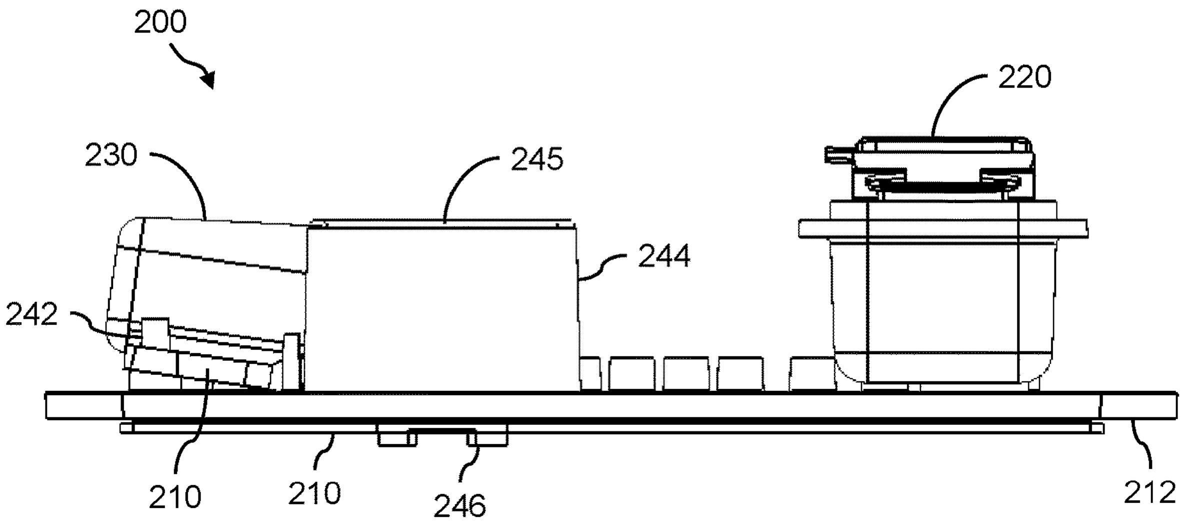
Figure 21:
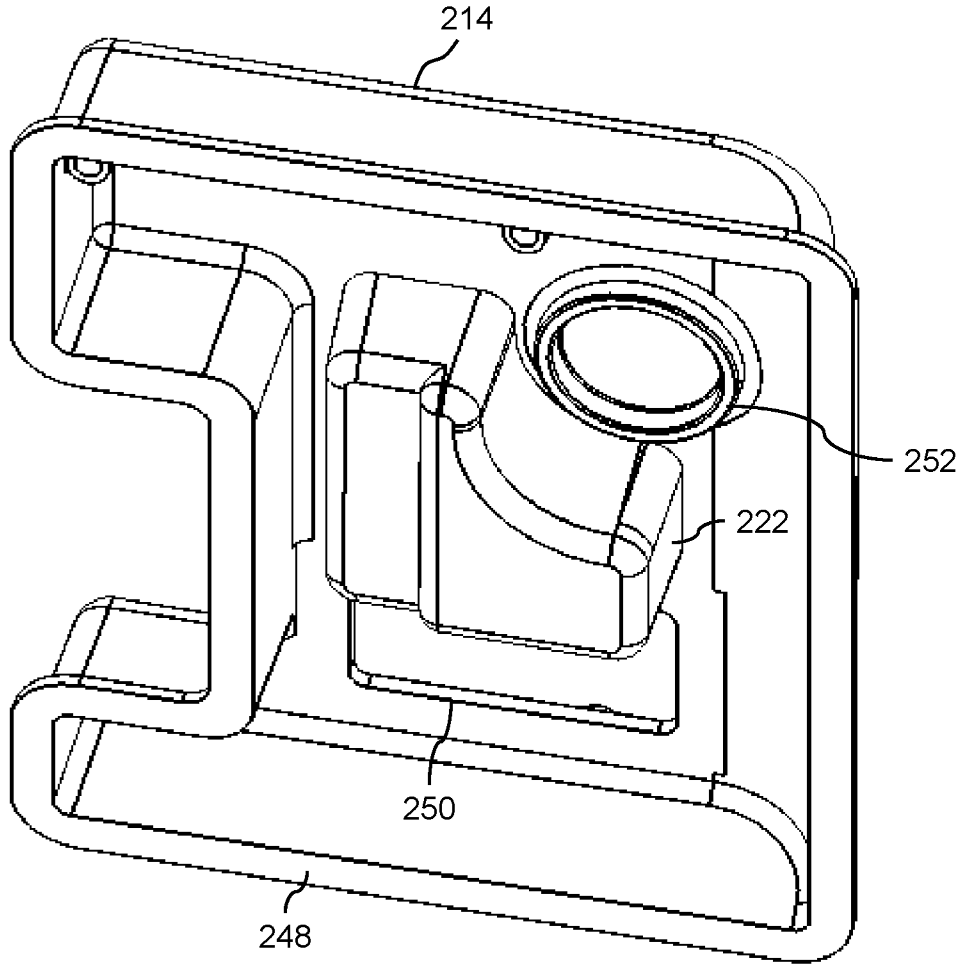
Figure 22A:
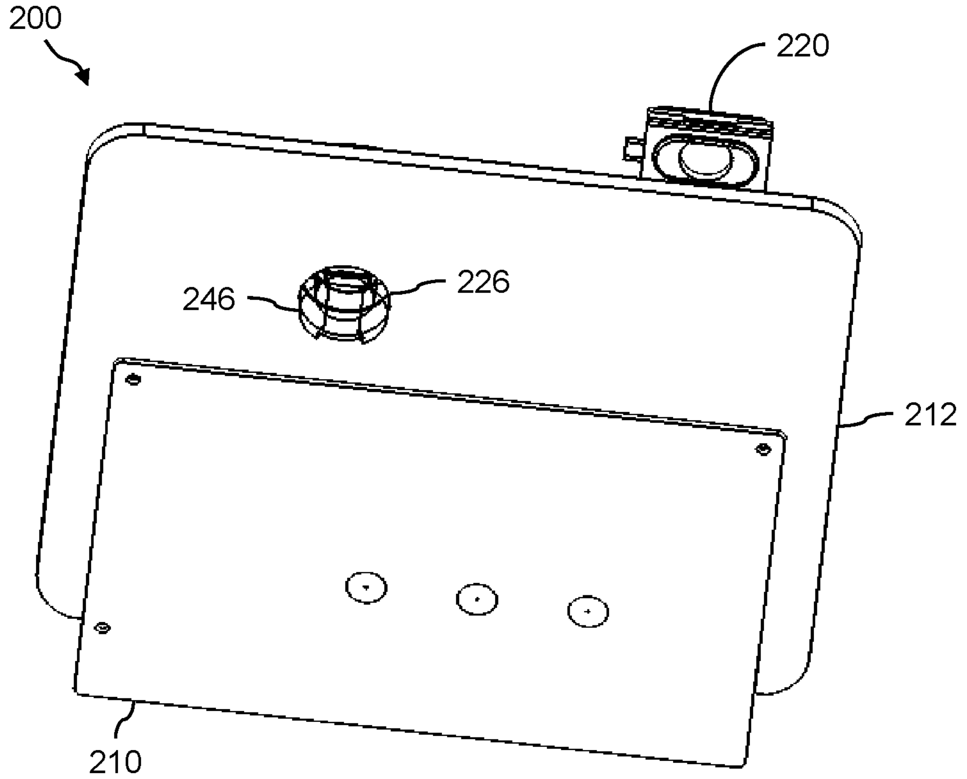
Figure 22B:
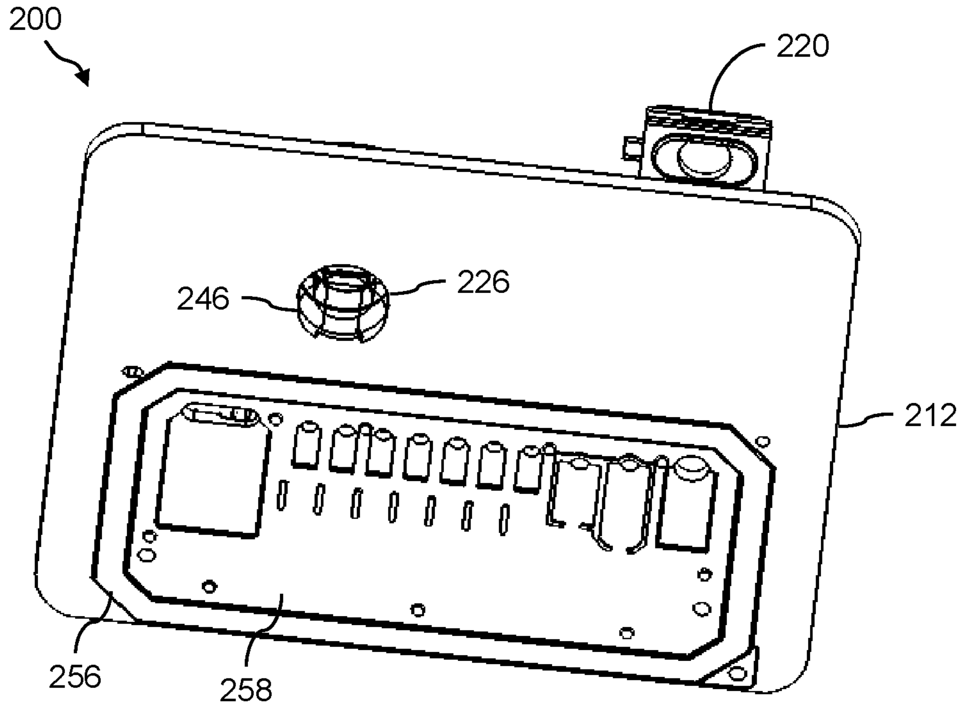
Figure 23A:
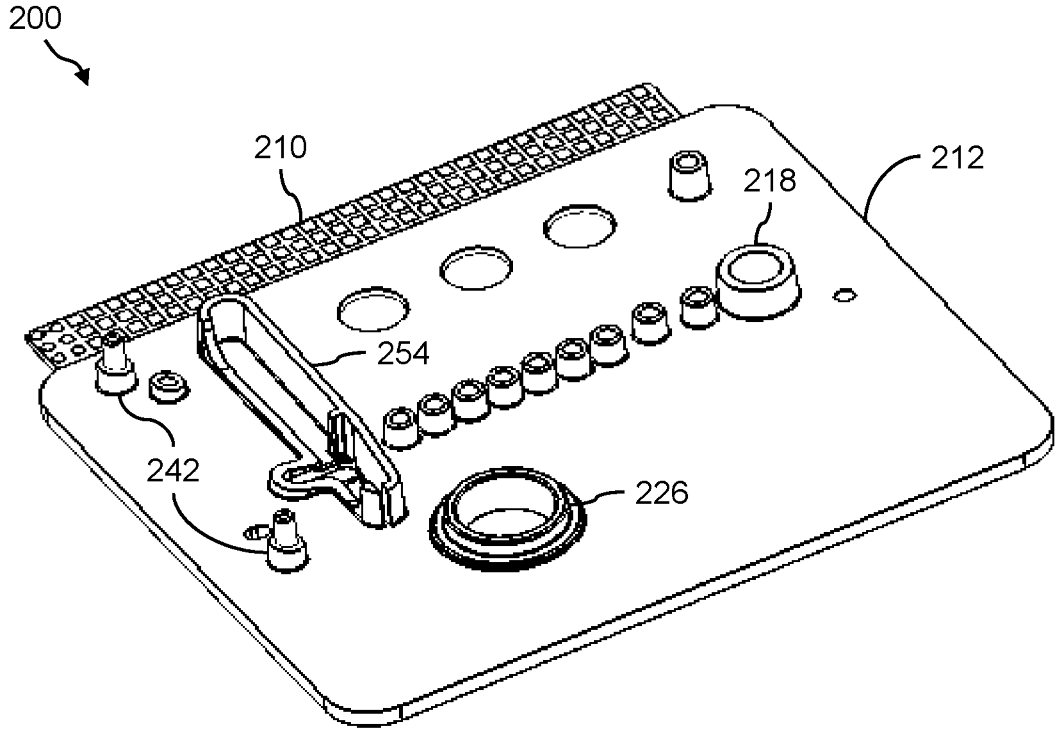
Figure 23B:
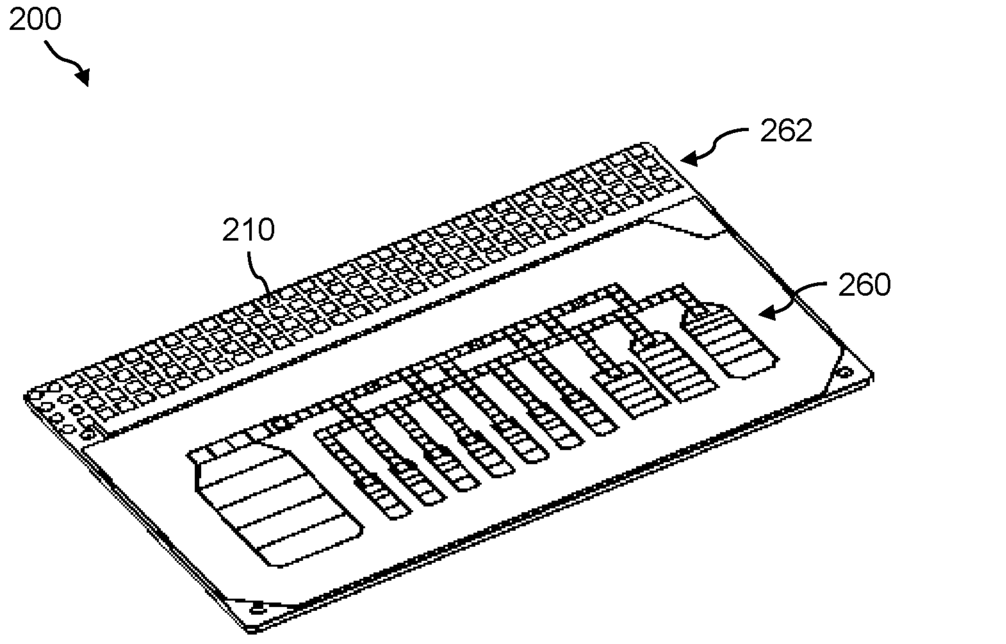
Figure 24A:
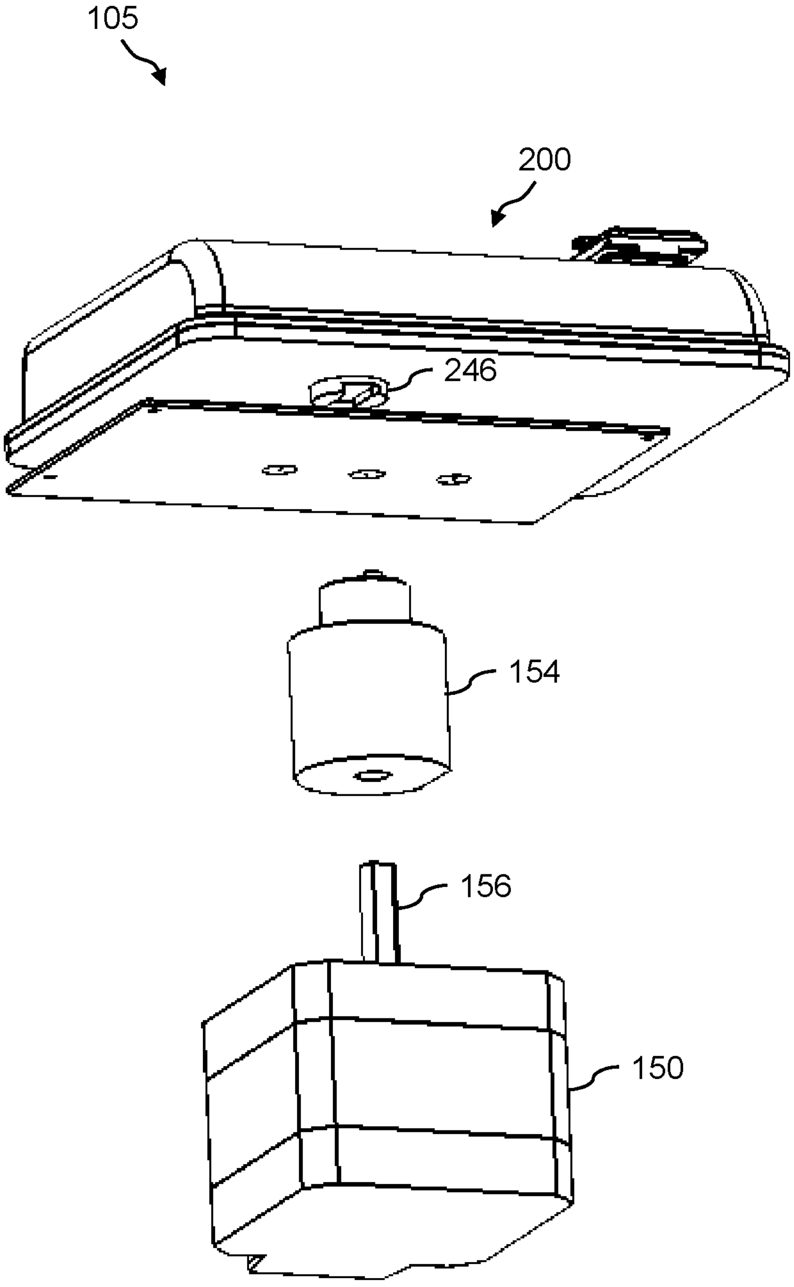
Figure 24B:
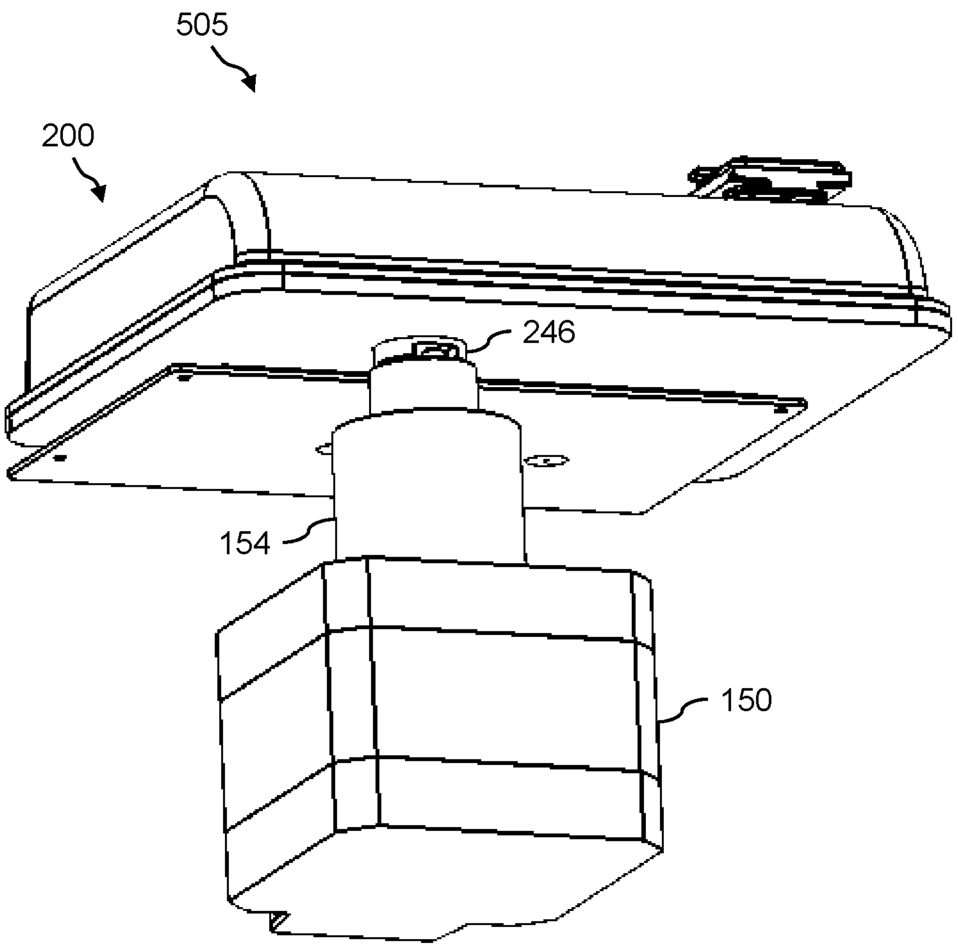
Figure 25:
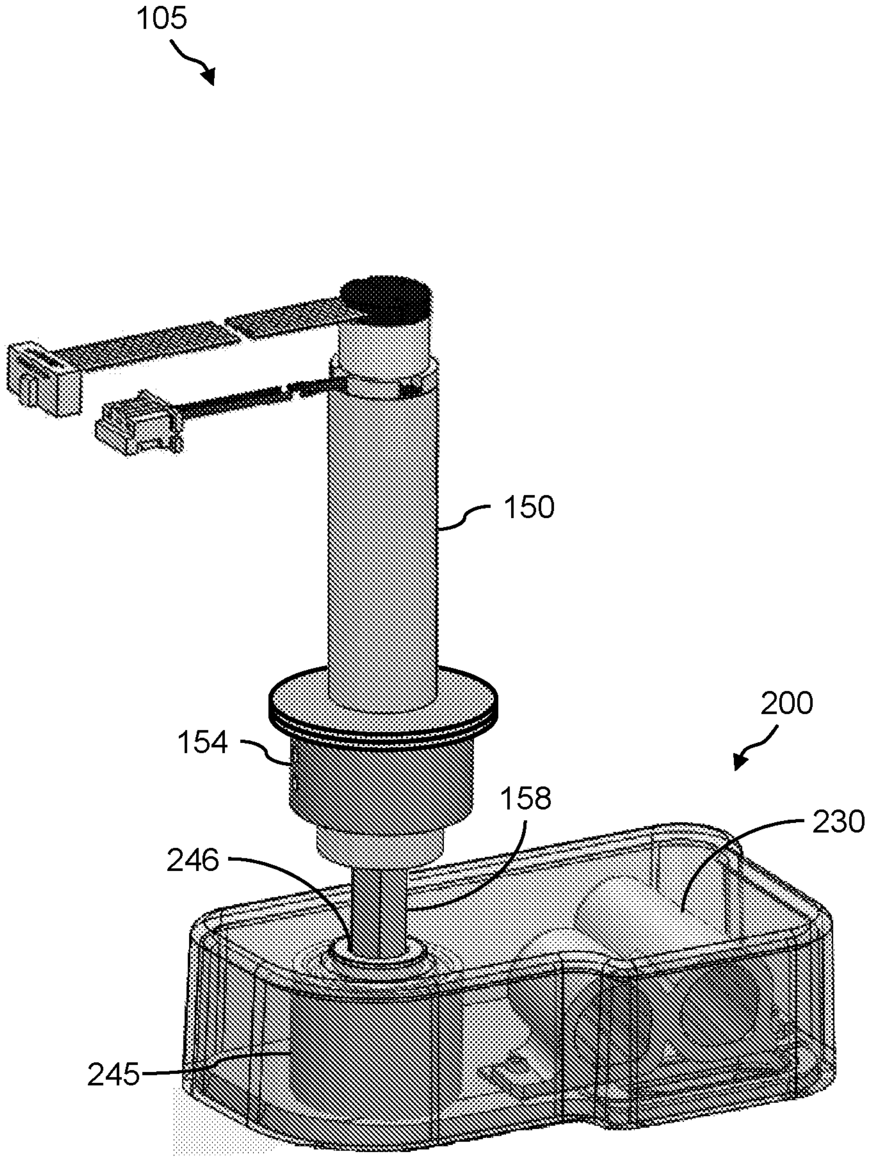
Figure 26:
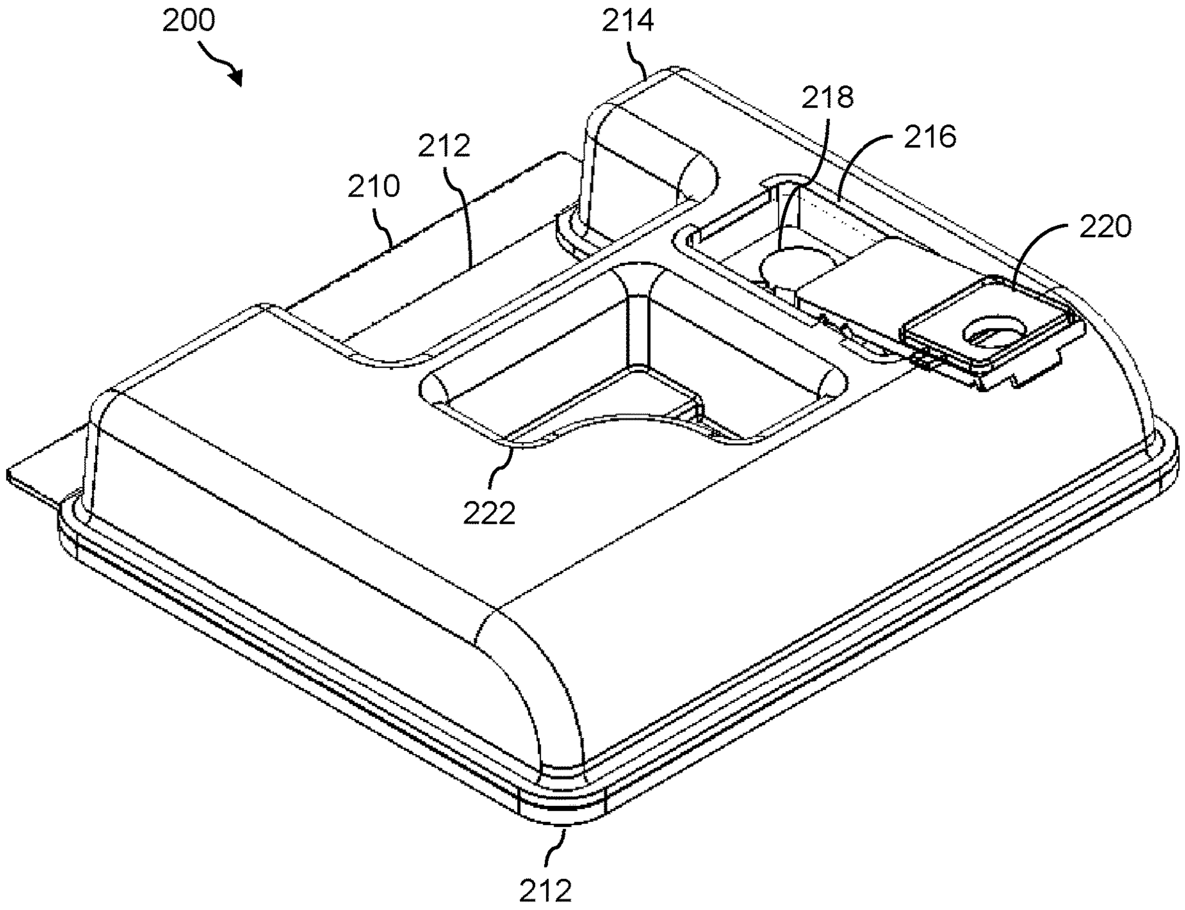
Figure 27:
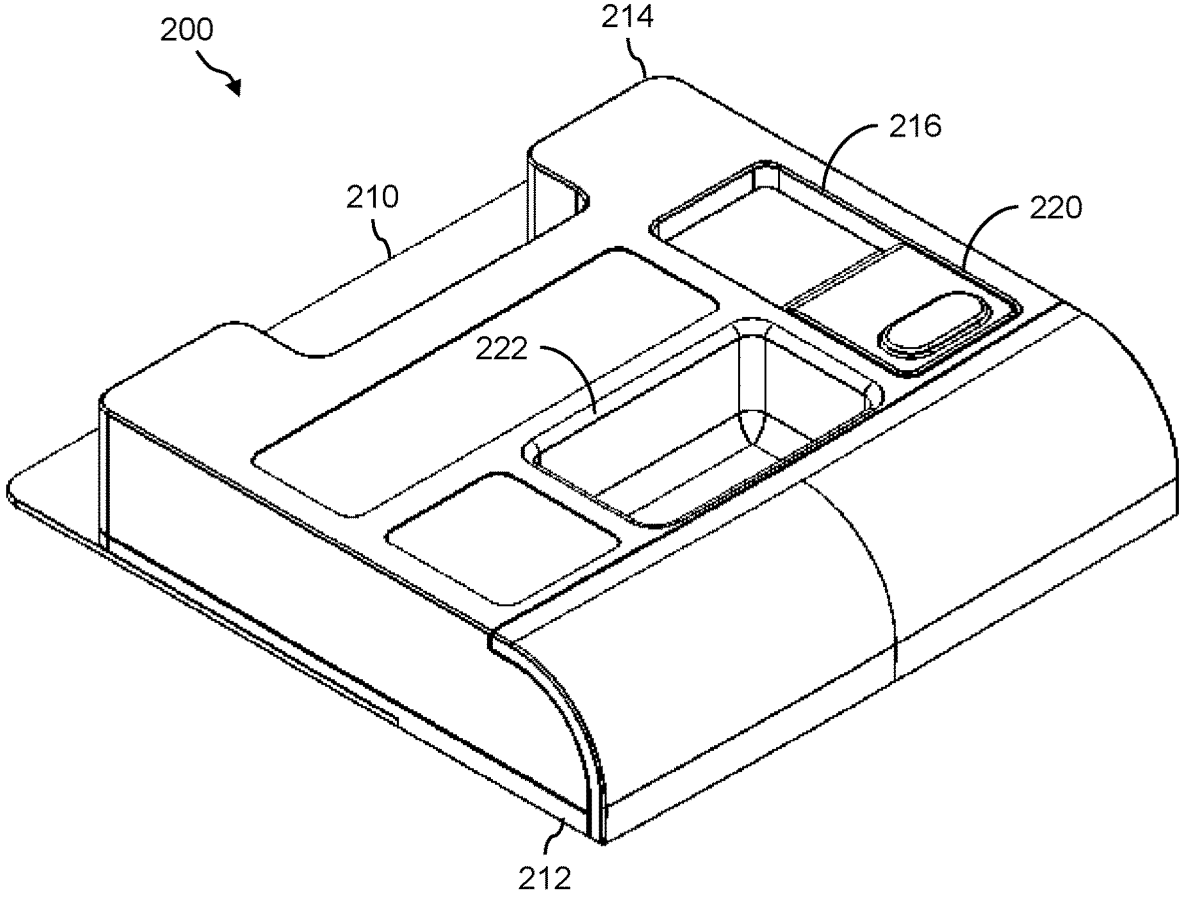
Figure 28:
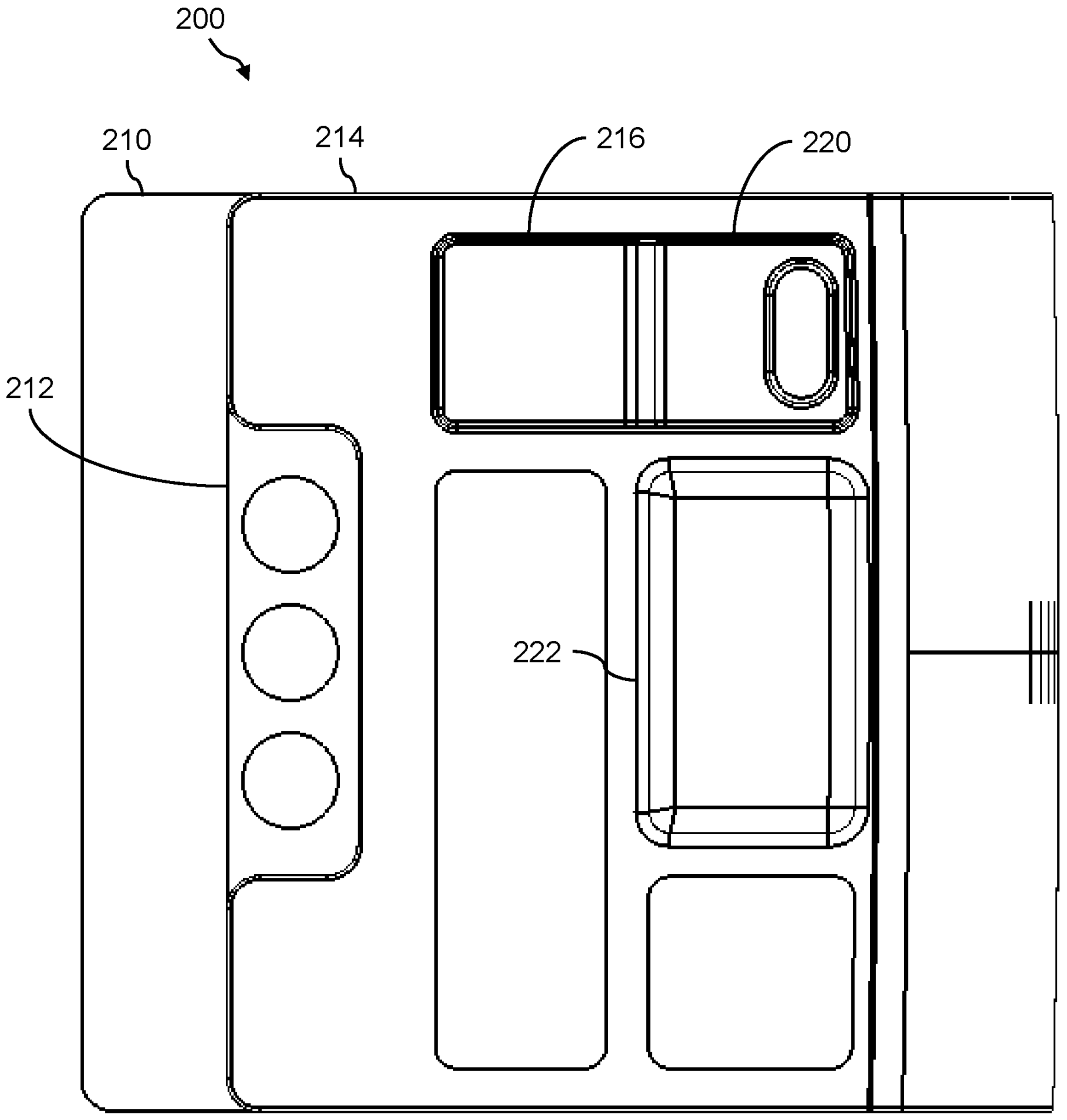
Figure 29A:
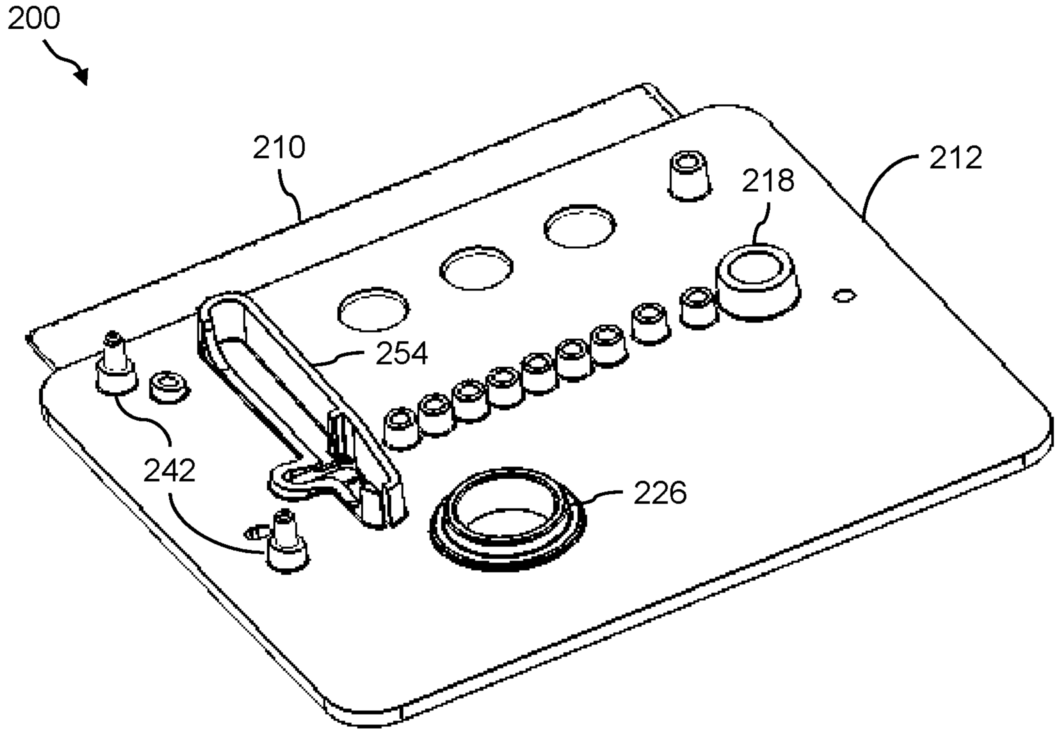
Figure 29B:
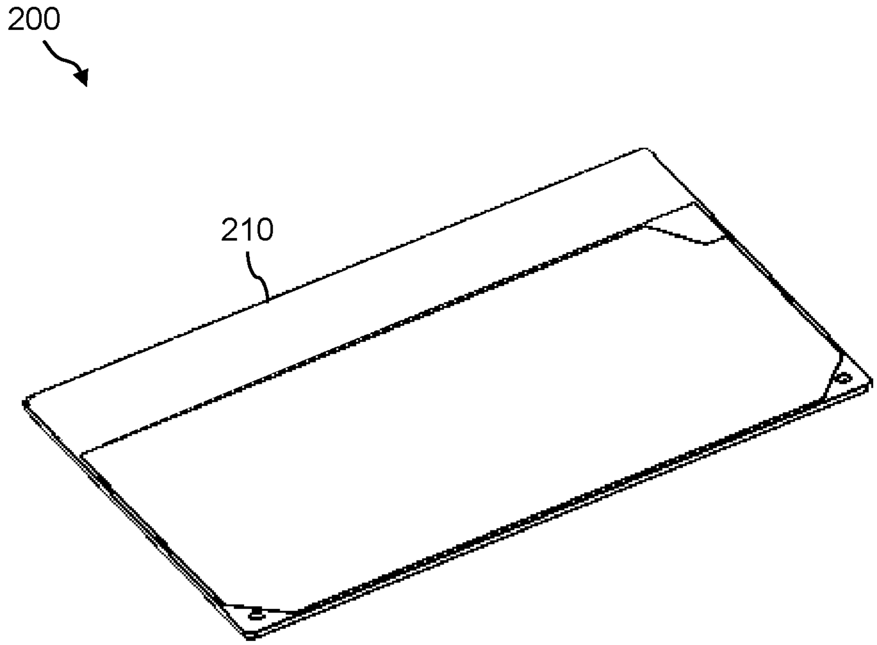
Figure 30A:
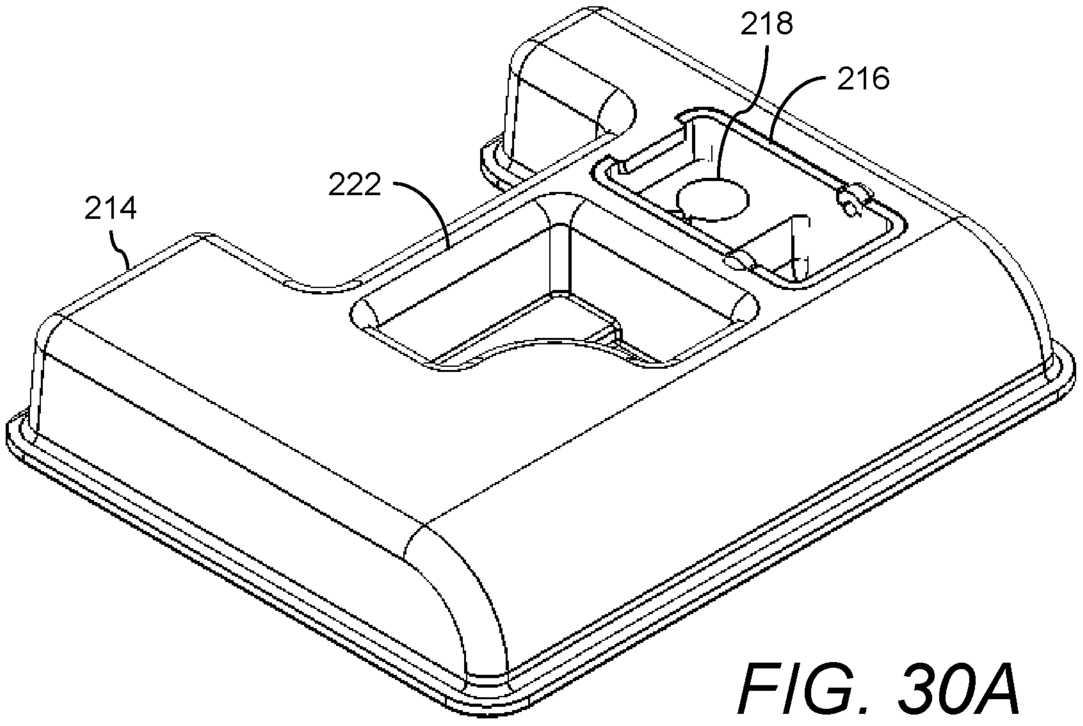
Figure 30B:
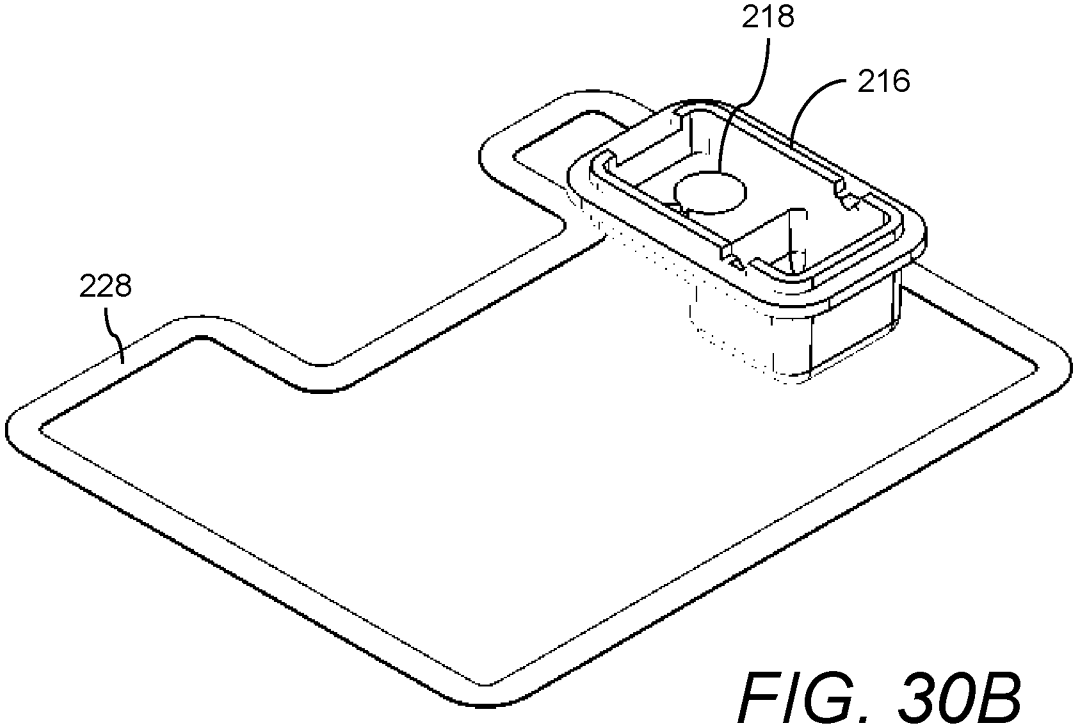
Figure 31A:
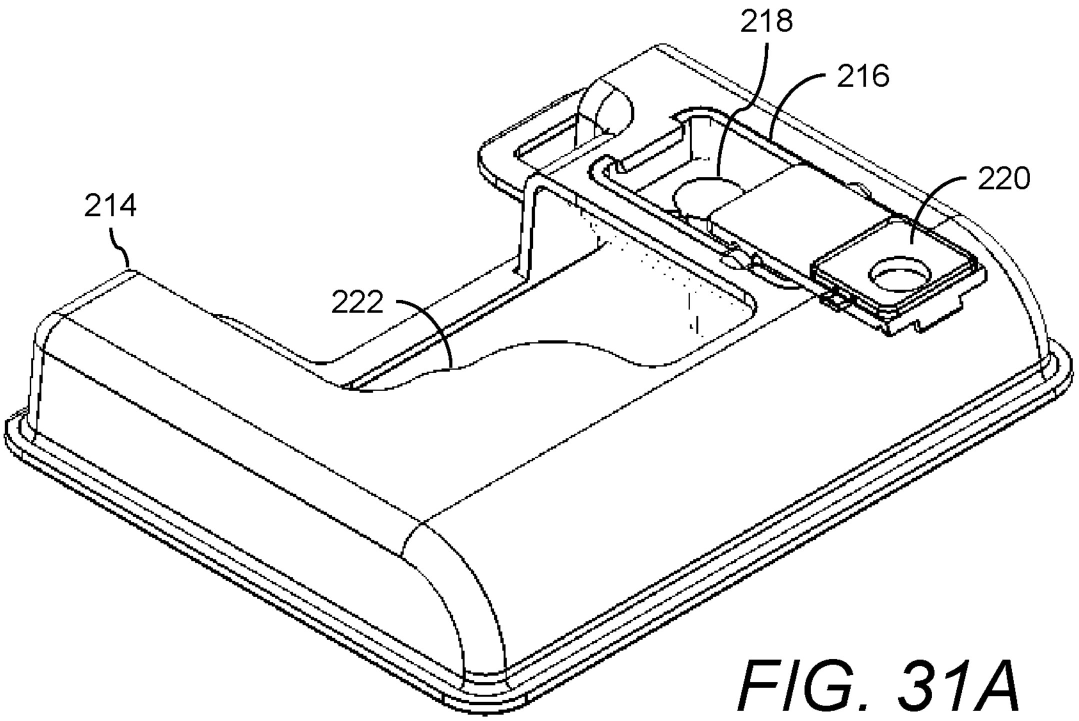
Figure 31B:
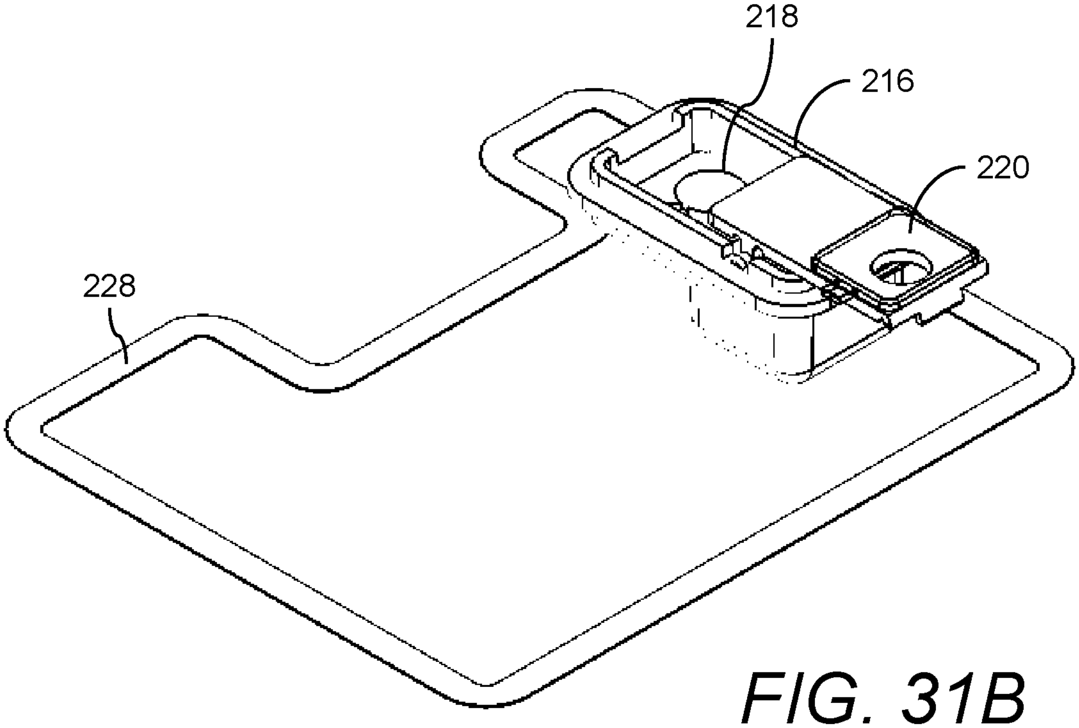
Figure 32A:
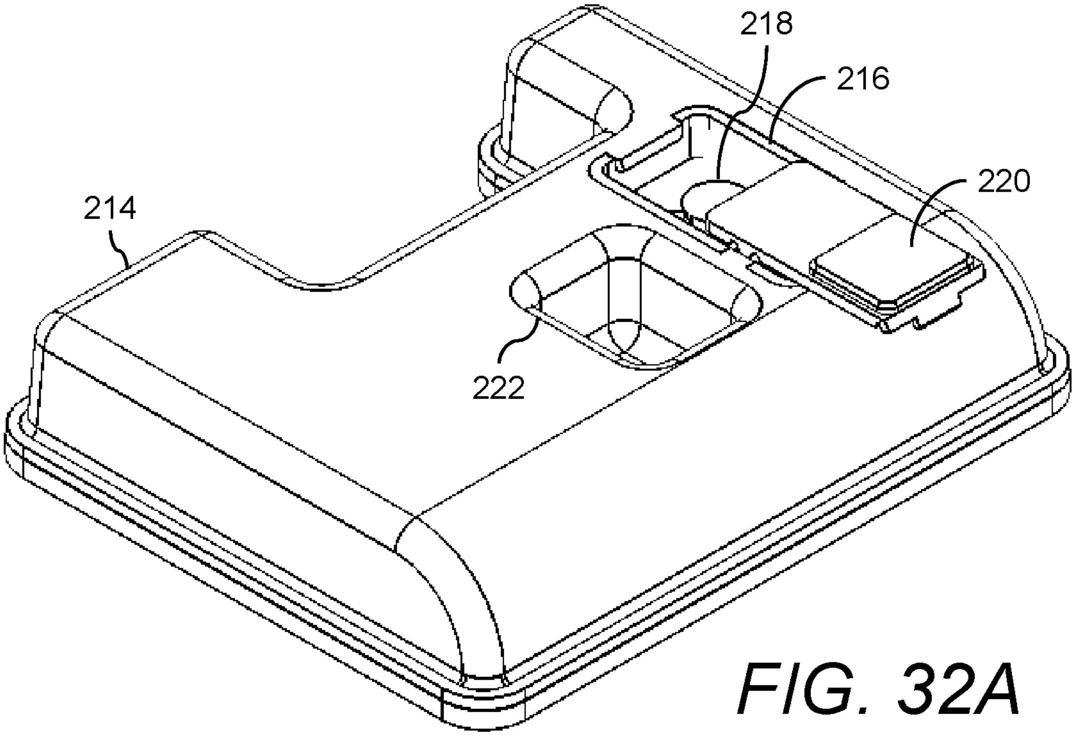
Figure 32B:
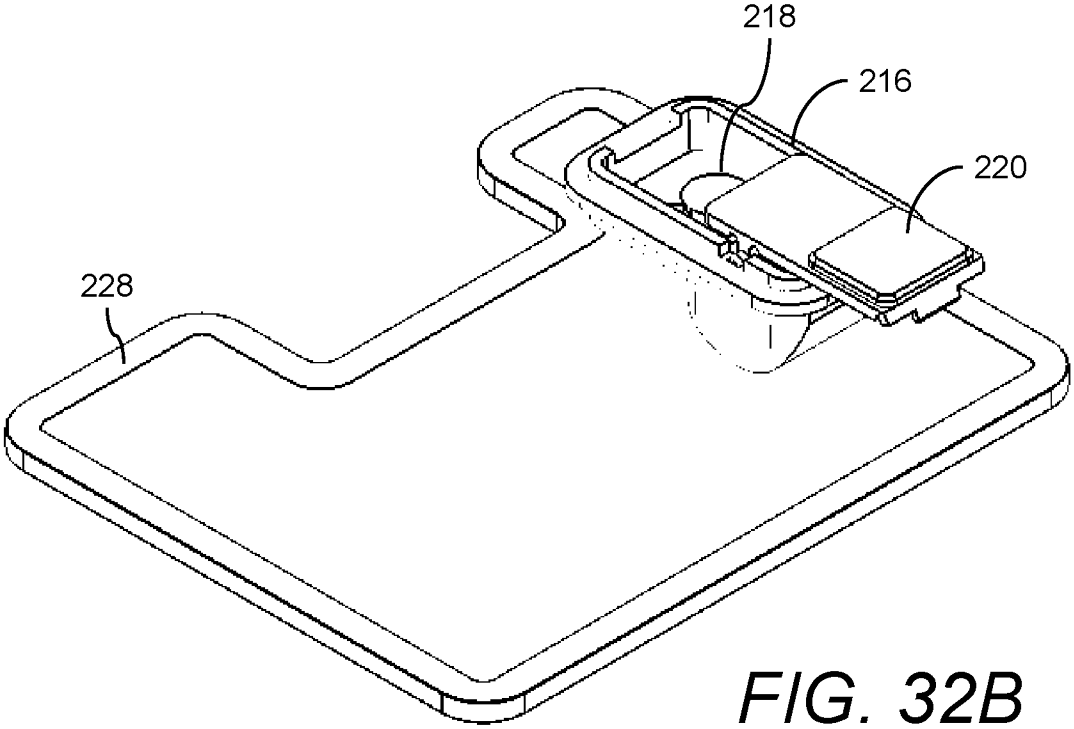
Figure 33A:
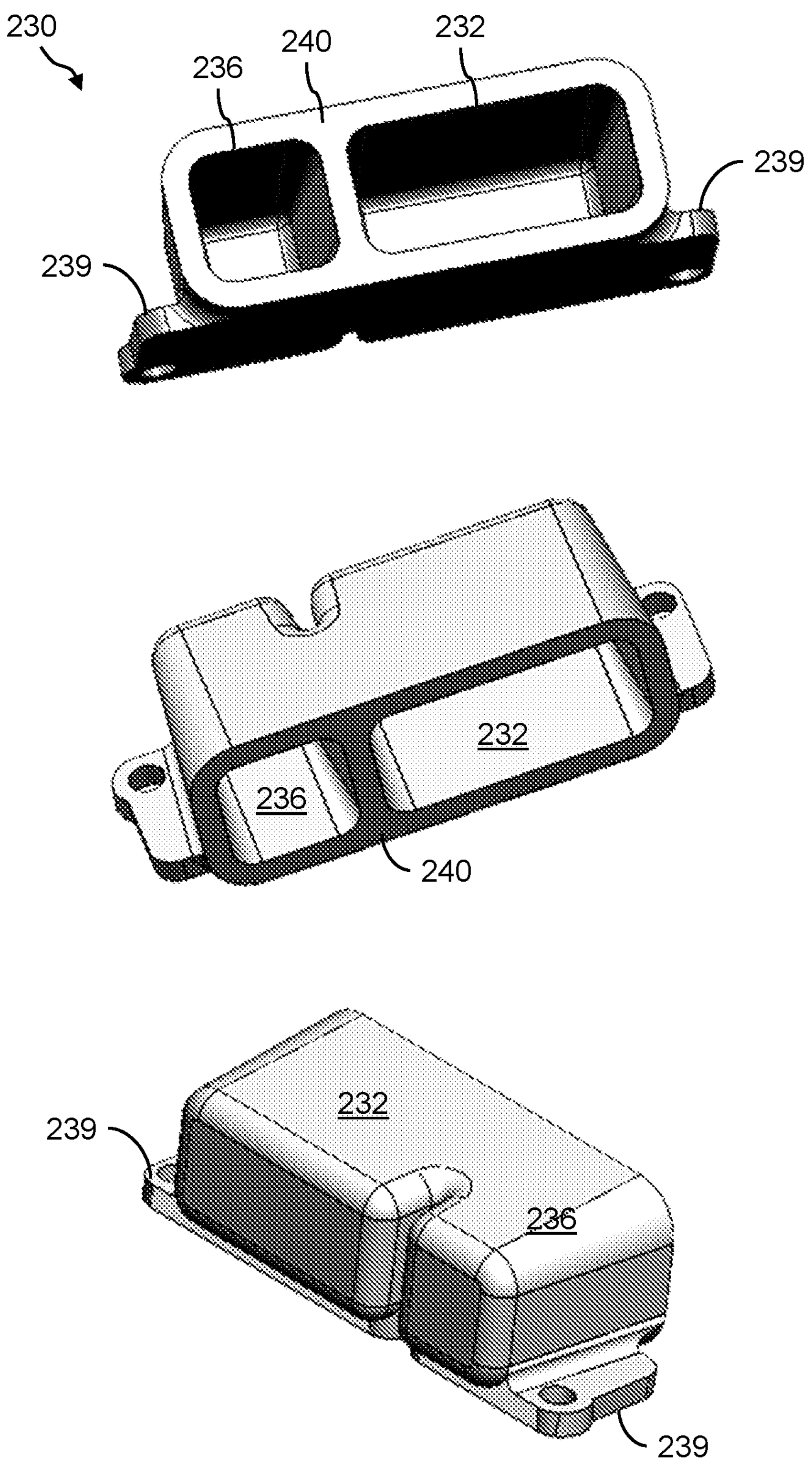
Figure 33B:
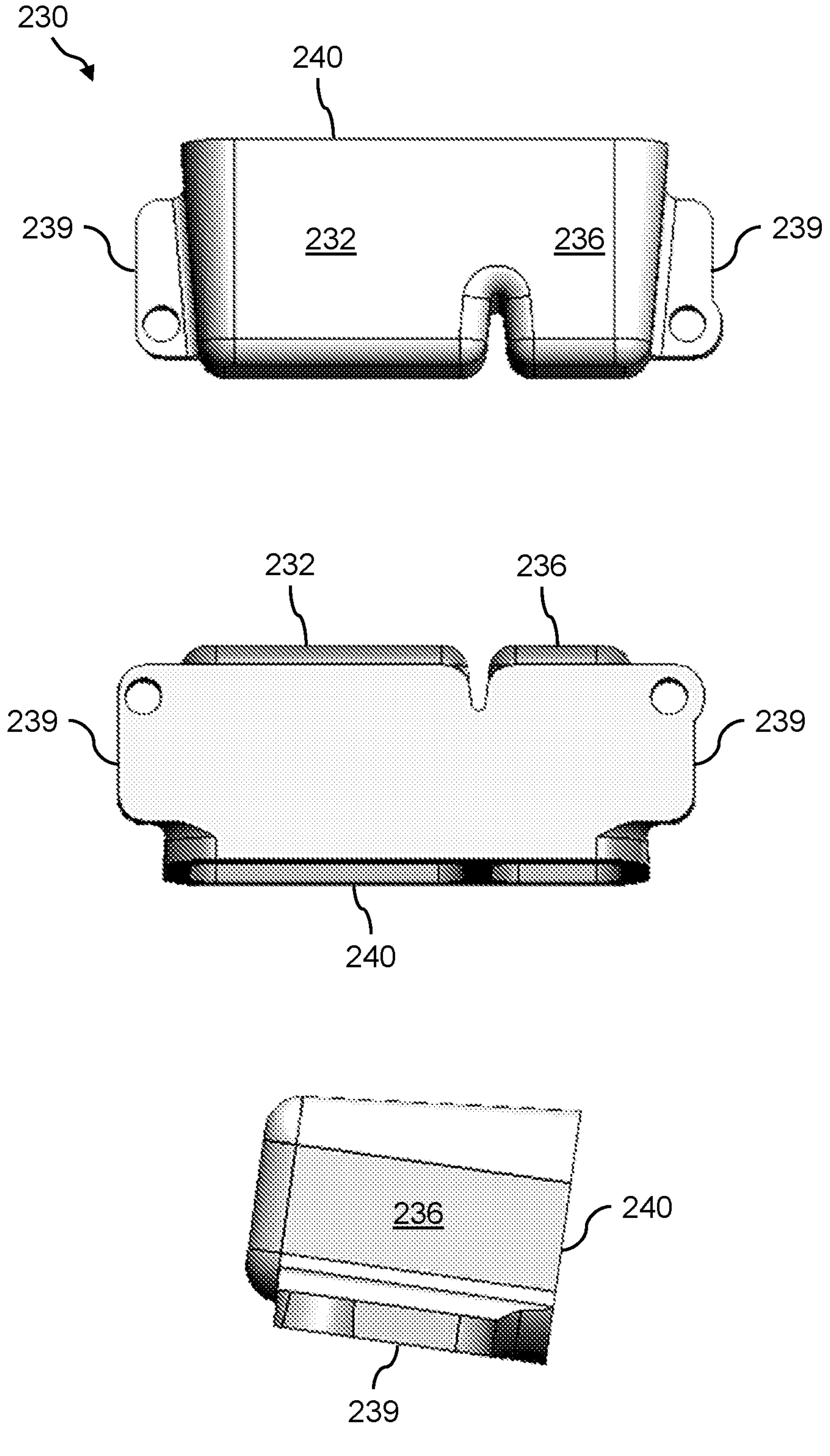
Figure 34A:
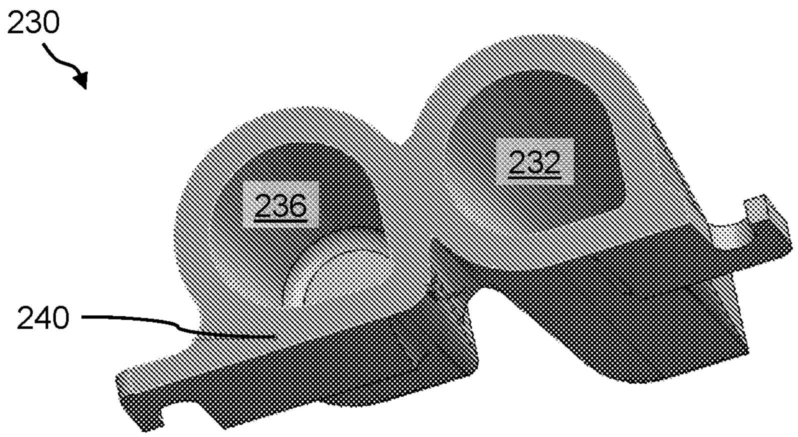
Figure 34B:
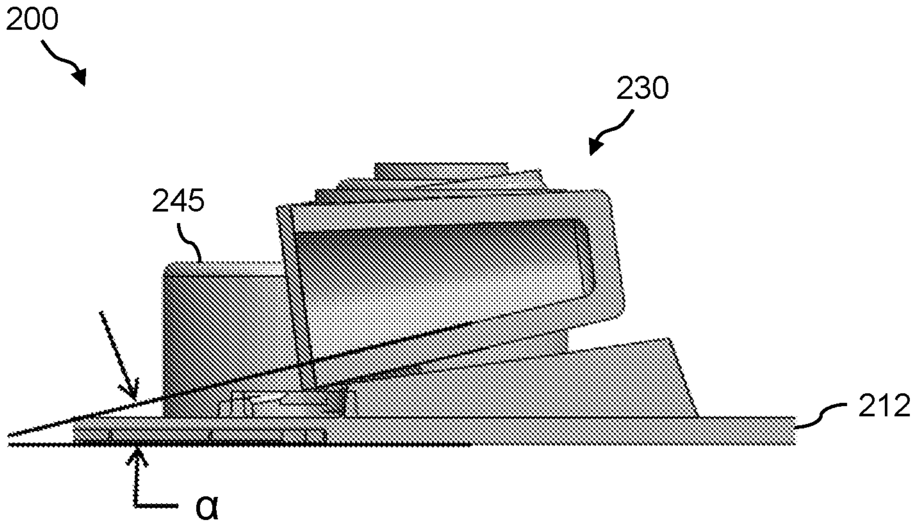
Figure 36:
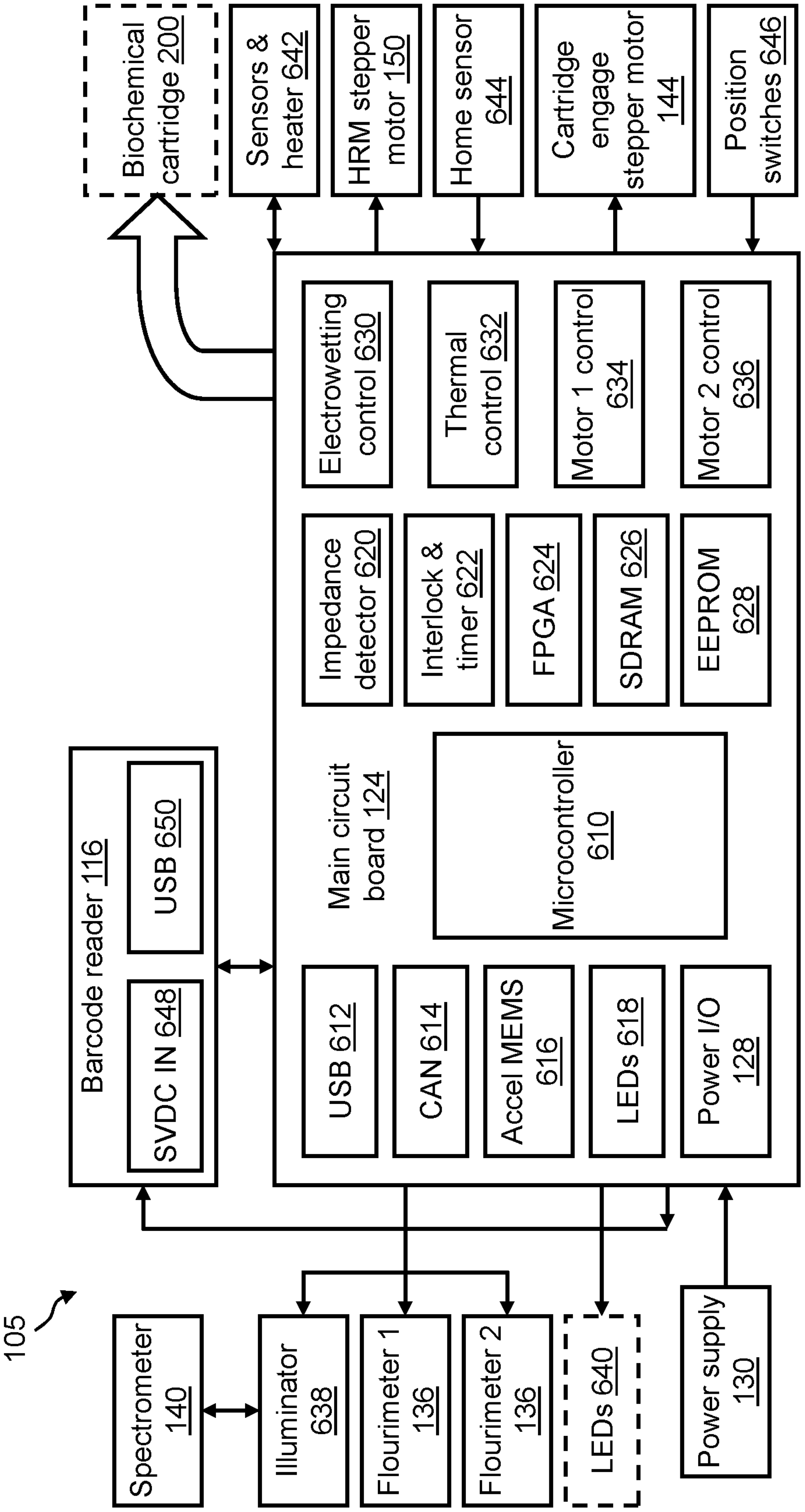
Figure 53:
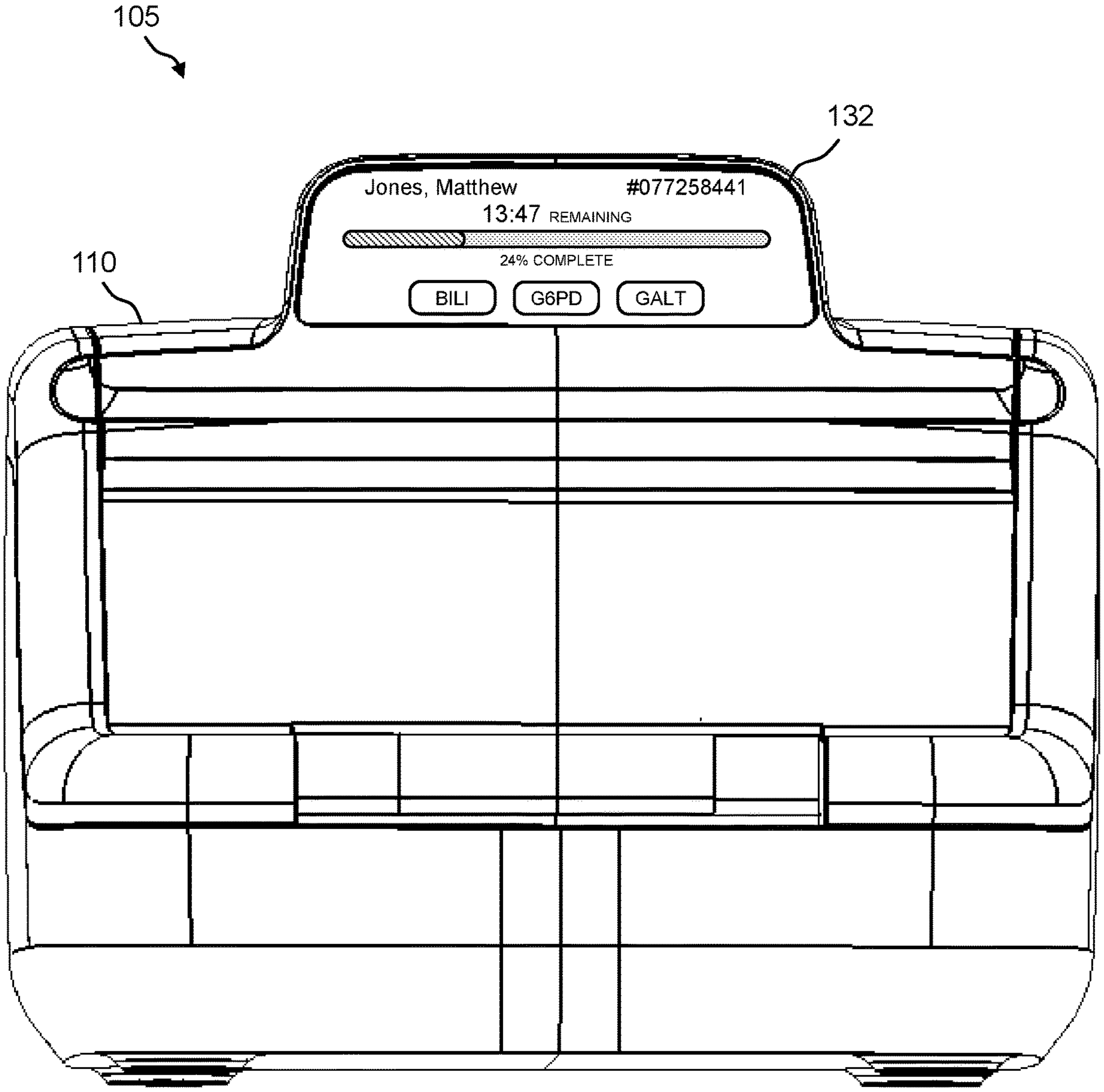
Figure 54:
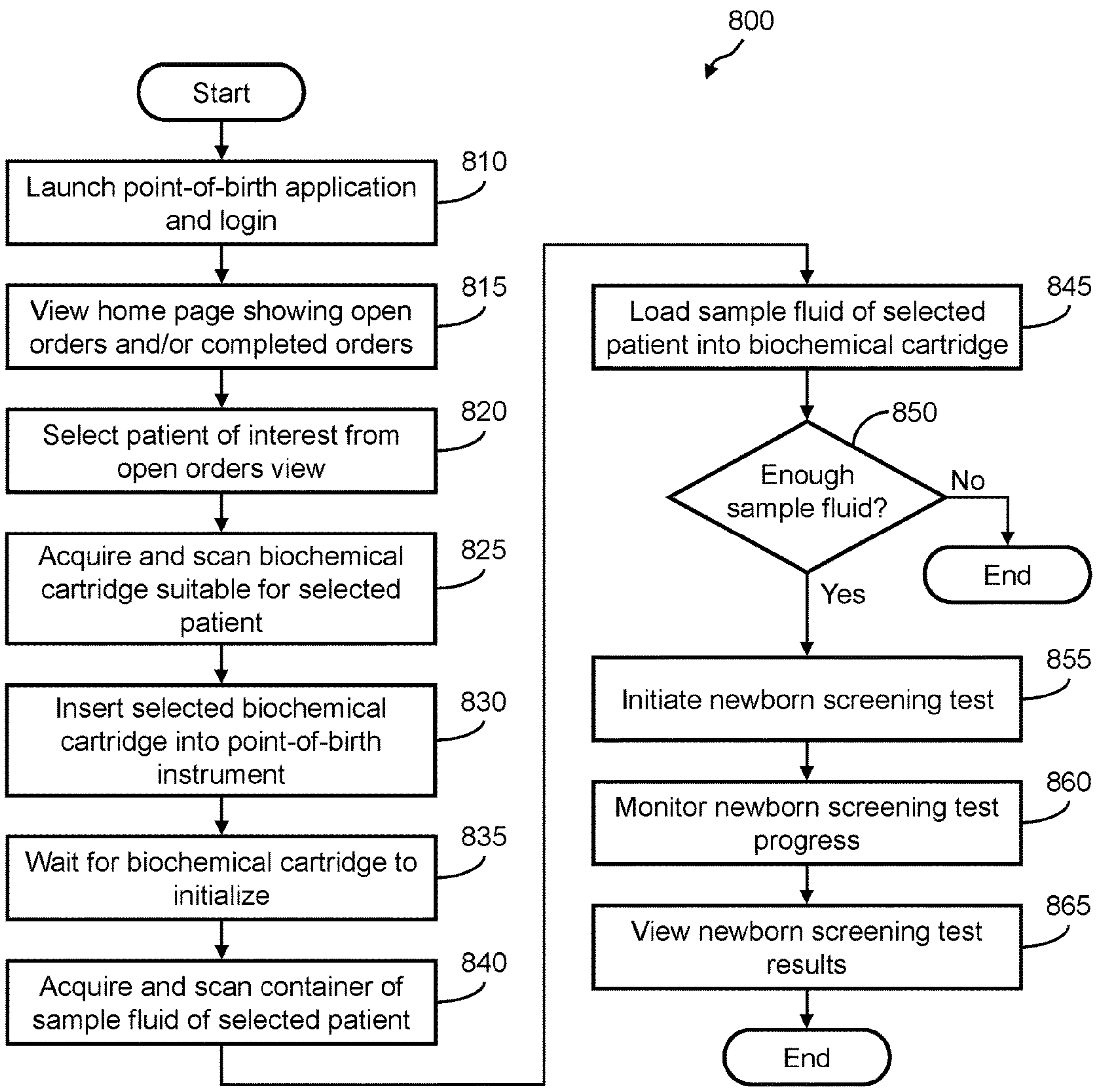
Figure 55:
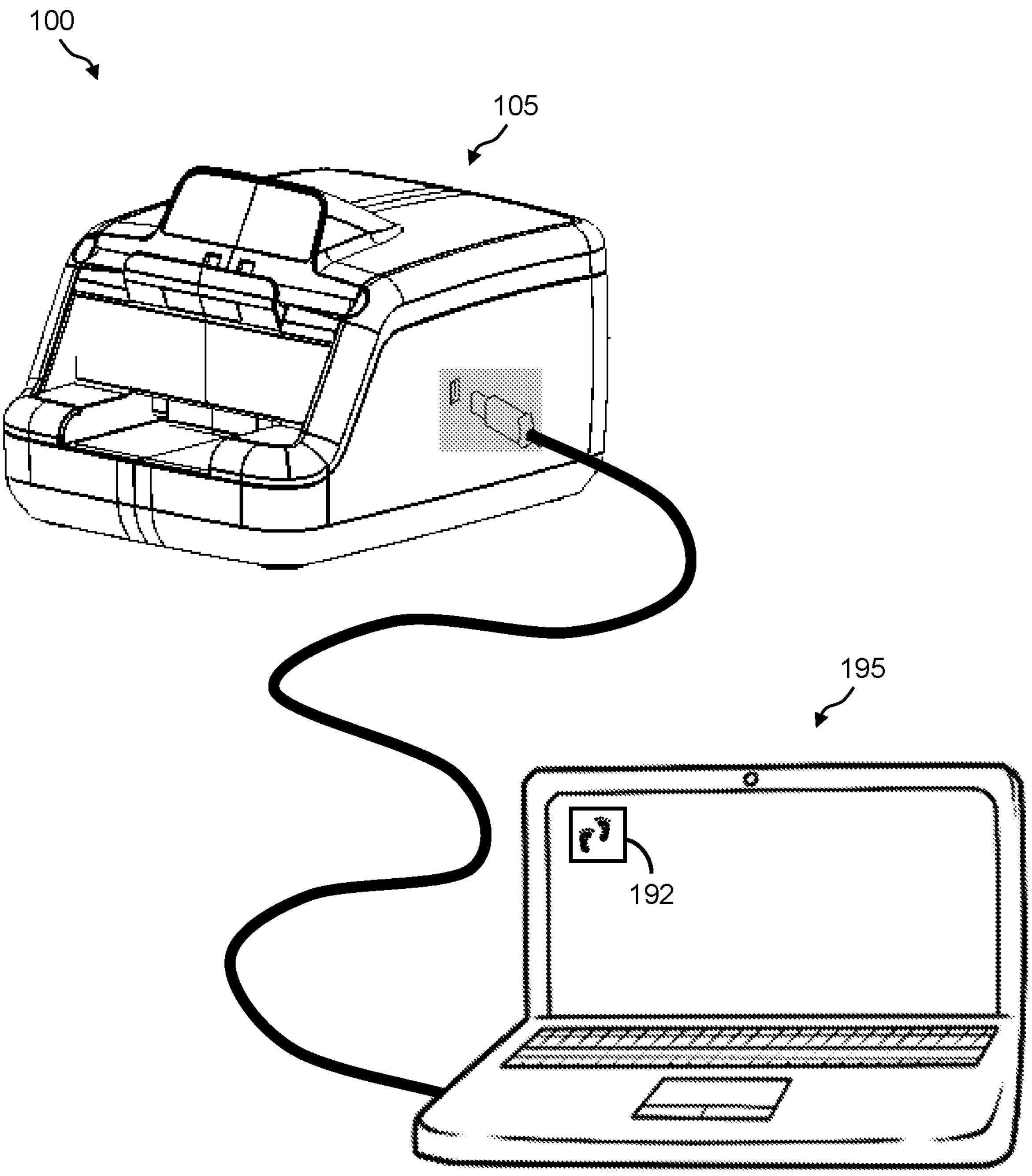

Having thus described the presently disclosed subject matter in general terms, reference will now be made to the accompanying Drawings, which are not necessarily drawn to scale, and wherein:

FIG. 1 illustrates a block diagram of an example of a point-of-birth platform that supports both newborn biological screening and newborn physiological screening according to the invention;

FIG. 2A and FIG. 2B illustrate perspective exploded views of an example of the presently disclosed point-of-birth system and instrument, and biochemical cartridge for newborn screening;

FIG. 3A through FIG. 3F illustrate a front view, a back view, a top view, a bottom view, a left side view, and a right side view, respectively, of the point-of-birth instrument shown in FIG. 2A;

FIG. 4, FIG. 5, FIG. 6, and FIG. 7 show the point-of-birth instrument of FIG. 2A and FIG. 2B absent the housing and thereby revealing more details of the components thereof;

FIG. 8A and FIG. 8B illustrate a perspective view and an exploded view, respectively, of another example of the presently disclosed point-of-birth system and instrument, and biochemical cartridge for newborn screening;

FIG. 9A and FIG. 9B illustrate a perspective view and an exploded view, respectively, of yet another example of the presently disclosed point-of-birth system and instrument, and biochemical cartridge for newborn screening;

FIG. 10A and FIG. 10B illustrate a perspective view and an exploded view, respectively, of still another example of the presently disclosed point-of-birth system and instrument, and biochemical cartridge for newborn screening;

FIG. 11 and FIG. 12 illustrate a front perspective view and a rear perspective view, respectively, of an example of the presently disclosed biochemical cartridge for newborn screening, wherein the biochemical cartridge includes digital fluidics capability;

FIG. 13, FIG. 14, FIG. 15, and FIG. 16 illustrate a side view, a rear view, a top view, and a bottom view, respectively, of the biochemical cartridge shown in FIG. 11 and FIG. 12;

FIG. 17 through FIG. 20 illustrate various views showing yet other details of the biochemical cartridge shown in FIG. 11 and FIG. 12, wherein the biochemical cartridge is shown absent the cover and thereby revealing more details thereof;

FIG. 21 illustrates a perspective view of the underside of the cover of the biochemical cartridge shown in FIG. 11 and FIG. 12;

FIG. 22A illustrates a perspective view of the underside of the biochemical cartridge shown in FIG. 11 and FIG. 12 absent the cover;

FIG. 22B illustrates a perspective view of the underside of the biochemical cartridge shown in FIG. 11 and FIG. 12 further absent the bottom substrate;

FIG. 23A illustrates a perspective view of the top substrate in relation to the bottom substrate of the biochemical cartridge shown in FIG. 11 and FIG. 12;

FIG. 23B illustrates a perspective view of the bottom substrate only of the biochemical cartridge shown in FIG. 11 and FIG. 12;

FIG. 24A and FIG. 24B illustrate an exploded view and a perspective view, respectively, of a motor of the point-of-birth instrument in relation to the biochemical cartridge shown in FIG. 11 and FIG. 12;

FIG. 25 illustrates a perspective view of another configuration of a motor of a point-of-birth instrument in relation to a biochemical cartridge;

FIG. 26 illustrates a perspective view of an example of the presently disclosed biochemical cartridge for newborn screening, wherein the biochemical cartridge is absent digital fluidics capability;

FIG. 27 and FIG. 28 illustrate a perspective view and a top view, respectively, of another example of the presently disclosed biochemical cartridge for newborn screening, wherein the biochemical cartridge is absent digital fluidics capability;

FIG. 29A illustrates a perspective view of an example of a top substrate and a bottom substrate of a biochemical cartridge that does not support digital fluidics;

FIG. 29B illustrates a perspective view of the bottom substrate only of a biochemical cartridge that does not support digital fluidics;

FIG. 30A through FIG. 32B illustrate perspective views of other examples of cover assemblies that can be used with the presently disclosed biochemical cartridges for newborn screening;

FIG. 33A and FIG. 33B illustrate various views of an example of a horizontal reservoir module of the presently disclosed biochemical cartridge for newborn screening;

FIG. 34A illustrates a front perspective view of the horizontal reservoir module and showing a front face sealing surface thereof;

FIG. 34B illustrates a cross-sectional view of the horizontal reservoir module and showing a dispensing angle thereof;

FIG. 35A through FIG. 35H illustrate an example of a process of deploying the horizontal reservoir module of the presently disclosed biochemical cartridge for newborn screening;

FIG. 36 illustrates an example of a functional block diagram of, for example, the point-of-birth instrument of FIG. 2A and FIG. 2B;

FIG. 37 through FIG. 52 illustrate an example the graphical user interface (GUI) of the presently disclosed point-of-birth system and instrument, and biochemical cartridge for newborn screening;

FIG. 53 illustrates a front view of an example of the point-of-birth instrument that includes a built-in display;

FIG. 54 illustrates a flow diagram of an example of a method of using the presently disclosed point-of-birth system and instrument, and biochemical cartridge for newborn screening;

FIG. 55 illustrates an example of the presently disclosed point-of-birth system that includes a laptop computer; and FIG. 56 through FIG. 59 illustrate examples of the presently disclosed point-of-birth system that support physiological screening in combination with biochemical screening.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a point-of-birth system and instrument, biochemical cartridge, and methods for newborn screening. Namely, a point-of-birth system is provided that includes a point-of-birth instrument for receiving and processing a biochemical cartridge for performing newborn screening. Further, a smart display such as a portable smart device (i.e., a smartphone or tablet), is in communication with point-of-birth instrument, wherein the smart display may include a newborn screening (NBS) mobile app, which is the user interface for operating the point-of-birth system. Further, a method is provided of using the point-of-birth system.

In one embodiment, the point-of-birth system and point-of-birth instrument support newborn biological screening only. However, in other embodiments, the point-of-birth system and point-of-birth instrument support both newborn biological screening and newborn physiological screening (e.g., newborn pulse oximetry and newborn hearing screening).

An aspect of the presently disclosed point-of-birth system and instrument, biochemical cartridge, and methods for newborn screening is that it is highly portable and easy to use.

Another aspect of the presently disclosed point-of-birth system and instrument, biochemical cartridge, and methods for newborn screening is that the liquid delivery system of the biochemical cartridge features a horizontal reservoir module (HRM) that is tilted or angled for reliable dispensing of liquids by gravity.

Referring now to FIG. 1 is a block diagram of an example of a point-of-birth platform 10 that supports both newborn biological screening and newborn physiological screening according to the invention. For example, point-of-birth platform 10 supports both biological screening 20 and physiological screening 30.

The biological screening 20 may utilize multiplexed testing 22. In newborn screening programs, multiplexed testing 22 refers to the capability to simultaneously identify several compounds. In point-of-birth platform 10, biological screening 20 includes screening for certain biological markers. Example biological markers may include, but are not limited to, total bilirubin (TSB) for detecting hyperbilirubinemia, glucose-6-phosphate dehydrogenase deficiency (G6PD), ammonia for detecting hyperammonemia, galactose-1-phosphate uridyltransferase (GALT) for detecting GALT deficiency, and medium-chain acyl-CoA dehydrogenase (MCAD) for detecting MCAD deficiency.

Physiological screening 30 may include, but is not limited to, newborn pulse oximetry 32 and newborn hearing screening 34. Newborn pulse oximetry 32 is an accepted test that improves detection of critical congenital heart defects (CCHD). Newborn hearing screening 34 (aka Early Hearing Detection and Intervention (EHDI)) refers to the practice of screening every newborn for hearing loss prior to hospital discharge. For example, the auditory brainstem response (ABR) test and the otoacoustic emissions (OAEs) test are appropriate physiologic measures for screening the newborn population. Both are noninvasive. The ABR test gives information about the inner ear (cochlea) and brain pathways for hearing. The OAEs test can detect blockage in the outer ear canal, as well as the presence of middle ear fluid and damage to the outer hair cells in the cochlea.

Point-of-birth platform 10 provides advantages over laboratory-based technologies in that it provides capability to (1) process low-volume blood samples, (2) test more than one analyte with one sample on the same cartridge and platform, (3) run different types of biochemical testing (enzymatic, colorimetric, immunoassay, and nucleic acid tests) on one platform, and (4) perform a more complete disease or disease risk determination prior to newborn discharge from the hospital. The point-of-birth platform 10 is also differentiated from conventional point-of-care biochemical assay platforms because it focuses exclusively on newborn-related testing with an assay menu that is focused on the ailments of newborns.

Point-of-birth platform 10 can be instantiated via a point-of-birth system, point-of-birth instrument, biochemical cartridge, and methods for newborn screening. Point-of-birth platform 10 has the potential to revolutionize newborn screening not only in the United States but also in developing countries where the infrastructure for such testing is nonexistent. Very little user training will be required. Further, the point-of-birth instruments can be installed via remote guides in under an hour. More details of examples of the point-of-birth system, point-of-birth instrument, biochemical cartridge, and methods for newborn screening are shown and described hereinbelow with reference to FIG. 2A through 59.

Referring now to FIG. 2A and FIG. 2B is perspective exploded views of an example of the presently disclosed point-of-birth system 100, point-of-birth instrument 105, and biochemical cartridge 200 for newborn screening. Point-of-birth system 100 is based on the architecture shown in point-of-birth platform 10 of FIG. 1.

Namely, a point-of-birth system 100 includes a point-of-birth instrument 105 that can be mechanically and communicatively coupled to a smart display, such as a portable smart device 190, wherein smart device 190 can be the user interface and the network connection device for point-of-birth instrument 105. Smart device 190 can be, for example, a smartphone or tablet device. Point-of-birth system 100 further includes a biochemical cartridge 200. Biochemical cartridge 200 is a disposable cartridge for receiving the sample fluid to be processed, which has been collected from a newborn baby of interest. Biochemical cartridge 200 can be plugged into point-of-birth instrument 105 for processing. More details of examples of biochemical cartridge 200 are shown and described hereinbelow with reference to FIG. 11 through FIG. 35H.

Point-of-birth instrument 105 includes a housing (or body) 110, a cartridge loading deck 112 for receiving biochemical cartridge 200, a docking station 114 for receiving smart device 190, and an input reader such as a barcode reader 116 for scanning any information related to point-of-birth system 100, such as operator ID information, cartridge ID information, and sample ID information. In one example, smart device 190 can be physically docked in docking station 114 for electrically connecting (e.g., for power and communication) to point-of-birth instrument 105. However, in another example, smart device 190 can be held separate from point-of-birth instrument 105 and communicate wirelessly with point-of-birth instrument 105, albeit there is no power connection. Further, a newborn screening (NBS) mobile app 192 can be present on smart device 190 for operating point-of-birth system 100.

Figure 56:
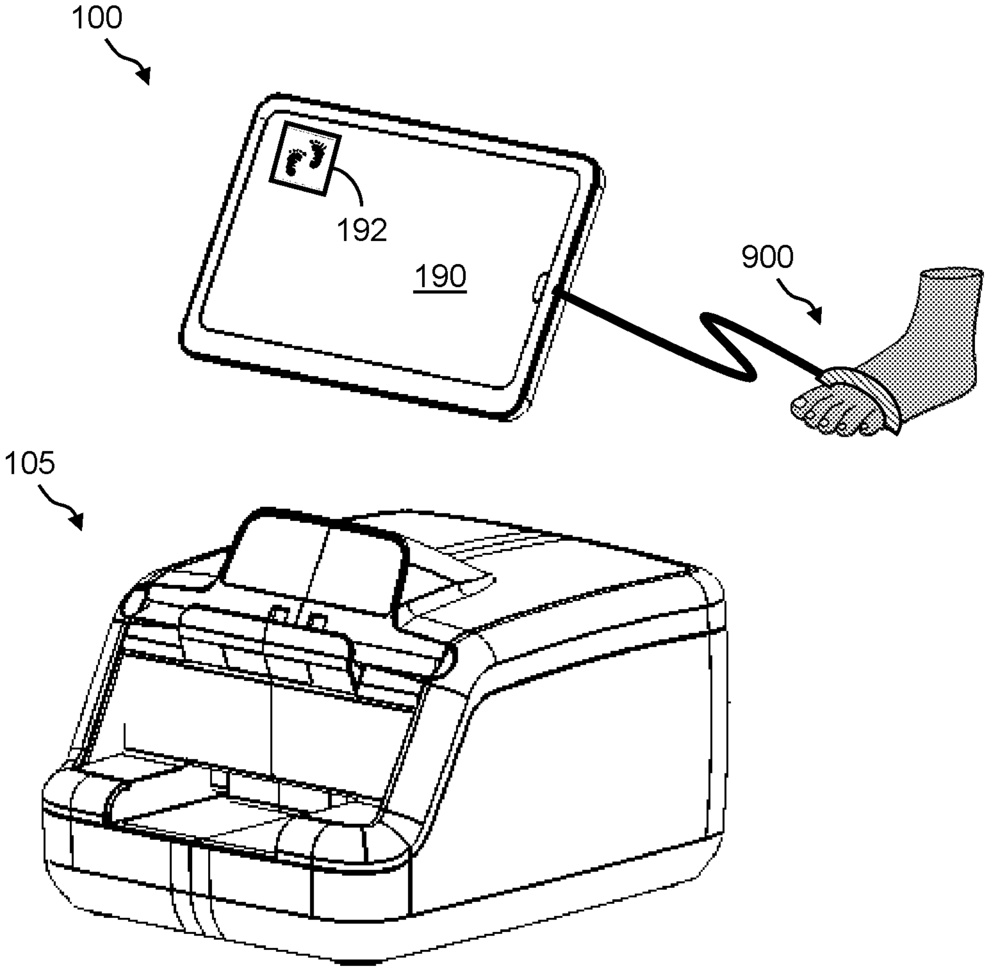
Figure 57:
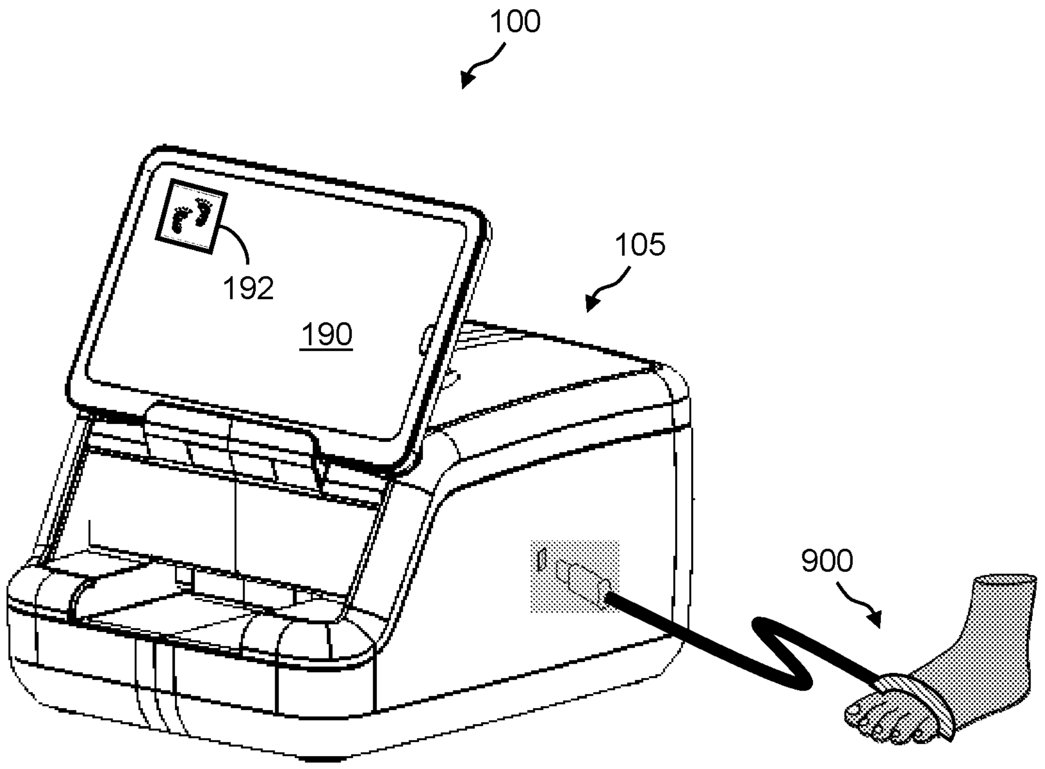
Figure 58:
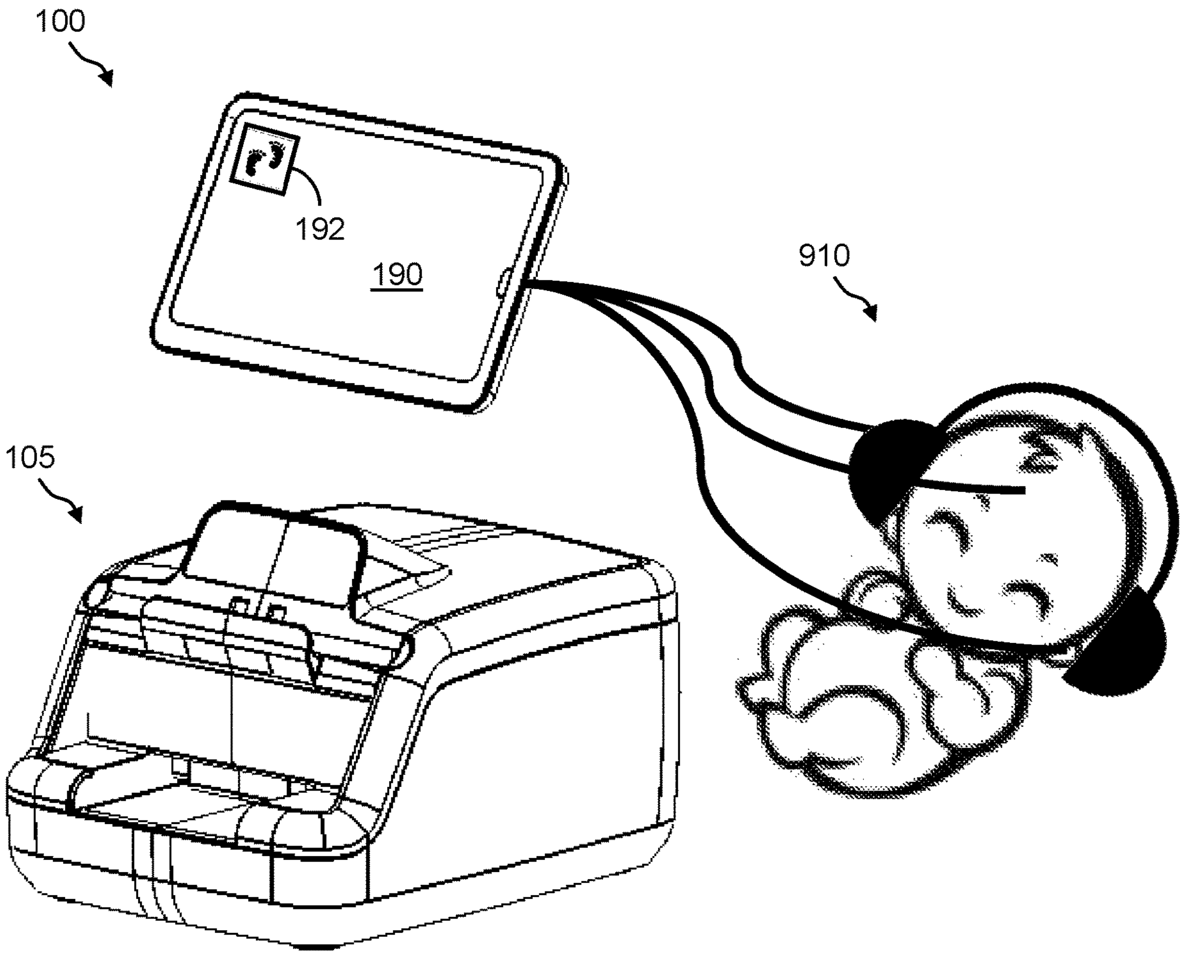
Figure 59:
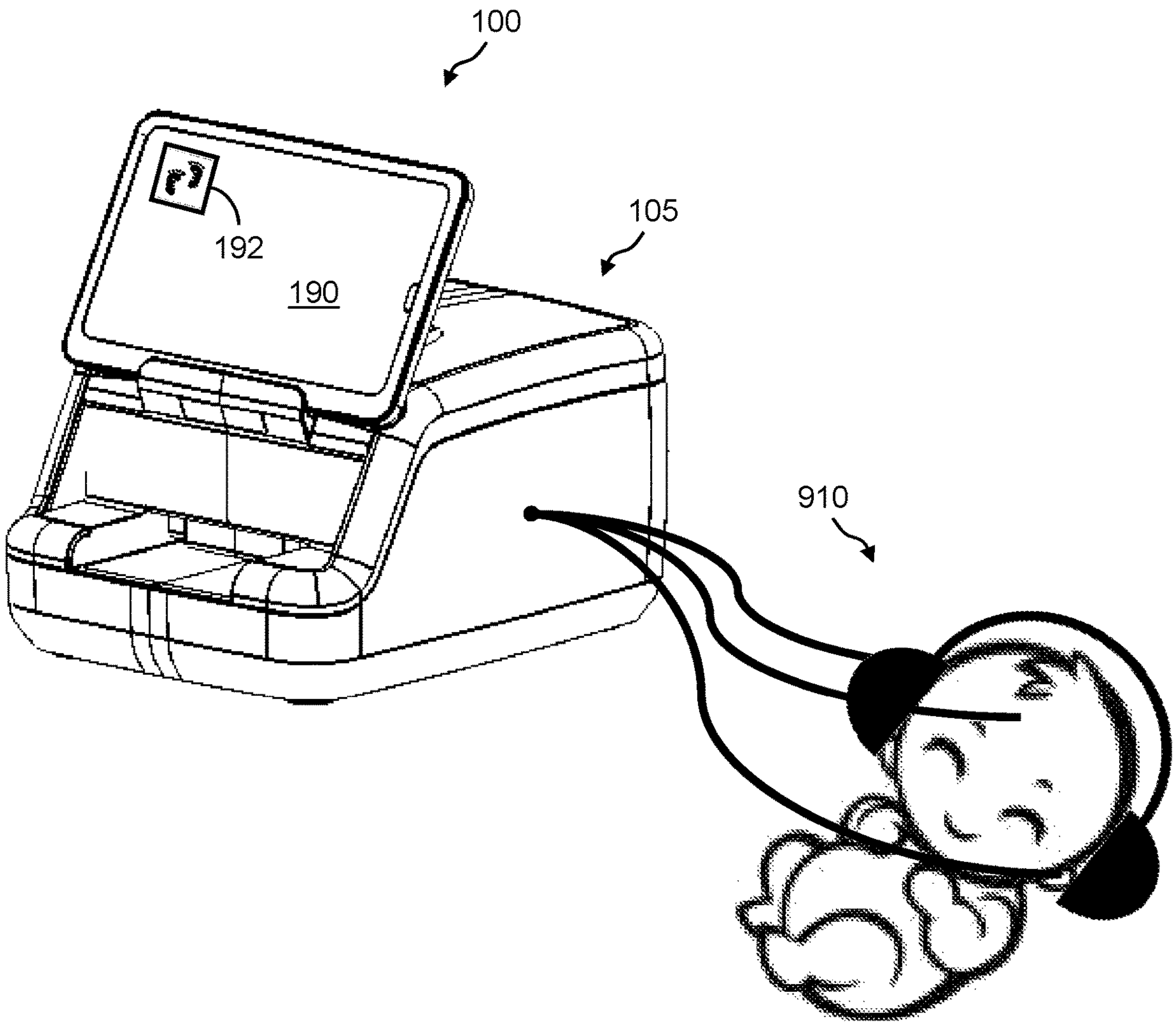

Point-of-birth system 100 is a near birth platform that can be used, for example, to (1) test one baby or many babies at a time, (2) perform biochemical assays (enzymatic, colorimetric and immunoassays), (3) perform hearing screening (using auditory brainstem response or optoacoustic emissions, see FIG. 56 and FIG. 57) and (4) perform pulse oximetry testing (see FIG. 58 and FIG. 59). Again, the testing menu may include, but is not limited to, newborn testing for total bilirubin (TSB), glucose-6-phosphate dehydrogenase deficiency (G6PD), hyperammonemia, galactosemia, and other disorders.

Point-of-birth instrument 105 is a lightweight and portable device. Housing (or body) 110 of point-of-birth instrument 105 can be formed of any lightweight, strong, durable material, such as, but not limited to, molded plastic and metal (e.g., aluminum). Point-of-birth instrument 105 can be, for example, from about 7 inches (17.78 cm) to about 9 inches (22.86 cm) wide; from about 7 inches (17.78 cm) to about 10 inches (25.4 cm) high; and from about 10 inches (25.4 cm) to about 12 inches (30.48 cm) deep. In one example, point-of-birth instrument 105 is about 8 inches (20.32 cm) wide, about 9 inches (22.86 cm) high, and about 11 inches (27.94 cm) deep. However, any variations in physical features are possible. For example, FIG. 2A shows an example of point-of-birth instrument 105 that has a tall physical profile, while FIG. 2B shows an example of point-of-birth instrument 105 that has a shorter physical profile. Further to the example, FIG. 3A through FIG. 3F show a front view, a back view, a top view, a bottom view, a left side view, and a right side view, respectively, of the point-of-birth instrument 105 shown in FIG. 2A.

Point-of-birth instrument 105 can operate either using electrical power or using battery power. Again, point-of-birth instrument 105 may have the capability to interface with a smart display, such as a smartphone or tablet device (e.g., smart device 190), and may have modules for biochemical testing, pulse oximetry and hearing screening. NBS mobile app 192 can be used, for example, to text the results to concerned persons, provide lists of follow up physicians, provide training, perform clinical calculations such as nomogram for bilirubin measurements, perform epidemiological tracking of diseases, and the like. Further, point-of-birth instrument 105 includes optical detection systems for biochemical screening that include fluorescence for 1-2 sets of wavelengths and absorbance across the ultraviolet (UV) range of from about 400 nm to about 800 nm.

Biochemical cartridge 200 may use any physiological fluid including urine and whole blood samples. There are two primary processing steps for biochemical testing: (1) loading the sample onto biochemical cartridge 200 and (2) loading biochemical cartridge 200 into point-of-birth instrument 105. Point-of-birth instrument 105 includes a processor or controller for managing the operations thereof; namely, running assays. The total assay time for biochemical assays maybe about 15 minutes from sample input to result output. Point-of-birth instrument 105 preferably includes all software necessary to run each type of test. Point-of-birth instrument 105 is also preferably designed to be robust without routine maintenance. More details of the components of point-of-birth instrument 105 are shown and described hereinbelow with reference to FIG. 4, FIG. 5, FIG. 6, and FIG. 7.

Referring now to FIG. 4, FIG. 5, FIG. 6, and FIG. 7 is various views of point-of-birth instrument 105 of FIG. 2A and FIG. 2B absent housing (or body) 110 and thereby revealing more details of the components thereof. For example, point-of-birth instrument 105 includes barcode reader 116, two side rails 120 mounted atop a base plate 122, a main circuit board 124 and a lower circuit board 126 arranged between the two side rails 120, a power input port 128 and a power supply assembly 130 arranged on a power supply mounting plate 132, a cartridge deck plate 134, one or more fluorimeters 136 on a fluorimeter mounting plate 138, a spectrometer 140, a cam 142 arranged between the two side rails 120, a cartridge engage stepper motor 144, a cam belt and pulley assembly 146, a stepper motor 150 on a stepper motor support 152, a spring-loaded adaptor 154, a motor shaft 156, and a motor engaging member 158.

Barcode reader 116 can be any standard barcode technology. During testing operations of point-of-birth instrument 105, barcode reader 116 is used to capture information such as operator ID information, cartridge ID information, and sample ID information.

Side rails 120, base plate 122, and cartridge deck plate 134 can be any strong rigid members, such as plastic or metal members.

Main circuit board 124 and lower circuit board 126 include electronics for controlling the overall operations of point-of-birth instrument 105. See FIG. 36 for examples of functions that can be implemented on main circuit board 124 and lower circuit board 126.

Point-of-birth instrument 105 can operate on electrical power or battery power. In one example, point-of-birth instrument 105 uses battery power (batteries not shown) and therefore power input port 128 is not used. In another example, point-of-birth instrument 105 is powered using a DC adaptor. In this case, power input port 128 receives the DC adaptor plug. Using either battery power or a DC adaptor, the DC source supplies power supply assembly 130 that conditions the DC input as needed for powering the active components of point-of-birth instrument 105. In yet another example, point-of-birth instrument 105 is powered using standard household AC voltage. In this case, power input port 128 receives an AC plug and power supply assembly 130 performs an additional AC to DC conversion function.

As is well known, a fluorimeter is an instrument for measuring the intensity of fluorescence, and commonly used in biochemical analysis. As is well known, an optical spectrometer is an instrument used to measure properties of light over a specific portion of the electromagnetic spectrum, and commonly used in spectroscopic analysis to identify materials. Accordingly, fluorimeters 136 and spectrometer 140 are used for optical detection in point-of-birth instrument 105.

In point-of-birth instrument 105, when biochemical cartridge 200 is inserted into cartridge loading deck 112, the edge of bottom substrate 210 of biochemical cartridge 200 engages with cam 142. Then, using cartridge engage stepper motor 144, cam 142 is rotated in order to pull and lock biochemical cartridge 200 into a secure position. Cartridge engage stepper motor 144 can be, for example, one of the PKP Series 2-phase, single shaft, stepper motors (1.8°) available from Oriental Motor U.S.A. Corp (Charlotte, N.C.). Cartridge engage stepper motor 144 is rotatively coupled to cam 142 via cam belt and pulley assembly 146.

Stepper motor 150 engages with biochemical cartridge 200 (see FIG. 24A and FIG. 24B) and is used to actuate the liquid dispensing mechanism within biochemical cartridge 200. Stepper motor 150 can also be, for example, one of the PKP Series 2-phase, single shaft, stepper motors (1.8°) from Oriental Motor U.S.A. Corp.

The aforementioned components are a sampling of the main components of point-of-birth instrument 105, albeit not a full list of components in its entirety. More details of the functions that can be supported by the components of point-of-birth instrument 105 are shown and described hereinbelow with reference to FIG. 36.

Referring now to FIG. 8A and FIG. 8B is a perspective view and an exploded view, respectively, of another example of the presently disclosed point-of-birth system and instrument, and biochemical cartridge for newborn screening. In this example, point-of-birth system 100 includes a point-of-birth instrument 305, smart device 190, and biochemical cartridge 200. Point-of-birth instrument 305 includes a housing (or body) 310, a cartridge loading deck 312 for receiving biochemical cartridge 200, and a docking station 314 for receiving smart device 190. Point-of-birth instrument 305 may have slightly different dimensions, function, and aesthetic features as compared with point-of-birth instrument 105 shown in FIG. 2A or FIG. 2B.

Referring now to FIG. 9A and FIG. 9B is a perspective view and an exploded view, respectively, of yet another example of the presently disclosed point-of-birth system and instrument, and biochemical cartridge for newborn screening. In this example, point-of-birth system 100 includes a point-of-birth instrument 405, smart device 190, and biochemical cartridge 200. Point-of-birth instrument 405 includes a housing (or body) 410, a cartridge loading deck 412 for receiving biochemical cartridge 200, and a docking station 414 for receiving smart device 190. Point-of-birth instrument 405 may have slightly different dimensions, function, and aesthetic features as compared with point-of-birth instrument 105 shown in FIG. 2A or FIG. 2B.

Referring now to FIG. 10A and FIG. 10B is a perspective view and an exploded view, respectively, of still another example of the presently disclosed point-of-birth system and instrument, and biochemical cartridge for newborn screening. In this example, point-of-birth system 100 includes a point-of-birth instrument 505, smart device 190, and biochemical cartridge 200. Point-of-birth instrument 505 includes a housing (or body) 510, a cartridge loading deck 512 for receiving biochemical cartridge 200, and a docking station 514 for receiving smart device 190. Point-of-birth instrument 505 may have slightly different dimensions, function, and aesthetic features as compared with point-of-birth instrument 105 shown in FIG. 2A or FIG. 2B.

Referring now to FIG. 11 and FIG. 12 is a front perspective view and a rear perspective view, respectively, of an example of the presently disclosed biochemical cartridge 200 for newborn screening, wherein biochemical cartridge 200 includes digital fluidics capability. Further, FIG. 13, FIG. 14, FIG. 15, and FIG. 16 show a side view, a rear view, a top view, and a bottom view, respectively, of the biochemical cartridge 200 shown in FIG. 11 and FIG. 12.

The terms "front," "back," "top," "bottom," "over," "under," and "on" are used throughout the description with reference to the relative positions of components of biochemical cartridge 200, such as relative positions of top and bottom substrates or front and back substrates of biochemical cartridge 200. It will be appreciated that biochemical cartridge 200 is functional regardless of its orientation in space.

In this example, biochemical cartridge 200 includes a bottom substrate 210 (e.g., a printed circuit board (PCB)) and a top substrate 212 (e.g., a plastic or glass substrate) that are separated by a gap (not shown). The gap may contain filler fluid, such as, but not limited to, a low-viscosity oil such as silicone oil or hexadecane filler fluid. During the newborn screening operations, chemical reactions or assays may be performed in the gap between bottom substrate 210 and top substrate 212.

A cover 214 (e.g., a plastic cover) is provided atop top substrate 212. A sample input well 216 is integrated into cover 214. Sample input well 216 has a loading port 218 and a well cap assembly 220 for opening and closing loading port 218. Cover 214 may also include certain recessed or contoured regions 222. Recessed or contoured regions 222 may be tailored depending on the components and/or components layout within biochemical cartridge 200.

An optics interface region 224 (see FIG. 12) is provided in relation to top substrate 212 of biochemical cartridge 200. The position of the optical detection components (e.g., the two fluorimeters 136 and spectrometer 140) of point-of-birth instrument 105 correspond to optics interface region 224 of top substrate 212 when biochemical cartridge 200 is installed in point-of-birth instrument 105.

A reel mounting feature 226 (see FIG. 16) is provided in top substrate 212. Reel mounting feature 226 is a through-hole for receiving a foil take-up reel 245 (see FIG. 17 and FIG. 19).

Referring now to FIG. 17 through FIG. 20 is various other views of biochemical cartridge 200 of FIG. 11 and FIG. 12, wherein biochemical cartridge 200 is shown absent cover 214 and thereby revealing more details thereof. Namely, FIG. 17, FIG. 18, FIG. 19, and FIG. 20 show a perspective view, a top view, a rear view, and a side view, respectively, of the biochemical cartridge 200 and absent cover 214. Biochemical cartridge 200 further includes a cover gasket 228, a horizontal reservoir module (HRM) 230 that further includes an HRM mounting plate 239, a pair of mounting posts 242 for holding HRM 230, a foil strip 244 for sealing fluids inside HRM 230, foil take-up reel 245 for winding foil strip 244 off of HRM 230, a reel engaging feature 246 that can be snap-fitted into reel mounting feature 226 of top substrate 212 (see FIG. 16), and a reservoir module capture feature 254 (see FIG. 18 and FIG. 23A). More details of HRM 230 are shown and described hereinbelow with reference to FIG. 33A through 35H.

Referring now to FIG. 21 is a perspective view of the underside of cover 214 of biochemical cartridge 200 shown in FIG. 11 and FIG. 12. Cover 214 further includes a cover rim 248, a well opening 250 for receiving sample input well 216, and a reel capture feature 252 for capturing the top of foil take-up reel 245.

Referring now to FIG. 22A is a perspective view of the underside of biochemical cartridge 200 shown in FIG. 11 and FIG. 12 and absent cover 214. FIG. 22B shows the underside of biochemical cartridge 200 further absent bottom substrate 210. In this view, a substrates gasket 256 and a reaction (or assay) chamber region 258 is revealed. Reaction (or assay) chamber region 258 is the gap between bottom substrate 210 and top substrate 212.

Referring now to FIG. 23A is a perspective view of top substrate 212 in relation to bottom substrate 210 of biochemical cartridge 200 shown in FIG. 11 and FIG. 12. FIG. 23B shows bottom substrate 210 only of biochemical cartridge 200. In this view, an electrode configuration 260 and electrical I/O contacts 262 are shown for supporting digital fluidics capability (i.e., electrowetting). In this example, when biochemical cartridge 200 is installed in point-of-birth instrument 105, electrical I/O contacts 262 are electrically connected to main circuit board 124 of point-of-birth instrument 105. Further, in some examples, dried reagents may be provided at the reaction lanes of electrode configuration 260.

Referring now to FIG. 24A and FIG. 24B is an exploded view and a perspective view, respectively, of stepper motor 150 of point-of-birth instrument 105 in relation to biochemical cartridge 200 shown in FIG. 11 and FIG. 12. Namely, stepper motor 150 includes a motor shaft 156 and spring-loaded adaptor 154 is mounted on motor shaft 156. The distal tip of spring-loaded adaptor 154 is engaged with reel engaging feature 246 of foil take-up reel 245 that that is protruding through top substrate 212. In this way, stepper motor 150 of point-of-birth instrument 105 can be used to rotate foil take-up reel 245 of biochemical cartridge 200, which in turn actuates HRM 230.

Whereas FIG. 24A and FIG. 24B shows a configuration in with the stepper motor engages through the underside of the biochemical cartridge, FIG. 25 shows another configuration in which the stepper motor of the point-of-birth instrument engages through the top side of the biochemical cartridge. In this example, reel engaging feature 246 is in the top side of foil take-up reel 245 and reel engaging feature 246 protrudes through an opening in the cover. Stepper motor 150 has spring-loaded adaptor 154. Then, a motor engaging member 158 is installed in the distal end of spring-loaded adaptor 154. Then, the distal end of motor engaging member 158 is engaged with reel engaging feature 246 of foil take-up reel 245. For another example, see FIG. 35H.

Whereas FIG. 11 through FIG. 23B show an example of biochemical cartridge 200 that supports digital fluidics, FIG. 26 through FIG. 29B show examples of biochemical cartridges 200 for newborn screening that are absent digital fluidics capability. "Absent digital fluidics capability" means absent any electrode configurations for performing electrowetting operations. Absent digital fluidics capability, biochemical cartridge 200 may be, for example, a flow cell. In one example, FIG. 26 shows a perspective view of a biochemical cartridge 200 that is absent digital fluidics capability. Again, biochemical cartridge 200 may include bottom substrate 210, top substrate 212, cover 214, sample input well 216, well cap assembly 220, and recessed or contoured regions 222.

In another example, FIG. 27 and FIG. 28 show a perspective view and top view, respectively, of a biochemical cartridge 200 that is absent digital fluidics capability. Again, biochemical cartridge 200 may include bottom substrate 210, top substrate 212, cover 214, sample input well 216, well cap assembly 220, and recessed or contoured regions 222. Further to the example, FIG. 29A shows a bottom substrate 210 and a top substrate 212 of biochemical cartridge 200 that does not support digital fluidics. Additionally, FIG. 29B shows bottom substrate 210 only of biochemical cartridge 200 that does not support digital fluidics. In this example, bottom substrate 210 is absent any electrode configurations (e.g., electrode configuration 260 of FIG. 23A) and/or electrical I/O contacts (e.g., electrical I/O contacts 262 of FIG. 23A). In these examples, dried reagents may be provided on the surface of bottom substrate 210 and/or top substrate 212.

Referring now to FIG. 30A through FIG. 32B is perspective views of three other examples of cover assemblies that can be used with the presently disclosed biochemical cartridges 200 for newborn screening. Each includes cover 214 that further includes sample input well 216, loading port 218, well cap assembly 220, recessed or contoured regions 222, and cover gasket 228. In these three examples, the overall cover footprints and the shape and placement of recessed or contoured regions 222 may differ.

Referring now to FIG. 33A and FIG. 33B is various views of an example of HRM 230 of biochemical cartridge 200. HRM 230 is provided for holding and then dispensing certain fluids into biochemical cartridge 200. HRM includes a first reservoir 232 for holding a first fluid 234 and a second reservoir 236 for holding a second fluid 238, all sitting atop HRM mounting plate 239. Further, HRM 230 has a front face 240, which is the perimeter area around the openings of first reservoir 232 and second reservoir 236. front face 240 is the surface of HRM 230 that is sealed once HRM 230 is filled with fluid. Further, HRM 230 is not limited to two reservoirs only. HRM 230 can include any number of reservoirs.

In this example, first reservoir 232 is larger than second reservoir 236. For example, first reservoir 232 can hold about 2 mL of fluid while second reservoir 236 can hold about 1 mL of fluid. Further, in this example, HRM 230 can be, for example, about 15 mm deep, about 16 mm high, and about 46 mm long.

In the example of a biochemical cartridge 200 that has digital fluidics capability, first fluid 234 in first reservoir 232 can be filler fluid, such as, but not limited to, a low-viscosity oil such as silicone oil or hexadecane filler fluid. Second fluid 238 in second reservoir 236 can be, for example, a diluent, such as buffer solution, liquid reagent, or water. However, in the example of a biochemical cartridge 200 that does not have digital fluidics capability, oil is not required. Therefore, both first reservoir 232 and second reservoir 236 can be filled with diluent, such as buffer solution, liquid reagent, or water.

Referring now to FIG. 34A is a front perspective view of another example of HRM 230 and showing a front face sealing surface thereof. In this example, HRM 230 is smaller than the HRM 230 shown in FIG. 33A and FIG. 33B. Namely, in this example, first reservoir 232 is still larger than second reservoir 236. However, first reservoir 232 can hold about 1.2 mL of fluid while second reservoir 236 can hold about 0.8 mL of fluid. Further, in this example, HRM 230 can be, for example, about 24 mm deep, about 14 mm high, and about 33 mm long.

Further, in HRM 230 shown in FIG. 34A, the perimeter of, for example, second reservoir 236 is about 6.325 inches (15.84 cm) and front face 240 has a surface area of about 0.279 square inches (1.8 square cm). The width of any portion of front face 240 (i.e., wall thickness) can be, for example, about 2 mm (78.7 mils). It is important to have suitable surface area to ensure reliable sealing. Optionally, a lip (not shown) can be provided around the edge of front face 240 in order to increases the surface area for bonding foil strip 244.

With respect to any HRM 230, HRM 230 has a certain dispensing angle for optimal dispensing at a desired rate by gravity only. For example, FIG. 34B shows a cross-sectional view of HRM 230 and showing a dispensing angle $\alpha$. The dispensing angle $\alpha$ can be from about 13 degrees to about 17 degrees in one example, or is about 15 degrees in another example. Again, HRM 230 is not limited to two reservoirs only. Further, the respective dispensing angles $\alpha$ for the multiple reservoirs within HRM 230 can be the same or can be different.

HRM 230 can be formed, for example, of molded plastic. For example, HRM 230 can be formed of high-density polyethylene (HDPE), cyclic olefin polymer (COP), cyclic olefin copolymer (COC), or polypropylene (PP). Further, to assist the flow of liquid by gravity out of HRM 230 and/or to reduce pinning of liquids, (1) the surfaces inside first reservoir 232 and second reservoir 236 can be coated with hydrophobic material, (2) the surfaces inside first reservoir 232 and second reservoir 236 can have a texture (e.g., 110 μm textured surface), and/or (3) a small amount of oil (e.g., silicone oil) can be added to the diluent (e.g., 50 μL oil to 200 μL diluent).

Figure 35A:
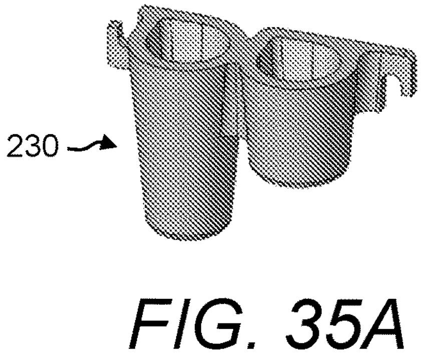
Figure 35B:
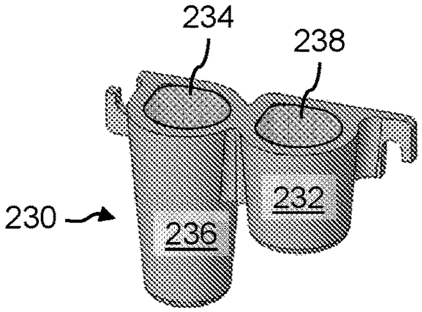
Figure 35C:
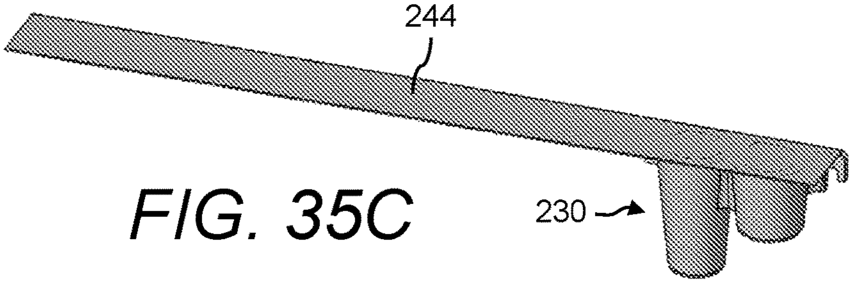
Figure 35D:
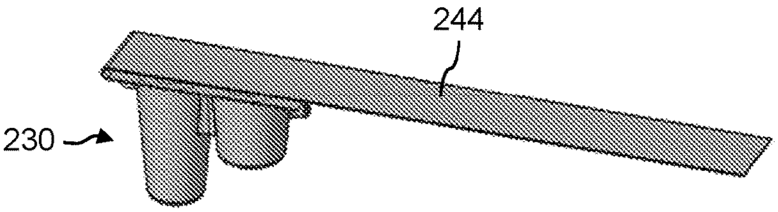
Figure 35E:
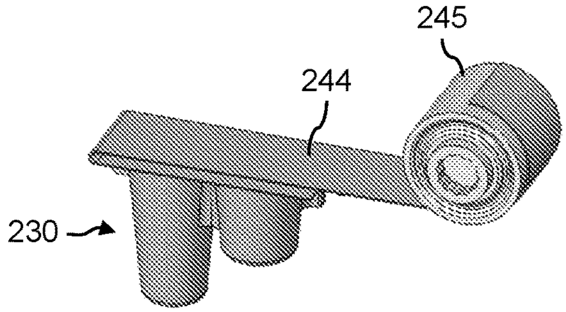
Figure 35F:
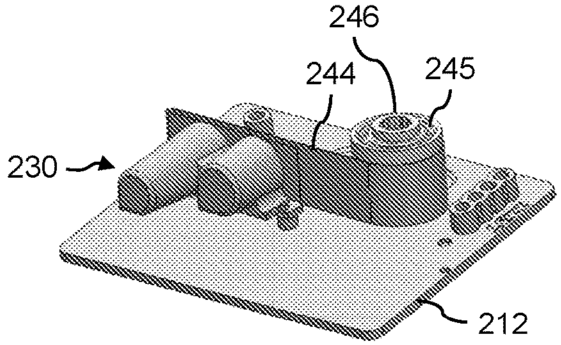
Figure 35G:
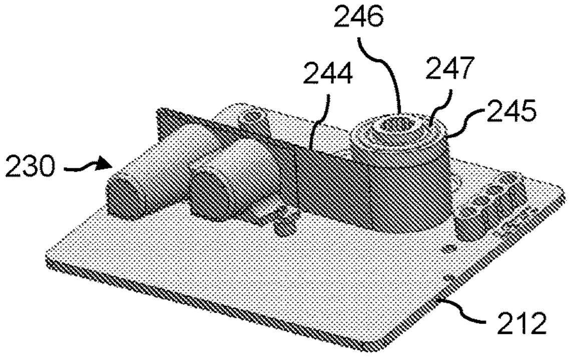
Figure 35H:
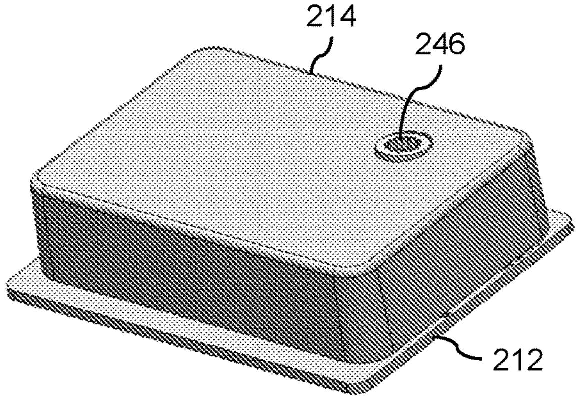

Referring now to FIG. 35A through FIG. 35H is an example of a process of deploying HRM 230 of the presently disclosed biochemical cartridge 200 for newborn screening. Referring now to FIG. 35A, a HRM 230 is provided. Next and referring now to FIG. 35B, first reservoir 232 is filled with first fluid 234 and second reservoir 236 is filled with second fluid 238. Next and referring now to FIG. 35C, HRM 230 is sealed with foil strip 244. Namely, foil strip 244 is adhered to front face 240 of HRM 230. Foil strip 244 is installed with an excess length or tail extending to one side. Next and referring now to FIG. 35D, the excess length or tail of foil strip 244 is folded back on itself and over and past HRM 230. Next and referring now to FIG. 35E, the excess length or tail of foil strip 244 is attached to foil take-up reel 245. Next and referring now to FIG. 35F, the combination of HRM 230 with foil strip 244 and foil take-up reel 245 are attached to top substrate 212. Next and referring now to FIG. 35G, an O-ring 247 is placed atop foil take-up reel 245. Next and referring now to FIG. 35H, cover 214 is placed atop top substrate 212 and thereby capturing and securing foil take-up reel 245 in place. Foil strip 244 can be, for example, an aluminum foil strip that has a low moisture vapor transmission rate (MVTR) so that HRM 230 can be stored in the sealed state for extended periods of time without losses. Further, foil strip 244 can be a polyethylene terephthalate (PET)-backed foil for added strength. In one example, the adhesive holding foil strip 244 to HRM 230 is PE250 adhesive.

Together, HRM 230 with its foil strip 244 along with foil take-up reel 245 form the liquid delivery system of biochemical cartridge 200. Referring now again to FIG. 24A, FIG. 24B, FIG. 25, and FIG. 35A through FIG. 35H, the operation of biochemical cartridge 200 with respect to dispensing liquid from HRM 230 is as follows. When biochemical cartridge 200 is inserted into point-of-birth instrument 105, stepper motor 150 is engaged with foil take-up reel 245 of biochemical cartridge 200 and HRM 230 is still in the sealed state. Then, to dispense liquid from HRM 230, stepper motor 150 is activated and foil strip 244 begins to wind onto foil take-up reel 245. In so doing, the foil strip 244 on first reservoir 232 begins to slowly peel away and thereby slowly releases first fluid 234, which flows into the reaction (or assay) chamber-portion of biochemical cartridge 200. Eventually, as stepper motor 150 continues to run, the foil strip 244 on second reservoir 236 is also slowly peeled away and thereby slowly releases second fluid 238, which flows into the reaction (or assay) chamber-portion of biochemical cartridge 200.

Using stepper motor 150, the timing of liquid released from second reservoir 236 after liquid is released from first reservoir 232 can be controlled. For example, it may be desirable for the oil to fully deploy before dispensing the diluent. Further, because first reservoir 232 and second reservoir 236 are essentially mounted on their sides, venting and opening are achieved using the same foil strip 244. Further, the design of HRM 230 reduces or entirely eliminates the risk of bubbles forming during dispensing. Further, the design of HRM 230 reduces or entirely eliminates dead volume with the reservoirs.

For optimal pulling force (e.g., minimum torque) that ensures reliable removal of foil strip 244 from HRM 230, the path of the excess length or tail of foil strip 244 leading toward foil take-up reel 245 is substantially parallel to the plane of front face 240 of HRM 230. This can be achieved by arranging the outer surface of foil take-up reel 245 substantially tangent to the plane of front face 240 of HRM 230.

Referring now to FIG. 36 is an example of a functional block diagram of, for example, point-of-birth instrument 105 of FIG. 2A and FIG. 2B. Point-of-birth instrument 105 includes main circuit board 124. Main circuit board 124 includes a microcontroller 610, a USB port 612, a CAN port 614, accel MEMS, LEDs 618, power I/O 128 (e.g., power input port 128), an impedance detector 620, an interlock and timer 622 (e.g., interlock circuit and watchdog timer), an FPGA 624, an SDRAM 626, an EEPROM 628, electrowetting control 630 for driving a biochemical cartridge 200 with digital fluidics capability, thermal control 632, a motor 1 control 634 for controlling HRM stepper motor 150, and a motor 2 control for controlling cartridge engage stepper motor 144.

Certain other functions are in communication with main circuit board 124, such as, but not limited, an illuminator 638 associated with spectrometer 140, the two fluorimeters 136, other LEDs 640, certain sensors and heater 642, and certain position switches 646. Barcode reader 116 is also in communication with main circuit board 124. Barcode reader 116 further includes SVDCIN 648 and a USB port 650. Additionally, power supply 130 (e.g., power supply assembly 130) provides power to main circuit board 124 and all other active components. Further, smart device 190 (not shown) can be in communication with main circuit board 124 using any wired or wireless means.

Referring now to FIG. 37 through FIG. 52 is an example the graphical user interface (GUI) 700 of the presently disclosed point-of-birth system 100, point-of-birth instrument 105, and biochemical cartridge 200 for newborn screening. GUI 700 includes, for example, an upper display panel 710 and a lower display panel 715. Upper display panel 710 is used to present more global information and controls to the user, while lower display panel 715 is used to present more specific selected information and controls to the user. GUI 700 can include any standard user interface controls and display formats. GUI 700 can be displayed on a smart display, such as smart device 190. Namely, GUI 700 maybe launched using NBS mobile app 192 on smart device 190.

Figure 37:
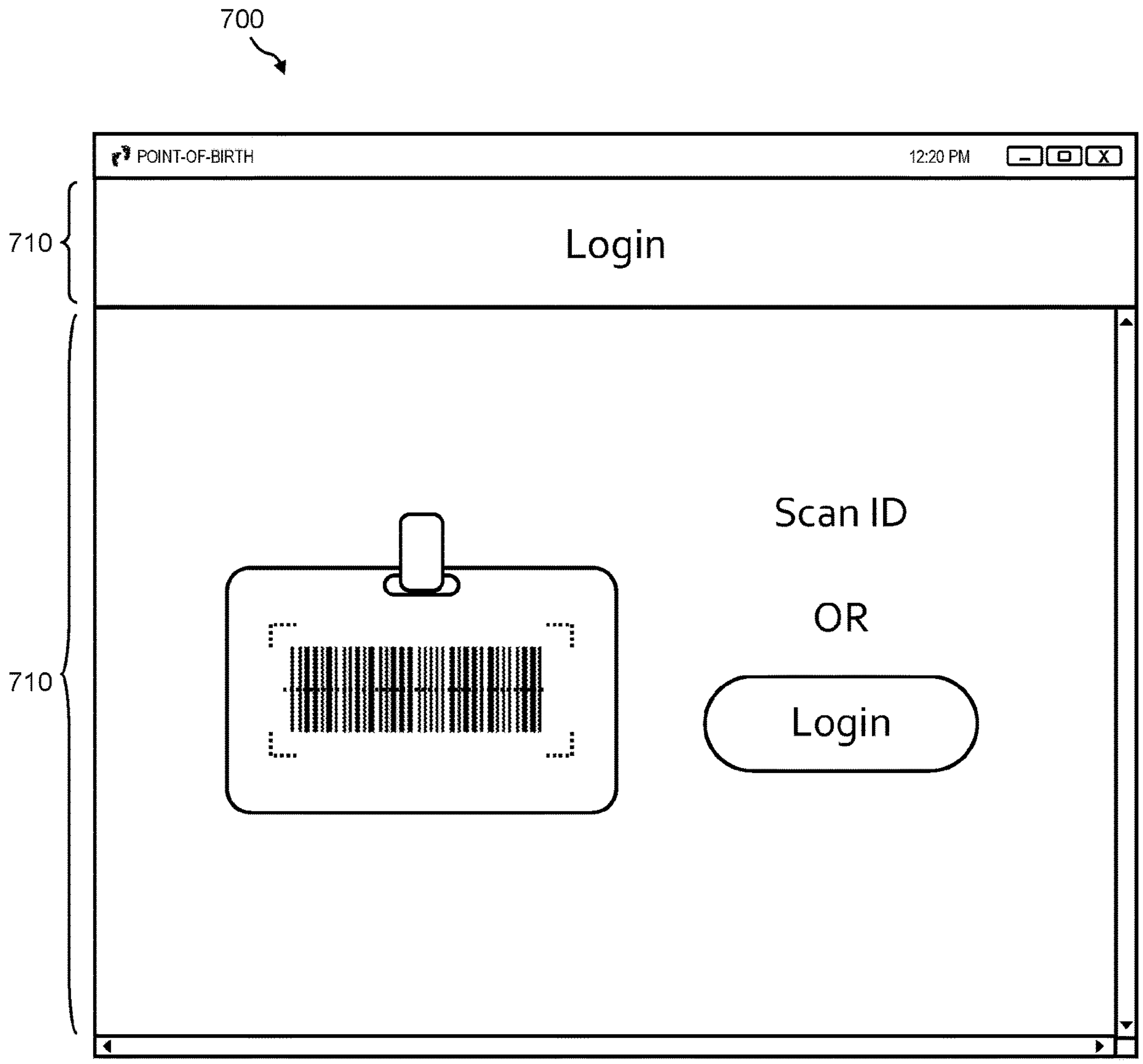

GUI 700 in FIG. 37 shows a login screen by which the user may login manually by entering a user ID and password. Alternatively, the user may login by scanning his/her ID badge using barcode reader 116 of point-of-birth instrument 105.

Figure 38:
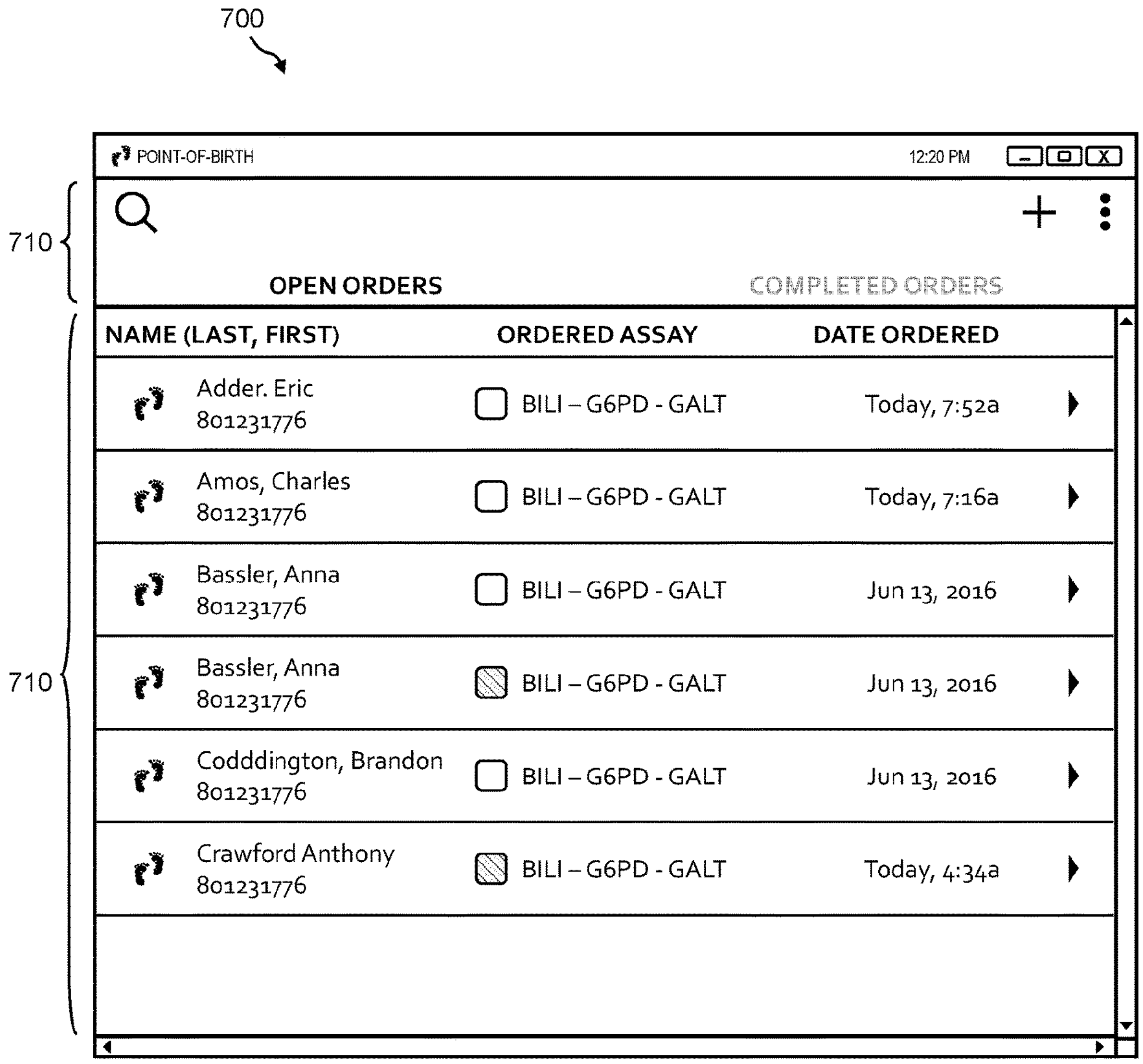

GUI 700 in FIG. 38 shows a home page that includes selection tabs for OPEN ORDERS and CLOSED ORDERS in lower display panel 715. In FIG. 38, the OPEN ORDERS tab is selected. A list is presented showing patient NAME, ASSAY ORDERED, and DATE ORDERED.

Figure 39:
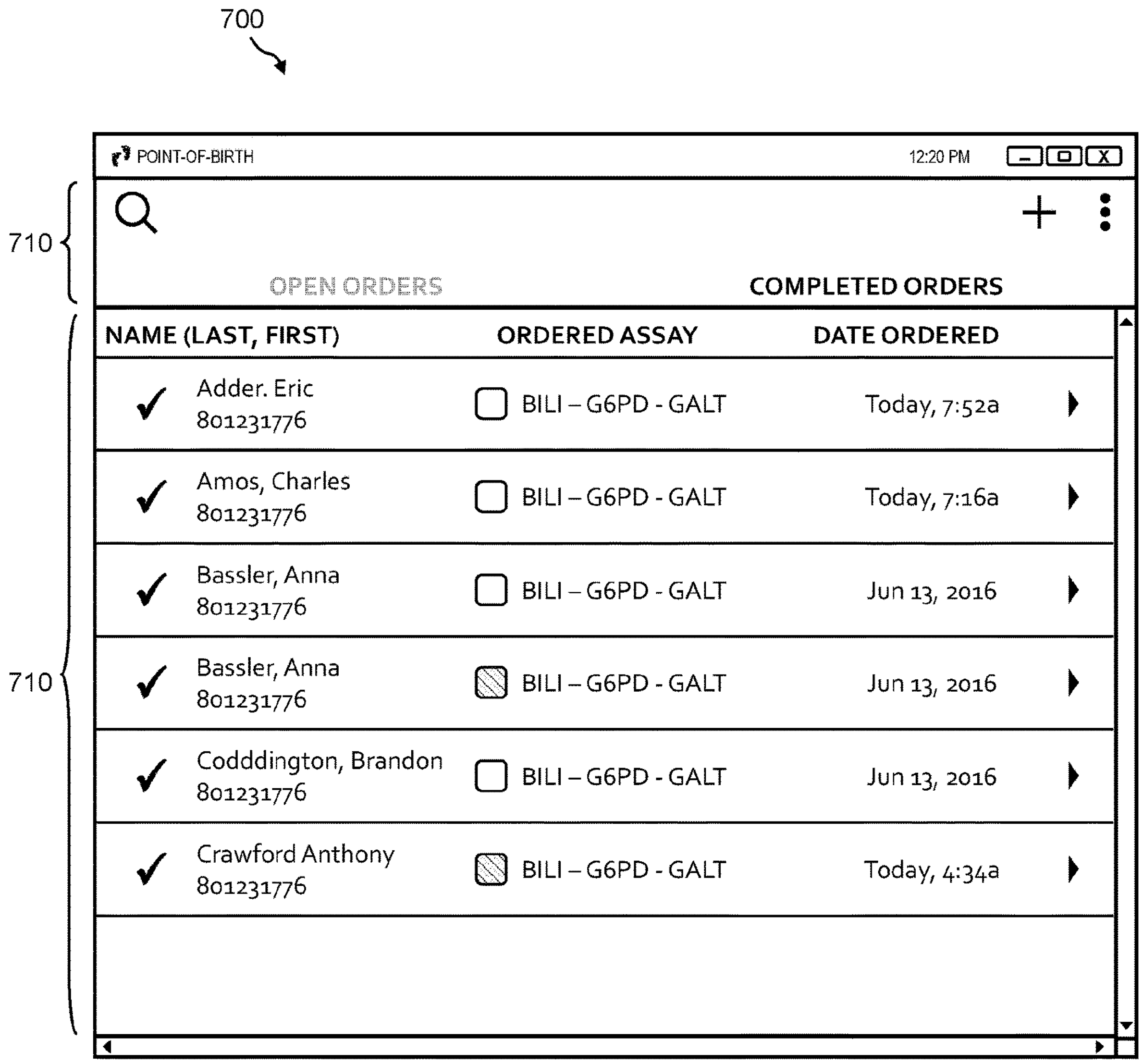

GUI 700 in FIG. 39 shows the home page with the CLOSED ORDERS tab selected. Again, a list is presented showing patient NAME, ASSAY ORDERED, and DATE ORDERED.

By selecting a name from the OPEN ORDERS list, tests can be initiated and run. For example, GUI 700 in FIG. 40 indicates to the user the first step of running a newborn screening test, which is to scan the barcode on the selected biochemical cartridge 200, using barcode reader 114 of point-of-birth instrument 105. Further, patient information is displayed in either a collapsed or expanded view.

Figure 41:
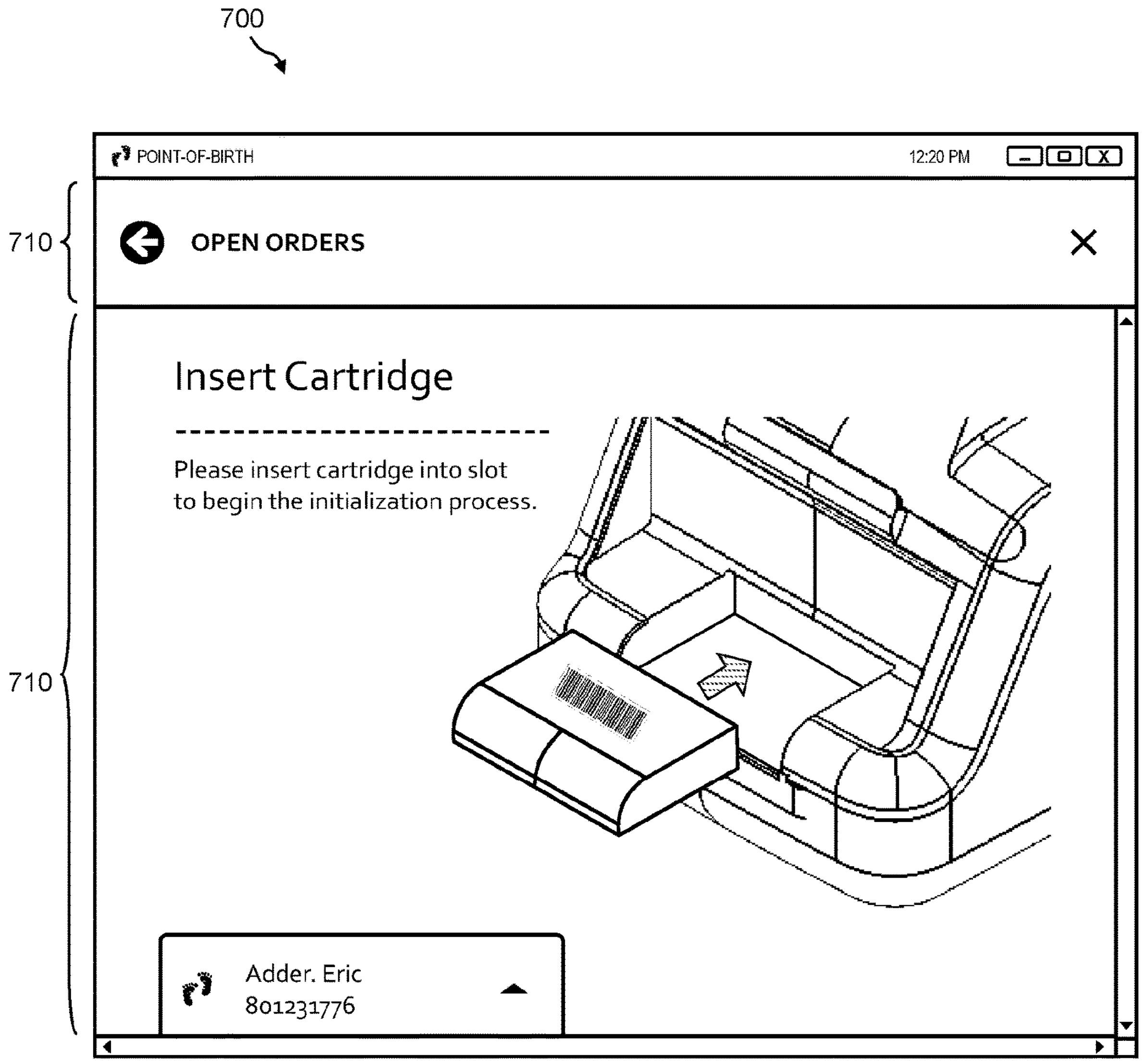

GUI 700 in FIG. 41 indicates to the user the next step of running a newborn screening test, which is to insert biochemical cartridge 200 into point-of-birth instrument 105. Again, patient information is displayed.

Figure 42:

Once biochemical cartridge 200 is inserted into point-of-birth instrument 105, the initialization process begins. GUI 700 in FIG. 42 shows the status of the initialization process. Again, patient information is displayed.

Figure 43:
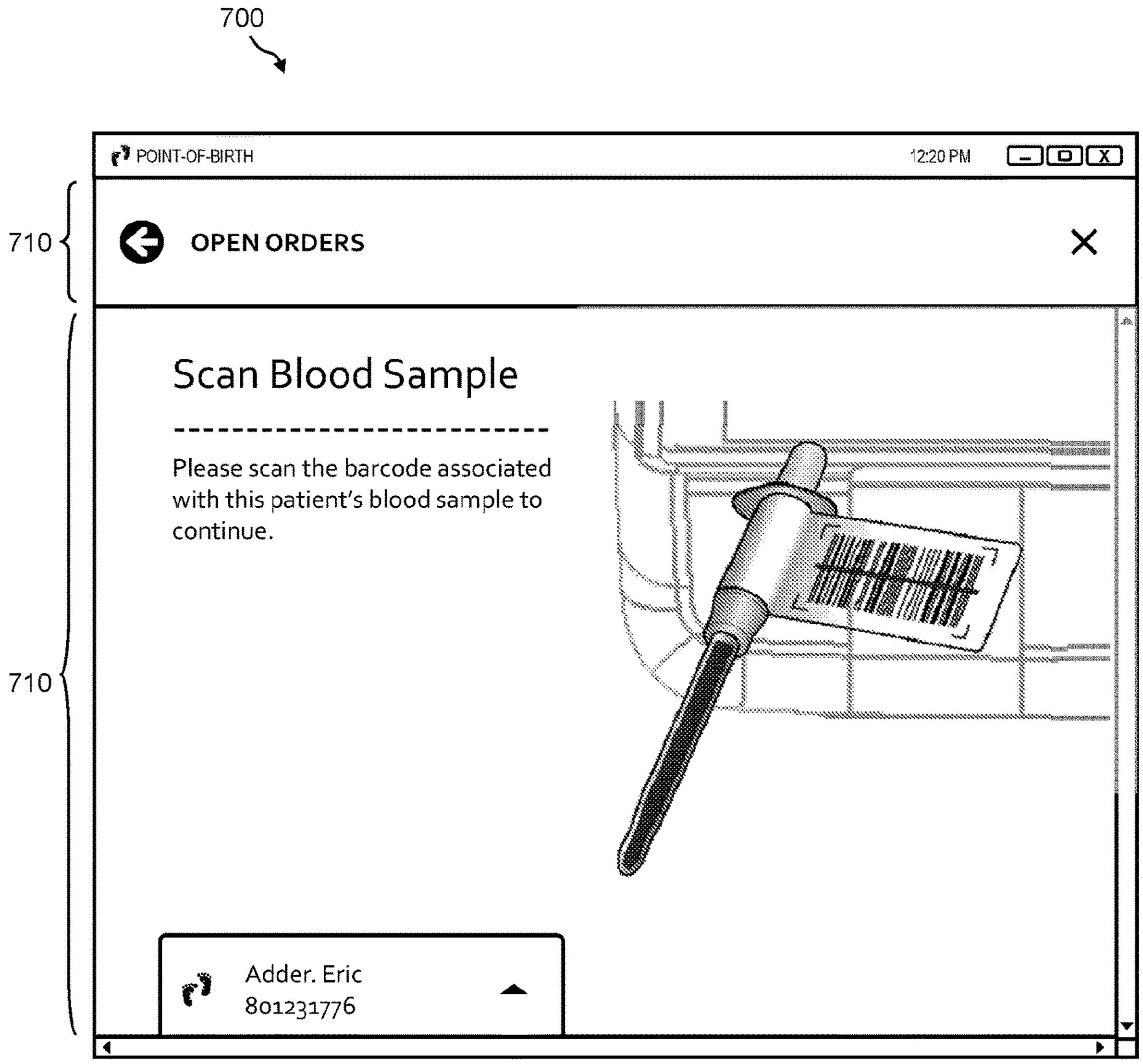
Figure 44:
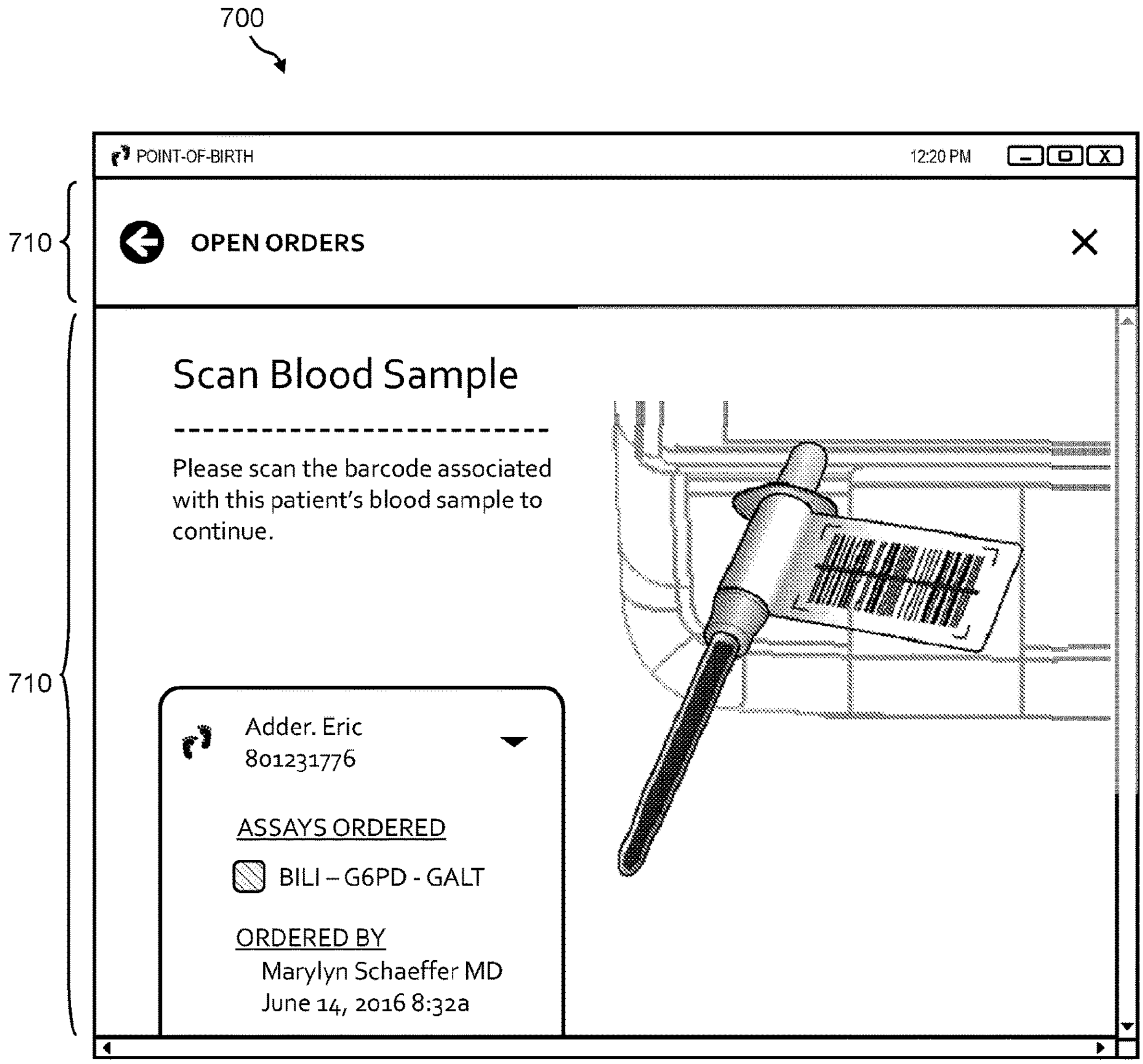

GUI 700 in FIG. 43 indicates to the user the next step of running a newborn screening test, which is to scan the barcode on the container holding the sample of the selected patient, using barcode reader 116 of point-of-birth instrument 105. Again, patient information is displayed in a collapsed view. FIG. 44 shows an expanded view of the patient information.

Figure 45:
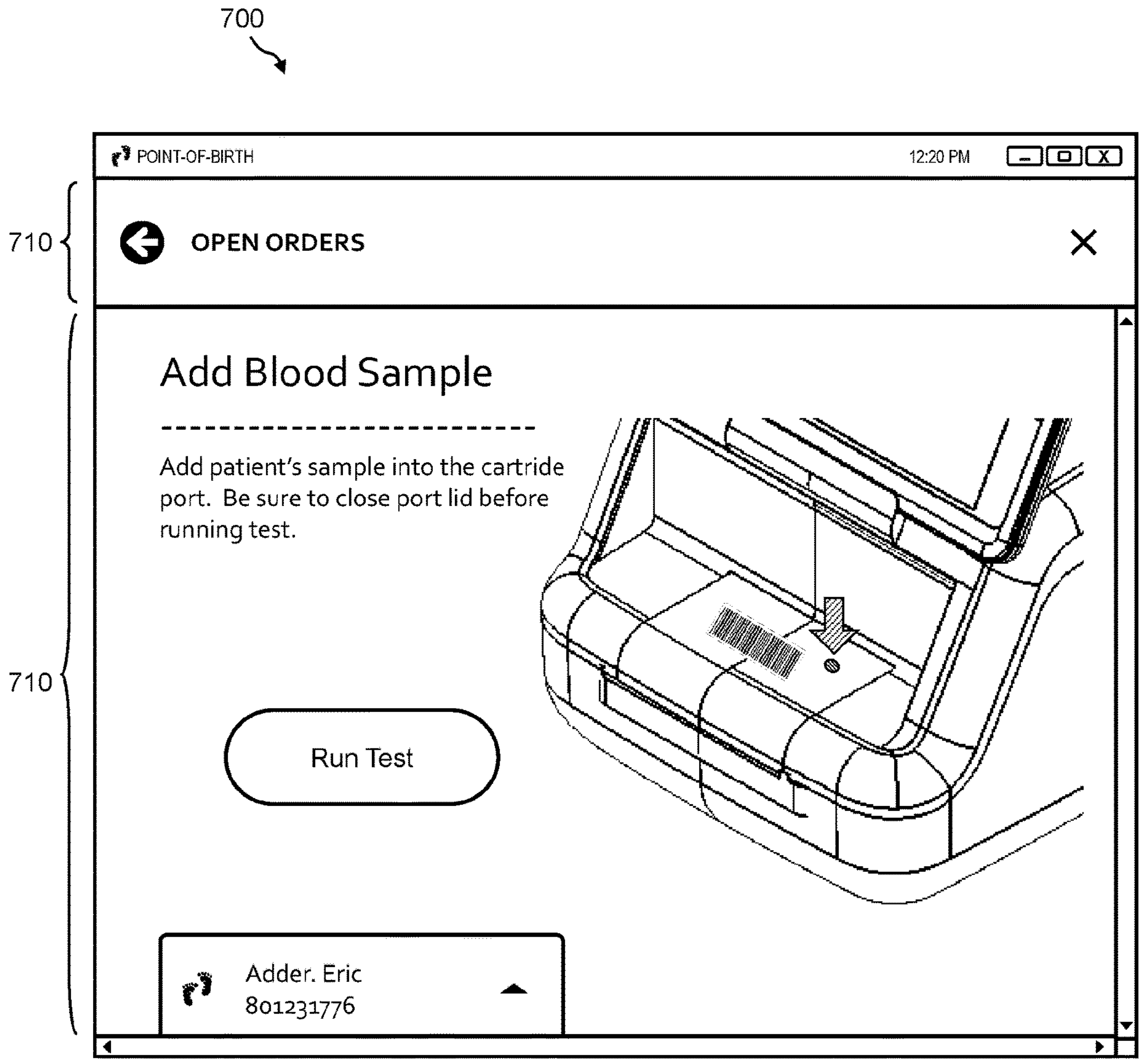

GUI 700 in FIG. 45 indicates to the user the next step of running a newborn screening test, which is to add an amount of the patient's sample to biochemical cartridge 200 and then select the "Run Test" button to initiate the test. Again, patient information is displayed.

Figure 46:

GUI 700 in FIG. 46 indicates to the user a verification step of the amount of sample added.

Figure 47:
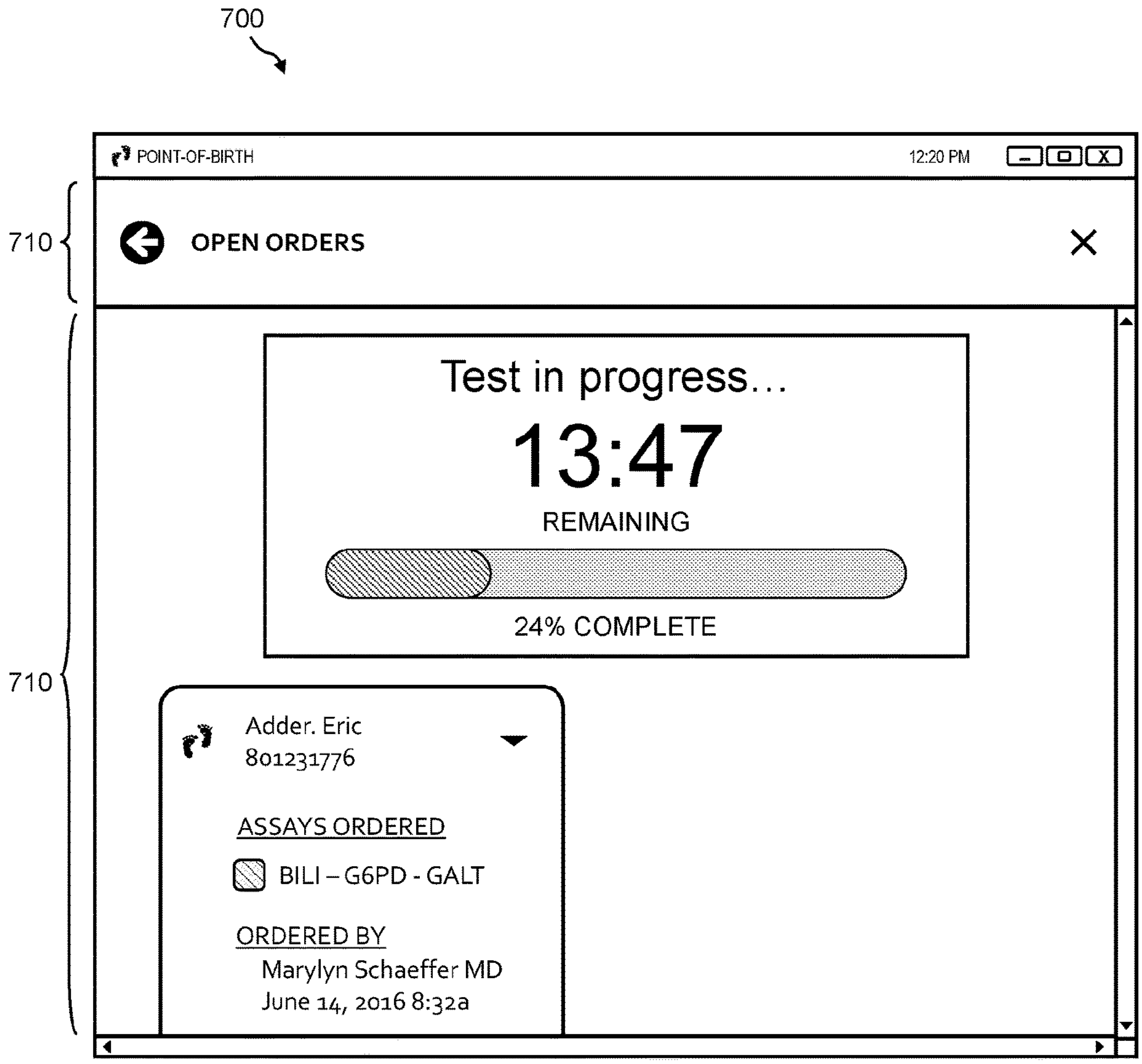

GUI 700 in FIG. 47 indicates to the user that the test is running and shows the status thereof. For example, the amount of test time remaining can be indicated along with the percent complete. Again, patient information is displayed.

Figure 48:
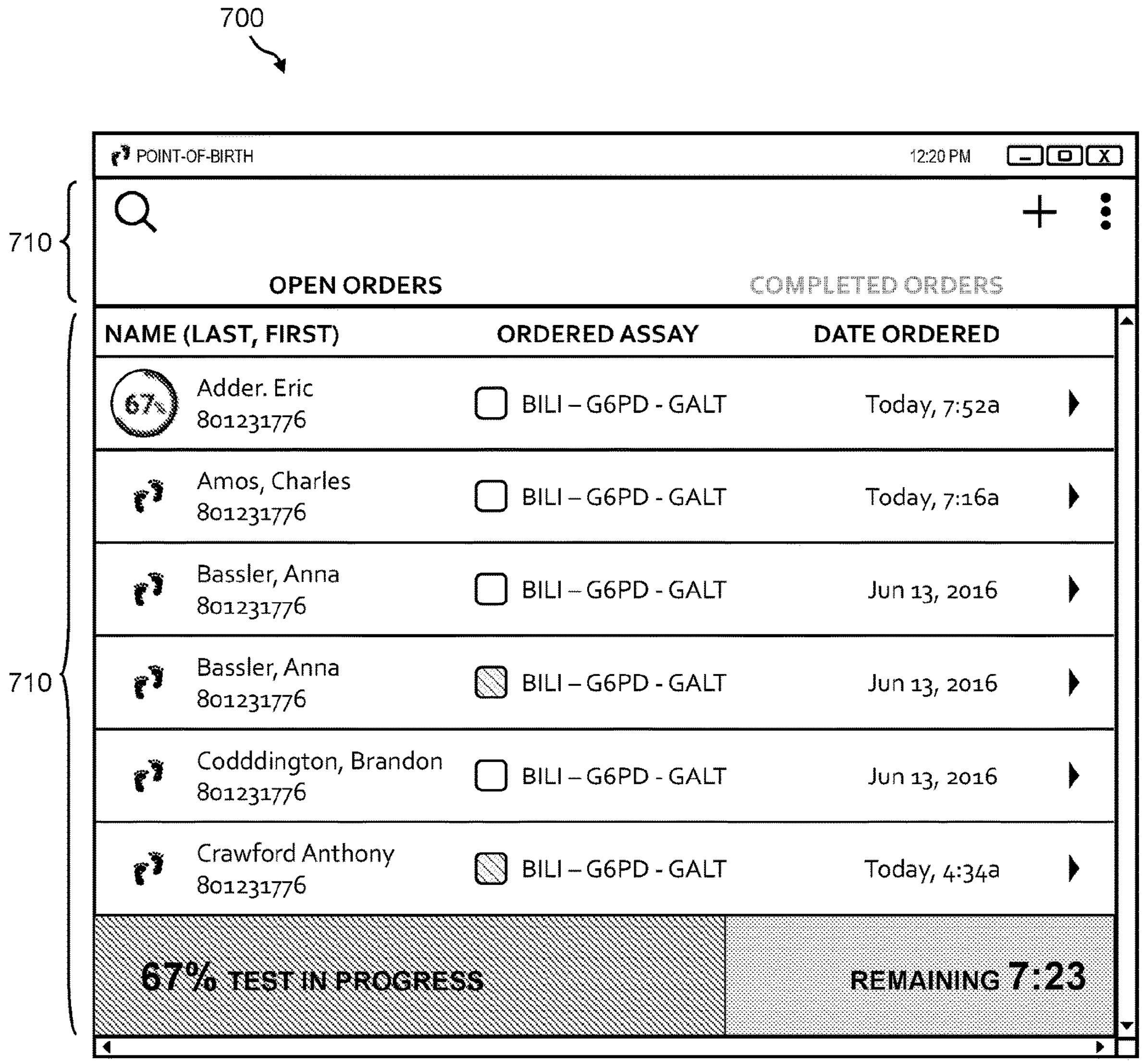

GUI 700 in FIG. 48 shows another way of indicating the status of running tests. Namely, GUI 700 in FIG. 48 shows the home page wherein the progress can be indicated via a percent symbol beside a patient's name and/or via a bar along the bottom of lower display panel 715.

Figure 49:
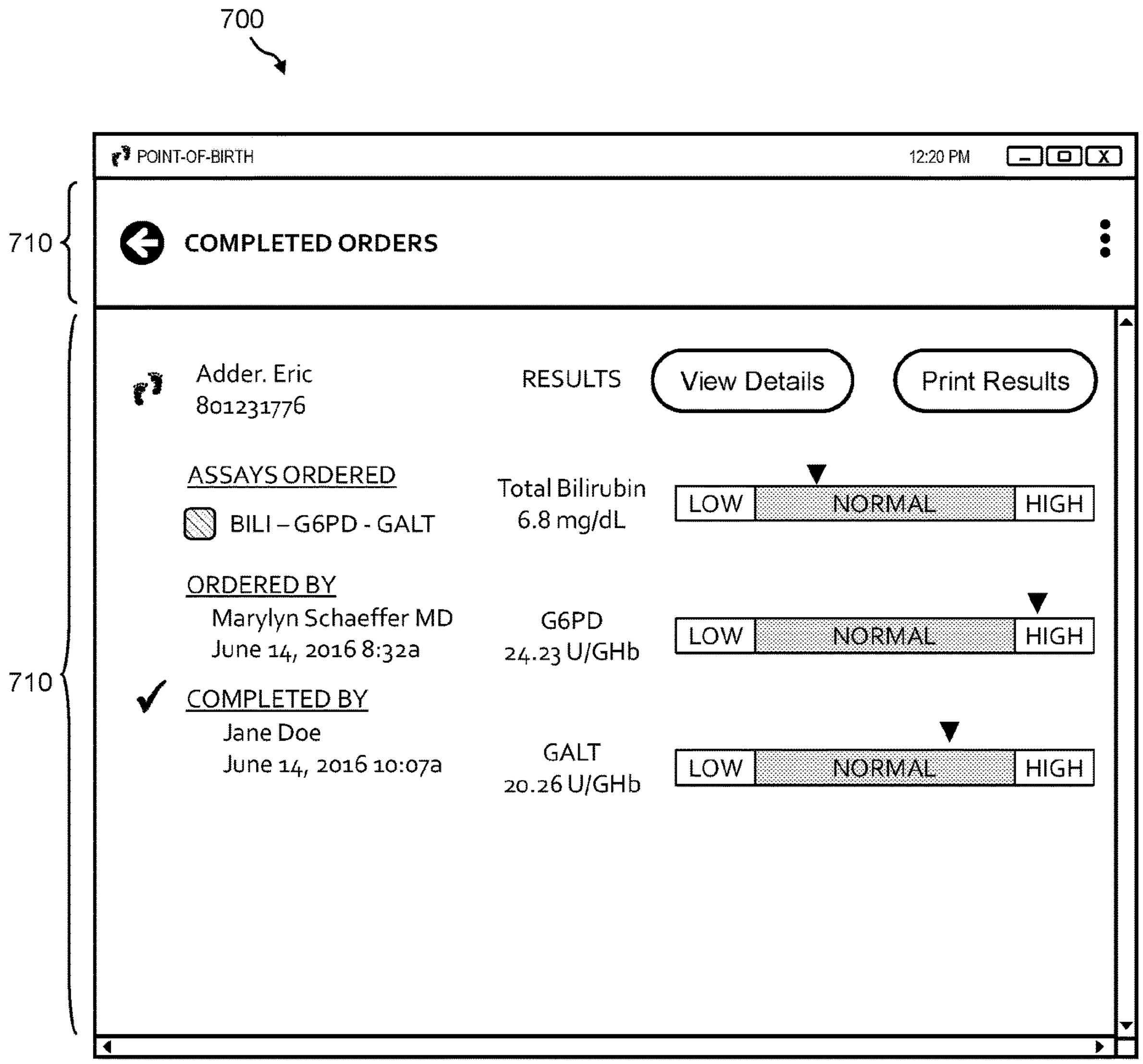

By selecting a patient from the COMPLETED ORDERS list, GUI 700 in FIG. 49 indicates to the user the test results. In one example, visuals can be provided to indicate the levels of markers detected. Further, the user may select to see more detailed information or to print the information.

Figure 50:
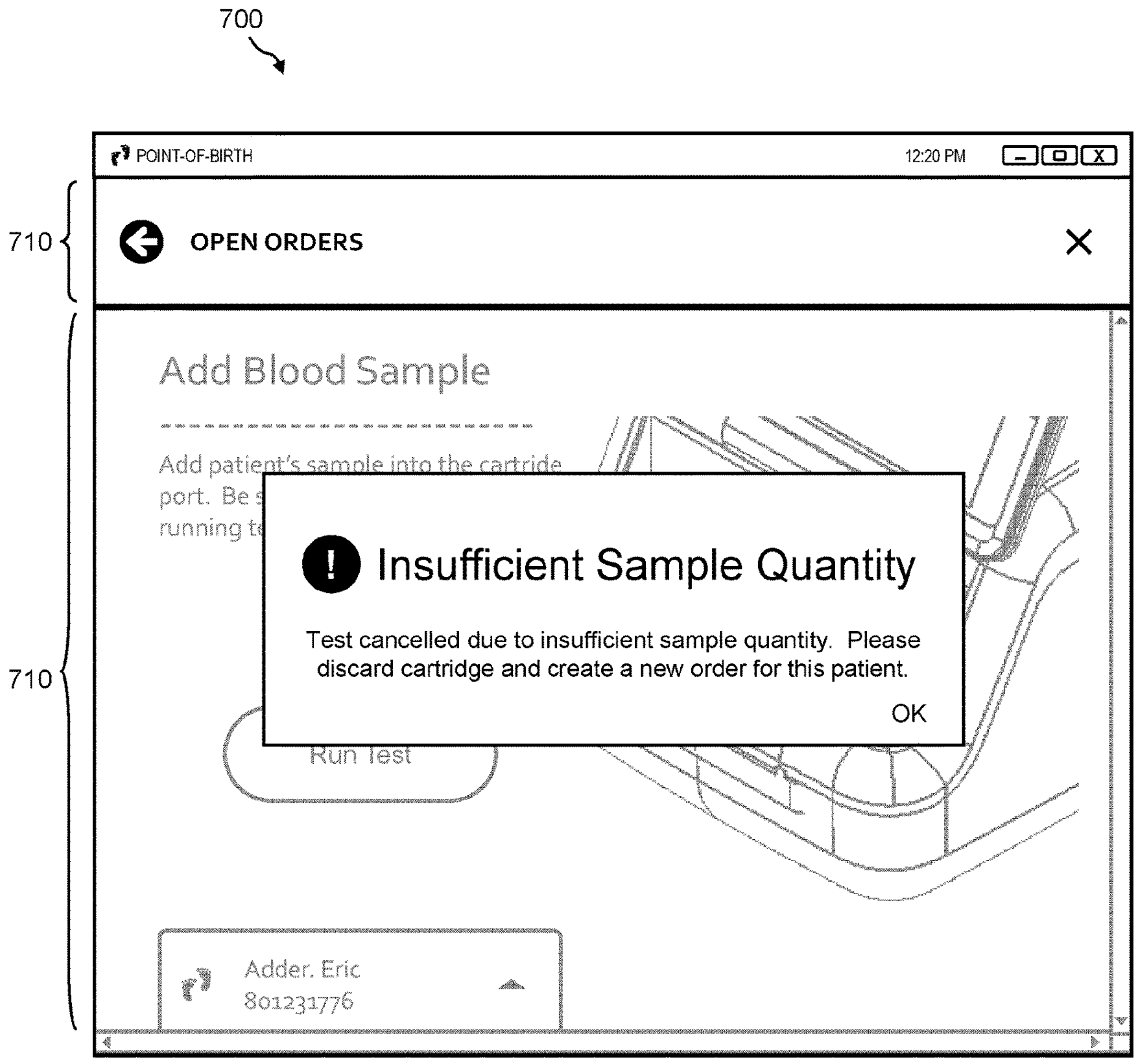

Certain error conditions may arise when running a newborn screening test. IN one example, GUI 700 in FIG. 50 shows an alert that can be generated if the amount of sample loaded into biochemical cartridge 200 is not sufficient to perform the test. In this example, GUI 700 in FIG. 50 shows an "Insufficient Sample Quantity" alert and the test is cancelled.

Figure 51:
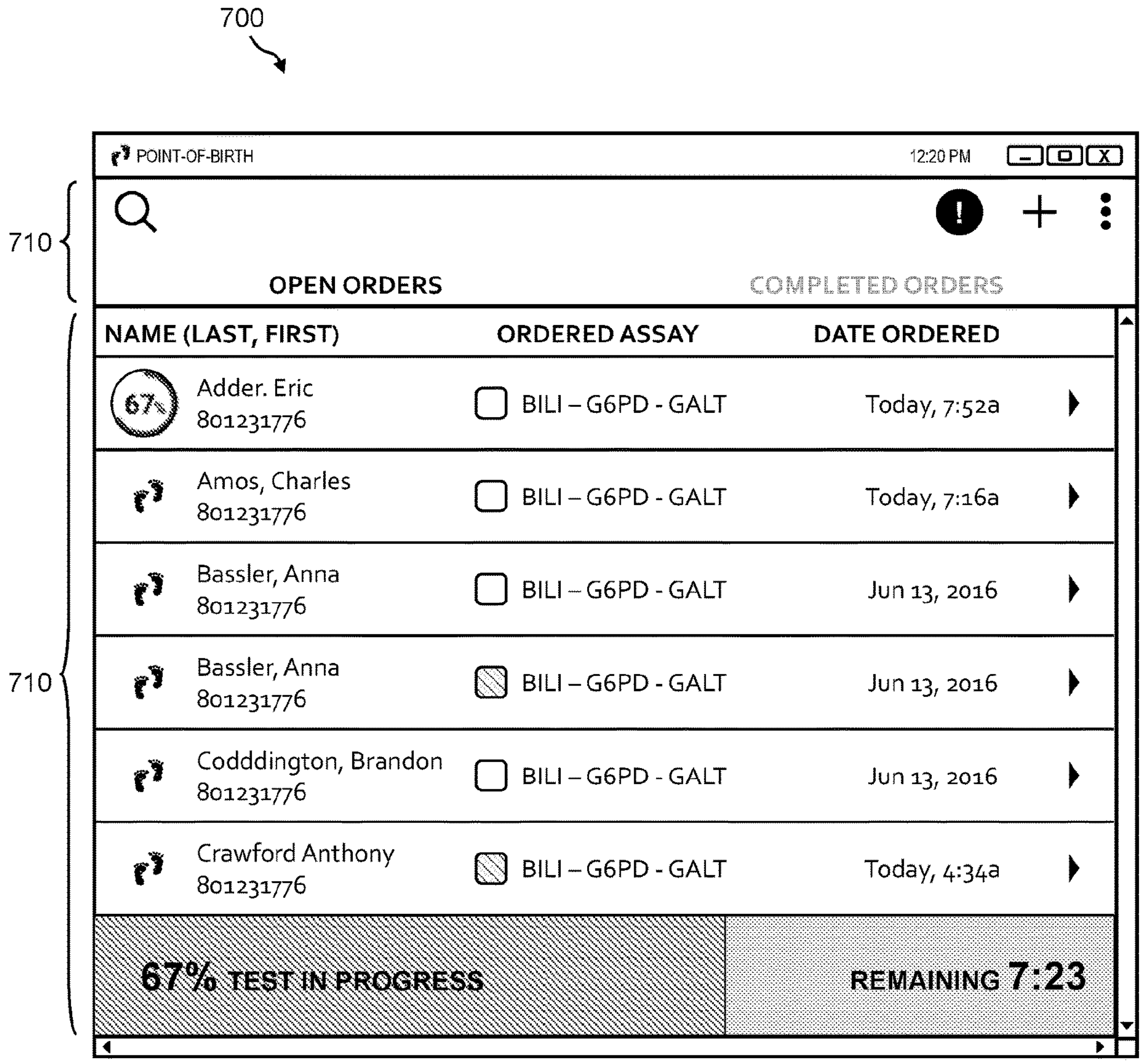
Figure 52:
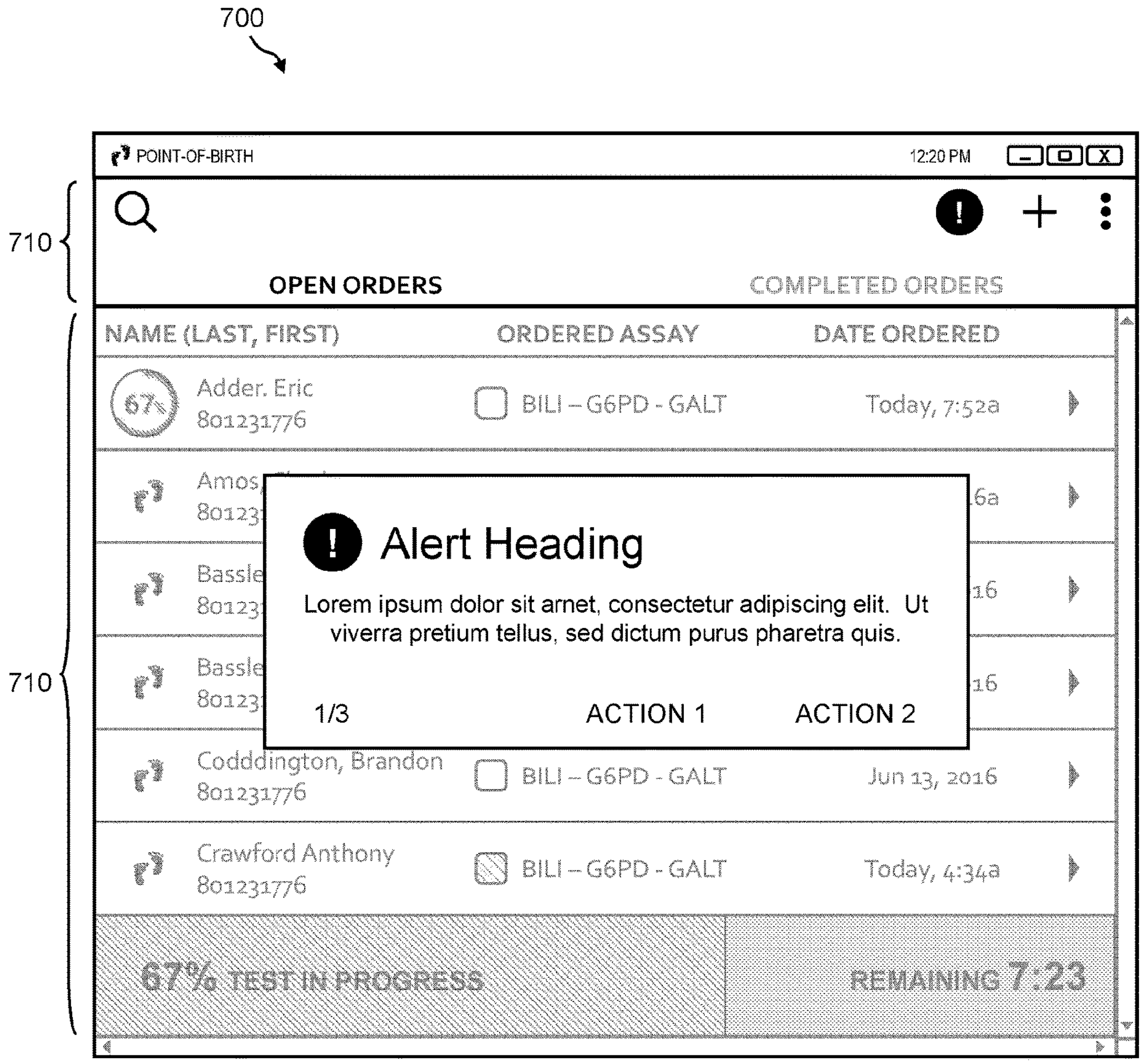

GUI 700 in FIG. 51 shows that alerts can be displayed in other ways. For example, global alerts can be displayed in upper display panel 710. A user may select the alert to find out more information. Multiple global alerts can be present and reviewed at the user's discretion. For example, GUI 700 in FIG. 52 shows an example of reviewing a global alert.

GUI 700 of the presently disclosed point-of-birth system 100 is not limited to only those views, designs, and information shown in FIG. 37 through FIG. 52. These are exemplary only. GUI 700 can include any views, designs, and information.

Referring now to FIG. 53 is a front view of an example of the point-of-birth instrument 105 that includes a smart display that is a built-in display 132. The operation of point-of-birth system 100 and more particularly of point-of-birth instrument 105 is not limited to using NBS mobile app 192 on smart device 190. Any smart display may be used in connection with the present invention. For example, in other embodiments, point-of-birth instrument 105 has a built-in display 132, which may be, for example, a touch screen. Display 132 can be used to present substantially the same information shown in GUI 700 of FIG. 37 through FIG. 52. Accordingly, in this example, the presence of smart device 190 in point-of-birth system 100 is not required.

Referring now to FIG. 54 is a flow diagram of an example of a method 800 of using the presently disclosed point-of-birth system 100 for newborn screening. Method 800 may include, but is not limited to, the following steps.

At a step 810, the point-of-birth application is launched and the user logs in. For example, NBS mobile app 192 on smart device 190 is launched. Then, using GUI 700, the user logs in, as shown and described for example in FIG. 37.

At a step 815, the user views the home page, which shows open orders and/or completed orders. For example, using GUI 700, the user views OPEN ORDERS and/or COMPLETED ORDERS, as shown and described for example in FIG. 38 and FIG. 39.

At a step 820, the user selects a patient of interest from the open orders view. For example, using GUI 700, the user selects the patient to be screened from the OPEN ORDERS view, as shown and described for example in FIG. 38.

Figure 40:
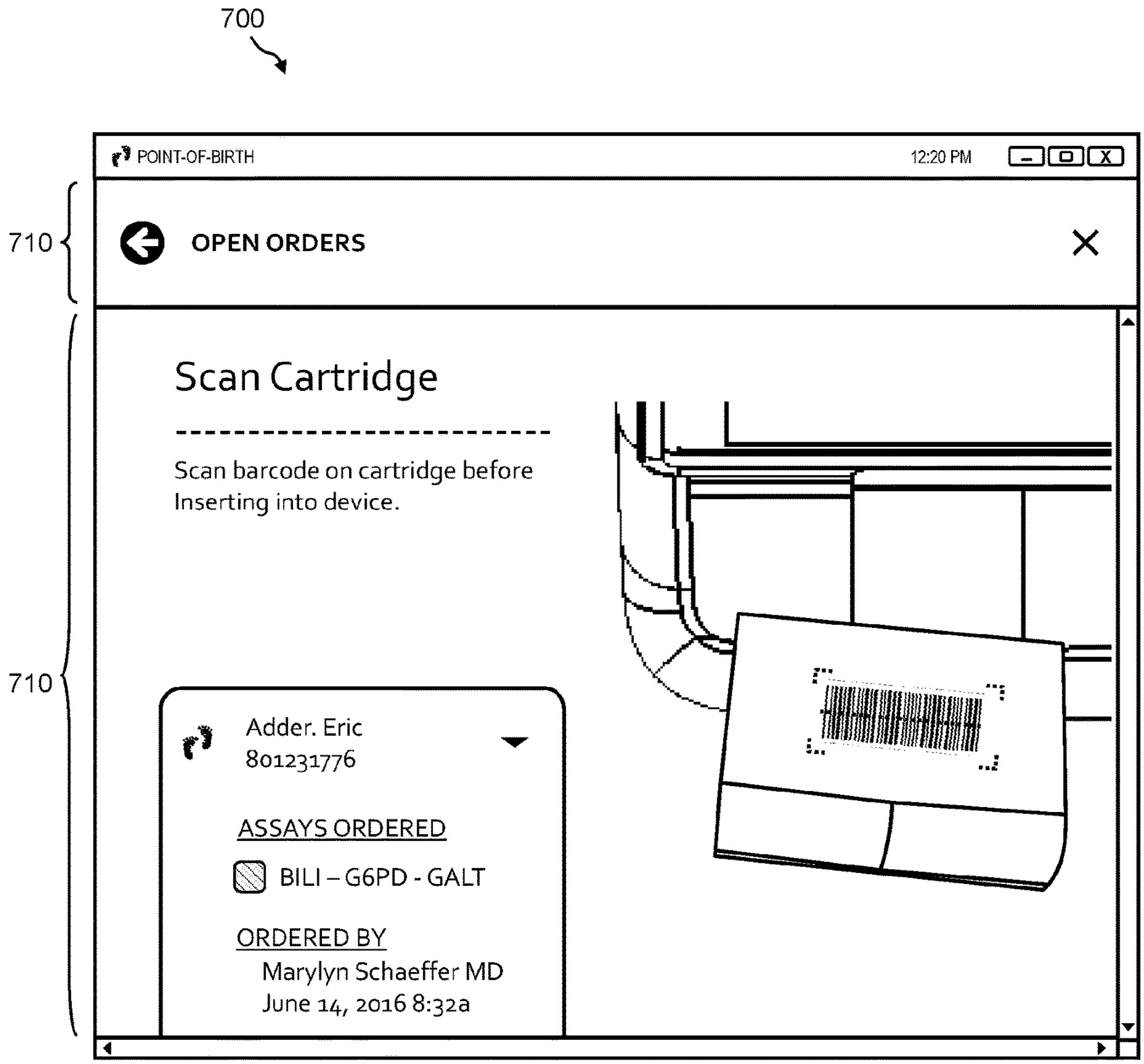

At a step 825, the user acquires and scans the biochemical cartridge that is suitable for the selected patient. For example, the user acquires the biochemical cartridge 200 that is suitable for the selected patient. Then, prompted by instructions in GUI 700 as shown in FIG. 40, the user scans the barcode of biochemical cartridge 200 using barcode reader 116 of point-of-birth instrument 105.

At a step 830, the user inserts the selected biochemical cartridge into the point-of-birth instrument. For example, prompted by instructions in GUI 700 as shown in FIG. 41, the user inserts the selected biochemical cartridge 200 into the point-of-birth instrument 105.

At a step 835, the user waits for the biochemical cartridge to initialize. For example, prompted by instructions in GUI 700 as shown in FIG. 42, the user waits for biochemical cartridge 200 to initialize.

At a step 840, the user acquires and scans the container of sample fluid of the selected patient. For example, the user acquires the container of sample fluid of the selected patient. Then, prompted by instructions in GUI 700 as shown in FIG. 43 and/or FIG. 44, the user scans the barcode on the sample container using barcode reader 116 of point-of-birth instrument 105. In one example, the sample container is a pipette.

At a step 845, the user loads the sample fluid of the selected patient into the biochemical cartridge. For example, prompted by instructions in GUI 700 as shown in FIG. 45, the user opens sample input well 216 of biochemical cartridge 200 by flipping open well cap assembly 220. Then, the user pipettes a volume of sample fluid into loading port 218 of sample input well 216. For example, the user closes input well 216 of biochemical cartridge 200 by flipping closed well cap assembly 220.

At a decision step 850, it is determined whether there is enough sample fluid present in biochemical cartridge 200. For example, instrumentation of point-of-birth instrument 105 performs analysis to determine the amount of sample fluid present in biochemical cartridge 200. If enough sample fluid is present, then method 800 proceeds to a step 855. However, if an insufficient amount of sample fluid is present, then method 800 ends and the test is cancelled, for example, as indicated in GUI 700 as shown in FIG. 50.

At a step 855, the newborn screening test is initiated within point-of-birth instrument 105.

At a step 860, the user monitors the progress of the newborn screening test. For example, the progress of the test can be indicated in GUI 700 as shown in FIG. 47 and FIG. 48.

At a step 865, the user views the newborn screening test results. For example, for any tests that are complete, the user may view the test results, for example, as shown in GUI 700 in FIG. 49. Further, using NBS mobile app 192 on smart device 190, any test results can be logged and distributed to any authorized parties. Thus, using NBS mobile app 192 on smart device 190, test results may be communicated to the user (by viewing the result on smart device 190) as well as communicated to other authorized parties (by distributing the results using smart device 190).

Referring now to FIG. 55 is an example of the presently disclosed point-of-birth system 100 that includes a laptop computer as the smart display. For example, in place of smart device 190, point-of-birth system 100 can use a laptop computer 195 that is in communication with point-of-birth instrument 105 using any wired or wireless means. In this example, laptop computer 195 uses a NBS desktop application 192 in place of NBS mobile app 192. Like smart device 190, using laptop computer 195 allows the portability of point-of-birth system 100.

While heretofore with reference to FIG. 2A through FIG. 53 only biochemical screening has been described in point-of-birth system 100, point-of-birth system 100 can include physiological screening in addition to biochemical screening. For example, and referring now to FIG. 56 through FIG. 59, examples are provided of the presently disclosed point-of-birth system 100 that support both physiological screening and biochemical screening. In one example, FIG. 56 shows a point-of-birth system 100 that includes point-of-birth instrument 105, smart device 190, and biochemical cartridge 200 as previously described. Additionally, the point-of-birth system 100 includes a newborn pulse oximetry mechanism 900. In this example, newborn pulse oximetry mechanism 900 is in direct communication with smart device 190. Features of NBS mobile app 192 can include processing information from/to the newborn pulse oximetry mechanism 900. In another example, FIG. 57 shows a configuration in which the newborn pulse oximetry mechanism 900 is physically connected to point-of-birth instrument 105 instead of to smart device 190. In this example, point-of-birth instrument 105 passes information from the newborn pulse oximetry mechanism 900 to the NBS mobile app 192 on smart device 190 for processing.

In yet another example, FIG. 58 shows a point-of-birth system 100 that includes point-of-birth instrument 105, smart device 190, and biochemical cartridge 200 as previously described. Additionally, the point-of-birth system 100 includes a newborn hearing screening mechanism 910. In this example, newborn hearing screening mechanism 910 is in direct communication with smart device 190. Features of NBS mobile app 192 can include processing information from/to the newborn hearing screening mechanism 910. In still another example, FIG. 59 shows a configuration in which the newborn hearing screening mechanism 910 is physically connected to the point-of-birth instrument 105 instead of to the smart device 190. In this example, point-of-birth instrument 105 passes information from the newborn hearing screening mechanism 910 to the NBS mobile app 192 on smart device 190 for processing.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range.

Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term “about,” when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term “about” when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A biochemical cartridge for newborn screening comprising:

a bottom substrate;

a top substrate spaced from the bottom substrate by a gap;

a cover positioned adjacent the top substrate; and a sample input well having a loading port and a well cap assembly for opening and closing the loading port;

wherein the sample input well is for collection of newborn testing fluids and the biochemical cartridge is for insertion into a newborn screening instrument for testing;

wherein the sample input well is a horizontal reservoir module and the biochemical cartridge further comprises a cover gasket, a horizontal reservoir module mounting plate, and mounting posts for holding the horizontal reservoir module;

wherein the well cap assembly comprises a foil strip for sealing fluid inside the horizontal reservoir module and the biochemical cartridge further comprises a take-up reel for winding the foil strip off of the horizontal reservoir module, a reel engaging feature secured to the top substrate, and a reservoir module capture feature.

2. The biochemical cartridge of claim 1 wherein the sample input well is integrated into the cover.

3. The biochemical cartridge of claim 1 wherein the cover comprises contoured regions.

4. The biochemical cartridge of claim 1 wherein the gap is an assay chamber.

5. The biochemical cartridge of claim 1 wherein the horizontal reservoir module comprises a first reservoir for holding a first sample fluid and a second reservoir for holding a second sample fluid.

6. The biochemical cartridge of claim 5 wherein the reservoirs are angled.

7. The biochemical cartridge of claim 6 wherein the reservoirs are angled 13 through 17 degrees.

8. The biochemical cartridge of claim 1 wherein the cartridge supports digital microfluidics.

9. The biochemical cartridge of claim 1 wherein the cartridge does not support digital microfluidics.

10. The biochemical cartridge of claim 1 wherein the newborn testing fluid is urine and/or blood.

11. The biochemical cartridge of claim 1 wherein the bottom substrate is a printed circuit board.

12. The biochemical cartridge of claim 1 wherein the gap between the bottom substrate and the top substrate comprises filler fluid.

* * * * *